US006931325B2

(12) United States Patent
Wall et al.

(10) Patent No.: US 6,931,325 B2
(45) Date of Patent: Aug. 16, 2005

(54) THREE DIMENSIONAL PROTEIN MAPPING

(75) Inventors: Daniel B. Wall, Ann Arbor, MI (US); David M. Lubman, Ann Arbor, MI (US); Timothy Barder, Darien, IL (US)

(73) Assignee: Regents of the University of Michigan, Ann Arbor, MI (US)

( * ) Notice: Subject to any disclaimer, the term of this patent is extended or adjusted under 35 U.S.C. 154(b) by 262 days.

(21) Appl. No.: 10/133,711

(22) Filed: Apr. 26, 2002

(65) Prior Publication Data

US 2003/0058239 A1 Mar. 27, 2003

Related U.S. Application Data

(63) Continuation-in-part of application No. 09/778,548, filed on Feb. 7, 2001.
(60) Provisional application No. 60/288,140, filed on May 2, 2001.

(51) Int. Cl.⁷ .............................................. G01N 33/48
(52) U.S. Cl. ......................................................... 702/19
(58) Field of Search ........................................... 702/19

(56) References Cited

U.S. PATENT DOCUMENTS

| | | | |
|---|---|---|---|
| 5,131,998 A | 7/1992 | Jorgenson et al. | 104/453 |
| 5,498,545 A | 3/1996 | Vestal et al. | 250/282 |
| 5,670,054 A | 9/1997 | Kibbey et al. | 210/656 |
| 6,002,127 A | 12/1999 | Vestal et al. | 250/282 |
| 6,139,734 A | 10/2000 | Settlage et al. | 210/198.2 |
| 6,315,905 B1 | 11/2001 | Settlage et al. | 210/656 |
| 2002/0039747 A1 | 4/2002 | Lubman et al. | 435/7.1 |
| 2002/0098595 A1 | 7/2002 | Lubman et al. | 436/178 |
| 2003/0058239 A1 | 3/2003 | Wall et al. | 345/419 |
| 2003/0143647 A1 | 7/2003 | Finn et al. | 435/7.23 |

FOREIGN PATENT DOCUMENTS

| | | |
|---|---|---|
| WO | 0617 048 A1 | 9/1994 |
| WO | WO 97/01755 | 1/1997 |
| WO | WO 98/23950 | 4/1998 |
| WO | WO 98/40395 | 9/1998 |
| WO | WO 01/58925 | 8/2001 |
| WO | WO 02088701 | 11/2002 |
| WO | WO 0158926 | 3/2003 |
| WO | WO 0159460 | 3/2003 |

OTHER PUBLICATIONS

Brunger et al. Crystallography & NMR System: A new software Suite for Macromolecular Structure Determination. Acta Crystallographica. Sep. 1, 2000, vol. D54, Part 9, pp. 905–921.*
U.S. Appl. No. 09/778,496, 20020039747, Lubman et al. filed Feb. 7, 2001.
U.S. Appl. No. 09/778,548, 20020098595 A1, Lubman et al. filed Feb. 7, 2001.
U.S. Appl. No. 09/968,930, Lubman et al. filed Oct. 10, 2001.
U.S. Appl. No. 10/133,711, 20030058239, Wall et al. filed Apr. 26, 2002.
U.S. Appl. No. 10/448,564, Lubman et al. filed May 30, 2003.
Aebersold et al., Internal amino acid sequence analysis of proteins separated by one– or two–dimensional gel electrophoresis after in situ protease digestion on nitrocellulose, Proc Natl Acad Sci U S A, 84(20):6970–6974 (1987).
Anderson et al.,A two–dimensional gel database of rat liver proteins useful in gene regulation and drug effects studies, Electrophoresis, 12(11):907–930 (1991).
Andrews et al., Analysis of DNA adducts using high–performance separation techniques coupled to electrospray ionization mass spectrometry, J Chromatogr A, 856(1–2):515–526 (1999).
Ayala et al., Use of Rotofor preparative isoelectrofocusing cell in protein purification procedure, Appl Biochem Biotechnol, 69(1):11–16 (1998).
Ball et al., Purification of synthetic peptides with the aid of reversible chromatographic probes, J Chromatogr A, 686(73–83 (1994).
Bini et al., Protein expression profiles in human breast ductal carcinoma and histologically normal tissue, Electrophoresis, 18(15):2832–2841 (1997).
Binz et al., A molecular scanner to automate proteomic research and to display proteome images, Anal Chem, 71(21):4981–4988 (1999).
Brown and Cooper, Regulation, substrates and functions of src, Biochim Biophys Acta, 1287(2–3):121–149 (1996).
Chen et al., Identification of proteins from two–dimensional gel electrophoresis of human erythroleukemia cells using capillary high performance liquid chromatography/electrospray–ion trap–reflectron time–of–flight mass spectrometry with two–dimensional topographic map analysis of in–gel tryptic digest products, Rapid Commun Mass Spectrom, 13(19):1907–1916 (1999).
Chen et al., Rapid identification and screening of proteins from whole cell lysates of human erythroleukemia cells in the liquid phase, using non–porous reversed phase high–performance liquid chromatography separations of proteins followed by matrix–assisted [correction of multi–assisted] laser desorption/ionization mass spectrometry analysis and sequence database searching, Rapid Commun Mass Spectrom, 12(24):1994–2003 (1998).

(Continued)

*Primary Examiner*—Ardin H. Marschel
*Assistant Examiner*—Channing S. Mahatan
(74) *Attorney, Agent, or Firm*—Medlen & Carroll, LLP

(57) ABSTRACT

The present invention relates to multi-phase protein separation methods capable of resolving and characterizing large numbers of cellular proteins, including methods for efficiently facilitating the transfer of protein samples between separation phases. In particular, the present invention provides systems and methods for the generation of multi-dimensional protein maps. The present invention thus provides improved methods for the analysis of samples containing large numbers of proteins.

12 Claims, 27 Drawing Sheets

OTHER PUBLICATIONS

Chong et al., Rapid screening of protein profiles of human breast cancer cell lines using non–porous reversed–phase high performance liquid chromatography separation with matrix–assisted laser desorption/ionization time–of–flight mass spectral analysis, Rapid Commun Mass Spectrom, 13(18):1808–1812 (1999).

Chong et al., Rapid profiling of E. coli proteins up to 500 kDa from whole cell lysates using matrix–assisted laser desorption/ionization time–of–flight mass spectrometry, Rapid Commun Mass Spectrom, 11(17):1900–1908 (1997).

Clauser et al., Role of accurate mass measurement (+/− 10 ppm) in protein identification strategies employing MS or MS/MS and database searching, Anal Chem, 71(14):2871–2882 (1999).

Cohen and Chait, Mass spectrometry of whole proteins eluted from sodium dodecyl sulfate–polyacrylamide gel electrophoresis gels, Anal Biochem, 247(2):257–267 (1997).

Courchesne et al., Comparison of in–gel and on–membrane digestion methods at low to sub–pmol level for subsequent peptide and fragment–ion mass analysis using matrix–assisted laser–desorption/ionization mass spectrometry, Electrophoresis, 18(3–4):369–381 (1997).

Dai et al., Two–layer sample preparation: a method for MALDI–MS analysis of complex peptide and protein mixtures, Anal Chem, 71(5):1087–1091 (1999).

Damerval, Quantification of silver–strained proteins resolved by two–dimensional electrophoresis: genetic variability as related to abundance and solubility in two maize lines, Electrophoresis, 15(12):1573–1579 (1994).

Davidsson and Nilsson, Peptide mapping of proteins in cerebrospinal fluid utilizing a rapid preparative two–dimensional electrophoretic procedure and matrix–assisted laser desorption/ionization mass spectrometry, Biochim Biophys Acta, 1473(2–3):391–399 (1999).

Davidsson et al., Characterization of proteins from human cerebrospinal fluid by a combination of preparative two–dimensional liquid–phase electrophoresis and matrix–assisted laser desorption/ionization time–of–flight mass spectrometry, Anal Chem, 71(3):642–647 (1999).

Dawson et al., MCF10AT: a model for the evolution of cancer from proliferative breast disease, Am J Pathol, 148(1):313–319 (1996.

Egan et al., Activation of Src in human breast tumor cell lines: elevated levels of phosphotyrosine phosphatase activity that preferentially recognizes the Src carboxy terminal negative regulatory tyrosine 530, Oncogene, 18(5):1227–1237 (1999).

Figeys and Aebersold, Nanoflow solvent gradient delivery from a microfabricated device for protein identifications by electrospray ionization mass spectrometry, Anal Chem, 70(18):3721–3727 (1998) (abstract only).

Figeys et al., Data–dependent modulation of solid–phase extraction capillary electrophoresis for the analysis of complex peptide and phosphopeptide mixtures by tandem mass spectrometry: application to endothelial nitric oxide synthase, Anal Chem, 71(13):2279–2287 (1999) (abstract only).

Figeys et al., Protein identification by solid phase microextraction–capillary zone electrophoresis–microelectrospray–tandem mass spectrometry, Nat Biotechnol, 14(11):1579–1583 (1996) (abstract only).

Figeys et al., An integrated microfluidics–tandem mass spectrometry system for automated protein analysis, Anal Chem, 70(18):3728–3734 (1998) (abstract only).

Figeys et al., Mirofabricated device coupled with an electrospray ionization quadrupole time–of–flight mass spectrometer: protein identifications based on enhanced–resolution mass spectrometry and tandem mass spectrometry data, Rapid Commun Mass Spectrom, 12(20):1435–1444 (1998) (abstract only).

Figeys et al., A microfabricated device for rapid protein identification by microelectrospray ion trap mass spectrometry, Anal Chem, 69(16):3153–3160 (1997) (abstract only).

Figeys et al., Optimization of solid phase microextraction—capillary zone electrophoresis—mass spectrometry for high sensitivity protein identification, Electrophoresis, 19(13):2338–2347 (1998) (abstract only).

Flyer et al., Identification by mass spectrometry of CD8(+)–T–cell Mycobacterium tuberculosis epitopes within the Rv0341 gene product, Infect Immun, 70(6):2926–2932 (2002).

Fuqua et al., Induction of the estrogen–regulated "24K" protein by heat shock, Cancer Res, 49(15):4126–4129 (1989).

Gasteiger et al., ExPASy: the proteomics server for in–depth protein knowledge and analysis Nucleic Acids Res. 31:3784–3788(2003).

Griffin et al., Direct database searching with MALDI–PSD spectra of peptides, Rapid Commun Mass Spectrom, 9(15):1546–1551 (1995).

Gottleib and Oren, p53 in growth control and neoplasia, Biochimica et Biophysica Acta, 1287(2–3):77–102 (1996).

Hanash, Advances in Electrophoresis, 1–44 (1998).

Hayakawa et al., Isoelectric focusing of biotinidase and lipoamidase with the addition of non–ionic detergent, Anal Chim Acta, 372(1–2):281–289 (1998).

Haynes et al., Proteome analysis: biological assay or data archive?, Electrophoresis, 19(11):1862–1871 (1998) (abstract only).

Henderson et al., Direct identification of an endogenous peptide recognized by multiple HLA–A2.1–specific cytotoxic T cells, Proc Natl Acad Sci U S A, 90(21): 10275–9 (1993).

Henzel et al., Identifying proteins from two–dimensional gels by molecular mass searching of peptide fragments in protein sequence database, Proc Natl Acad Sci U S A, 90(11):5011–5015 (1993).

Herbert, Advances in protein solubilisation for two–dimensional electrophoresis, Electrophoresis, 20(4–5):660–663 (1999).

Hermann et al., Mapping and identification of Corynebacterium glutamicum proteins by two–dimensional gel electrophoresis and microsequencing, Electrophoresis, 19(18):3217–3221 (1998) (abstract only).

Hoogland et al., The 1999 SWISS–2DPAGE database update., Nucleic Acids Res, 28:286–288 (2000).

Hungerford et al., Identification of a novel marker for primordial smooth muscle and its differential expression pattern is contractile vs noncontractile cells, J Cell Biol, 137(4):925–937 (1997).

Hunt et al., Characterization of peptides bound to the class 1 MHC molecle HLA–A2.1 by mass spectrometry, Science, 255(5049):1261–1263 (1992) (abstract only).

Immler et al., Identification of phosphorylated proteins from thrombin–activated human platelets isolated by two–dimensional gel electrophoresis by electrospray ionization–tandem mass spectrometry (ESI–MS/MS) and liquid chromatography–electrospray ionization–mass spectrometry (LC–ESI–MS), Electrophoresis, 19(6):1015–1023 (1998).

Kahn, From genome to proteome: looking at a cell's proteins, Science, 270(5235):369–370 (1995).

Kingan et al., The loss of female sex pheromone after mating in the corn earworm moth *Helicoverpa zea*: identification of a male pheromonostatic peptide, Proc Natl Acad Sci U S A, 92(11):5082–5086 (1995).

Lahm and Langen, Mass spectrometry: a tool for the identification of proteins separated by gels, Electrophoresis 21:2105–2114 (2000).

Lee, Protein separation using non–porous sorbents, J Chromatogr B Biomed Sci Appl, 699(1–2):29–45 (1997).

Li et al., Development of a three–dimensional topographic map display for capillary electrophoresis/mass spectrometry with an ion trap/reflectron time–of–flight mass spectrometer detector: applications to tryptic digests of isoforms of myelin basic protein, J Am Soc Mass Spectrom, 9(7):701–709 (1998).

Liang and Pardee, Differential display of eukaryotic messenger RNA by means of the polymerase chain reaction, Science, 257(5072):967–971 (1992).

Liang et al., Characterization of SDS—PAGE–separated proteins by matrix–assisted laser desorption/ionization mass spectrometry, Anal Chem, 68(6):1012–1018 (1996).

Liang et al., Determination of bacterial protein profiles by matrix–assisted laser desorption/ionization mass spectrometry with high–performance liquid chromatography, Rapid Commun Mass Spectrom, 10(10):1219–1226 (1996).

Link et al., Direct analysis of protein complexes using mass spectrometry, Nat Biotechnol, 17(7):676–682 (1999).

Loo et al., Mass Spectrometry of Proteins Directly from Polyacrylamide Gels, Anal Chem, 68(11):1910–1917 (1996).

Lopez, Better approaches to finding the needle in a haystack: optimizing proteome analysis through automation, Electrophoresis, 21(6):1082–1093 (2000).

MacNair et al., Rapid separation and characterization of protein and peptide mixtures using 1.5 microns diameter non–porous silica in packed capillary liquid chromatograpy/mass spectrometry, Rapid Commun Mass Spectrom, 11(12):1279–1285 (1997).

Maggiolini et al., Adrenal androgens stimulate the proliferation of breast cancer cells as direct activators of estrogen receptor alpha, Cancer Res, 59(19):4864–4869 (1999).

Mao et al., Activation of c–Src by receptor tyrosine kinases in human colon cancer cells with high metastic potential, Oncogene, 15(25):3083–3090 (1997).

Matsui et al., Immobilized pH gradient two–dimensional gel electrophoresis and mass spectrometric identification of cytokine–regulated proteins in ME–180 cervical carcinoma cells, Electrophoresis, 18(3–4):409–417 (1997)

Medzihradszky et al., Protein sequence and structural studies employing matrix–assisted laser desorption ionization–high energy collision–induced dissociation, International Journal of Mass Spectrometry and Ion Processes, 160(1–3):357–369 (1997).

Michael, Detection of electrospray ionization using a quadrupole ion trap storage/reflectron time–of–flight mass spectrometer, Anal Chem, 65(2614–2620 (1994).

Miller et al., Xenograft model of progressive human proliferative breast disease, J Natl Cancer Inst, 85(21):1725–1732 (1993).

Mills et al., Prospective study of exogenous hormone use and breast cancer in Seventh–day Adventists, Cancer, 64(3):591–597 (1989).

Mohammad et al., Induced expression of alpha–enolase in differentiated diffuse large cell lymphoma, Enzyme Protein, 48(1):37–44 (1994).

Molinari et al., Estradiol induces functional inactivation of p53 by intracellular redistribution, Cancer Res, 60(10):2594–2597 (2000).

Neidhardt et al., Genomically linked cellular protein databases derived from two–dimensional polyacrylamide gel electrophoresis, Electrophoresis, 10(2):116–122 (1989).

Neubauer and Mann, Mapping of phosphorylation sites of gel–isolated proteins by nanoelectrospray tandem mass spectrometry: potentials and limitations, Anal Chem, 71(1):235–242 (1999).

Nilsson et al., Isolation and characterization of proteins from human lymphocyte nuclei using matrix–assisted laser desorption/ionization time–of–flight mass spectrometry and post–source decay analysis, Rapid Commun Mass Spectrom, 11(6):610–612 (1997).

Nilsson et al., Identification of proteins in a human pleural exudate using two–dimensional preparative liquid–phase electrophoresis and matrix–assited laser desorption/ionization mass spectrometry, Electrophoresis, 20(4–5):860–865 (1999).

Nimura et al., Fast protein separation by reversed–phase high–performance liquid chromatography on octadecylsilyl–bonded non–porous silica gel. Effect of particle size of column packing on column efficiency., J Chromatogr, 585(207–211 (1991).

O'Farrell, High resolution two–dimensional electrophoresis of proteins, J Biol Chem, 250(10):4007–4021 (1975).

Opiteck et al., Two–dimensional SEC/RPLC coupled to mass spectrometry for the analysis of peptides, Anal Chem, 69(13):2283–2291 (1997).

Opiteck and Jorgenson, Comprehensive two–dimensional high–performance liquid chromatography for the isolation of overexpressed proteins and proteome mapping, Anal Biochem, 258(2):349–361 (1998).

Ottenhoff–Kalff et al., Characterization of protein tyrosine kinases from human breast cancer: involvement of the c–src oncogene product, Cancer Res, 51(17):4773–4778 (1992).

Ozturk et al., Detection of c–erbB–2 mRNAs using dig–labelled oligonucleotide probe with in situ hybridisation in human breast carcinoma: comparison with immunohistochemical results, Anal Cell Pathol, 16(4):201–209 (1998).

Patterson, Matrix–assisted laser–desorption/ionization mass spectrometric approaches for the identification of gel–separated proteins in the 5–50 pmol range, Electrophoresis, 16(7):1104–1114 (1995).

Patterson and Aebersold, Mass spectrometric approaches for the identification of gel–separated proteins, Electrophoresis, 16(10):1791–1814 (1995).

Pierce et al., Cutting edge: the HLA–A*0101–restricted HY minor histocompatibility antigen originates from DFFRY and contains a cysteinylated cysteine residue as identified by a novel mass spectrometric technique, J Immunol, 163(12):6360–6364 (1999).

Porter et al., Role of estrogen receptor/Sp1 complexes in estrogen–induced heat shock protein 27 gene expression, Mol Endocrinol, 10(11):1371–1378 (1996).

Qian and Lubman, Analysis of tryptic digests using microbore HPLC with an ion trap storage/reflectron time–of–flight detector, Anal Chem, 67(17):2870–2877 (1995).

Rasmussen et al., Two–dimensional gel database of human breast carcinoma cell expressed proteins: an update, Electrophoresis, 19(5):818–825 (1998).

Redner et al., The t(5;17) variant of acute promyelocytic leukemia expresses a nucleophosmin–retinoic acid receptor fusion, Blood, 87(3):882–886 (1996).

Regnier and Huang, Future potential of targeted component analysis by multidimensional liquid chromatography–mass spectrometry, J Chromatogr A, 750(1–2):3–10 (1996).

Reid et al., Capillary column chromatography improves sample preparation for mass spectrometric analysis: complete characterization of human alpha–enolase from two–dimensional gels following in situ proteolytic digestion, Electrophoresis, 19(6):946–955 (1998).

Reymond et al., Standardized characterization of gene expression in human colorectal epithelium by two–dimensional electrophoresis, Electrophoresis 18:2842–2848 (1997).

Richmond, High–throughput flow injection analysis–mass spectrometry with networked delivery of colour rendered results: the characterisation of liquid chromatography fractions, J Chromatogr A, 835(29–39 (1999).

Rodriquez et al., Towards stoichiometric silver staining of proteins resolved in complex two–dimensional electrophoresis gels: real–time analysis of pattern development, Electrophoresis, 14(7):628–637 (1993).

Rosen et al., Analysis of pp60c–src protein kinase activity in human tumor cell lines and tissues, J Biol Chem, 261(29):13754–13759 (1986).

Rosenfeld et al., In–gel digestion of proteins for internal sequence analysis after one– or two–dimensional gel electrophoresis, Anal Biochem, 203(1):173–179 (1992).

Rossomando et al., Identification of Tyr–185 as the site of tyrosine autophosphorylation of recombinant mitogen–activated protein kinase p42mapk, Proc Natl Acad Sci U S A, 89(13):5779–5783 (1992).

Ruddon, Cancer biology, Oxford University Press, 3rd, 318–340 (1995).

Russell et al., Cyclin D1 and D3 associate with the SCF complex and are coordinately elevated in breast cancer, Oncogene, 18(11):1983–1991 (1999).

Sanchez et al., Inside SWISS–2DPAGE database, Electrophoresis, 16(7):1131–1151 (1995).

Schweinfest and Pappas, Subtraction hybridization: an approach to the isolation of genes differentially expressed in cancer and other biological system (Review), Intern J Oncol, 1(499–506 (1992).

Shekhar et al., Transcriptional activation of functional endogenous estrogen receptor gene expression in MCF10AT cells: a model for early breast cancer, Int J Oncol, 13(5):907–915 (1998).

Shevchenko et al., Mass spectrometric sequencing of proteins silver–stained polyacrylamide gels, Anal Chem, 68(5):850–858 (1996).

Sirover, New insights into an old protein: the functional diversity of mammalian glyceraldehyde–3–phosphate dehydrogenase, Biochim Biophys Acta, 1432(2):159–184 (1999).

Soule et al., Isolation and characterization of a spontaneously immortalized human breast epithelial cell line, MCF–10, Cancer Res, 50(18):6075–6086 (1990).

Steller, Mechanisms and genes of cellular suicide, Science, 267(5203):1445–1449 (1995).

Sturtevant, Applications of differential–display reverse transcription–PCR to molecular pathogenesis and medical mycology, Clin Microbiol Rev, 13(3):408–427 (2000).

Tesarik et al., Estradiol modulates breast cancer cell apoptosis: a novel nongenomic steroid action relevant to carcinogenesis, Steroids, 64(1–2):22–27 (1999).

ten Hoeve et al., Isolation and chromosomal localization of CRKL, a human crk–like gene, Oncogene, 8(9):2469–2474 (1993).

Tetu et al., Prognostic significance of heat–shock protein–27 in node–positive breast carcinoma: an immunohistochemical study, Breast Cancer Res Treat, 36(1):93–97 (1995).

Thomas et al., Exogenous estrogens and other risk factors for breast cancer in women with benign breast disease, J Natl Cancer Inst, 69(5):1017–1025 (1982).

Toribio et al., Methods for chromatographic and electrophoretic separations and assay of NADP oxidoreductases, J Chromatogr Biomed Appl, 684(1–2):1–23 (1996).

Wall et al., Rapid profiling of induced proteins in bacteria using MALDI–TOF mass spectrometric detection of non-porous RP HPLC–separated whole cell lysates, Anal Chem, 71(17):3894–3900 (1999).

Wall, et al., Isolectric focusing nonporous RP HPLC: a two–dimensional liquid–phase separation method for mapping of cellular proteins with identification using MALDI–TOF mass spectrometry, Anal Chem, 72(6):1099–1111 (2000).

Wall, et al., Isolectric focusing nonporous silica reversed-phase high–performance liquid chromatography/electrospray ionization time–of–flight mass spectrometry: a three–dimensional liquid–phase protein separation method as applied to the human erythroleukemia cell–line, Rapid Commun Mass Spectrom, 15(18):1649–1661 (2001).

Wall, et al., Three–dimensional protein map according to p1, hydrophobicity and molecular mass, J Chromatogr B Analyt Technol Biomed Life Sci, 774(1):53–58 (2002).

Welsh et al., Variation in expression of hsp27 messenger ribonucleic acid during the cycle of the seminiferous epithelium and co–localization of hsp27 and microfilaments in Sertoli cells of the rat, Biol Reprod, 55(1):141–151 (1996).

Wilkins et al., From proteins to proteomes: large scale protein identification by two–dimensional electrophoresis and amino acid analysis, Biotechnology (N Y), 14(1):61–65 (1996).

Whittal and Li, High–resolution matrix–assisted laser desorption/ionization in a linear time–of–flight mass spectrometer, Anal Chem, 67(13):1950–1954 (1995).

Williams et al., Analysis of differential protein expression in normal and neoplastic human breast epithelial cell lines, Electrophoresis, 19(2):333–343 (1998).

Yang and Lee, Capillary isoelectric focusing–electrospray ionization Fourier transform ion cyclotron resonance mass spectrometry for protein characterization, Anal Chem, 70(15):3235–3241 (1998).

Yates et al., Direct analysis of protein mixtures by tandem mass spectrometry, J Protein Chem, 16(5):495–497 (1997).

Zuaro et al., Characterization of rat brain stathmin isoforms by two–dimensional gel electrophoresis–matrix assisted laser desorption/ionization and electrospray ionization–ion trap mass spectrometry, Electrophoresis, 19(5):867–876 (1998).

Carrier et al., "Using MultidimensionalMicroscale HPLC As An Alternative To 2D Page For Sample Preparation Prior To Nanole–MS/MS Protein Identification," Poster Paper Presented at ASMS 2000.

Wagner et al., "Protein Mapping by Two–Dimensaional High Performance Liquid Chromatography," Journal of Chromatography A., 893:293–305 (2000).

Isobe et al., Automated two–dimensional liquid chromatographic system for mapping proteins to highly complex mixtures, J. of Chromatography 588:115–123 (1991).

Opiteck et al., Comprehensive On–Line LC/LDC/MS of Protiens, Anal. Chem. 69:1518–1524 (1997).

* cited by examiner

*1 = Ovalbumin (45 kDa), 2 = Carbonic Anhydrase (29 kDa), 3 = BSA (67 kDa),

Key: the X marks the database coordinates of a given protein
The number is linked to Table 1 where the associated protein name is listed

A Fraction 1 (pH 6.75 – 6.55)

B Fraction 2 (pH 5.50 – 5.25)

C Fraction 3 (pH 5.20 – 4.90)

(a) Fraction collected from 3 to 4 minutes (b) Fraction collected from 7 to 8 minutes Schematic of 3D exp. design**

THREE DIMENSIONAL PROTEIN MAPPING

The present application is a continuation in part of U.S. patent application Ser. No. 09/778,548, filed Feb. 2, 2001 and claims priority to U.S. Provisional Patent application Ser. No. 60/288,140, filed May 2, 2001.

The present invention was made, in part, with government funding under National Institutes of Health under grant No. 2-R01GM49500-5 and the National Science Foundation grant No. DBI-9987220. The government has certain rights in this invention.

FIELD OF THE INVENTION

The present invention relates to multi-phase protein separation methods capable of resolving and characterizing large numbers of cellular proteins, including methods for efficiently facilitating the transfer of protein samples between separation phases. In particular, the present invention provides systems and methods for the generation of multi-dimensional protein maps.

BACKGROUND OF THE INVENTION

As the nucleic acid sequences of a number of genomes, including the human genome, become available, there is an increasing need to interpret this wealth of information. While the availability of nucleic acid sequence allows for the prediction and identification of genes, it does not explain the expression patterns of the proteins produced from these genes. The genome does not describe the dynamic processes on the protein level. For example, the identity of genes and the level of gene expression does not represent the amount of active protein in a cell nor does the gene sequence describe post-translational modifications that are essential for the function and activity of proteins. Thus, in parallel with the genome projects there has begun an attempt to understand the proteome (i.e., the quantitative protein expression pattern of a genome under defined conditions) of various cells, tissues, and species. Proteome research seeks to identify targets for drug discovery and development and provide information for diagnostics (e.g., tumor markers).

An important area of research is the study of the protein content of cells (i.e., the identity of and amount of expressed proteins in a cell). This field requires methods that can separate out large numbers of proteins and can do so quantitatively so that changes in expression or structure of proteins can be detected. The method generally used to achieve such cellular protein separations is 2-D PAGE. This method is capable of resolving hundreds of proteins based upon pI in one dimension and protein size in the second dimension. The proteins separated by this method are visualized using a staining method that can generally be quantified. The result is a 2-dimensional image where the protein map is based on pI and approximate molecular weight. By the use of computer based image analysis techniques, one can search for proteins that are differentially expressed in various cell lines. These methods are used to monitor changes in protein expression that are linked to conditions such as cell transformation and cancer progression, cell aging, the response of cells to environmental insult, and the response of cells to pharmaceutical agents. Once changes in protein expression have been identified, then one can further analyze target proteins to determine their identity and whether they have been altered from their expected structure by sequence changes or post-translational modifications.

Although 2-D PAGE is still widely used for protein analysis, the method has several limitations including the fact that it is labor intensive, time consuming, difficult to automate and often not readily reproducible. In addition, quantitation, especially in differential expression experiments, is often difficult and limited in dynamic range. Also, while the 2-D gel does produce an image of the proteins in the cell, the mass determination is often only accurate to 5–10%, and the method is difficult to interface to mass spectrometric techniques for further analysis.

Another limitation of 2-D PAGE is the amount of protein loaded per gel which is generally below 250 $\mu$g. The amount of protein in any given spot may therefore be too low for further analysis. For Coomassie brilliant blue (CBB) stained gels the limit of detection is 100 ng per spot while for silver stained gels the limit of detection is 1–10 ng. Furthermore, proteins that have been isolated in 2-D gels are embedded inside the gel structure and are not free in solution, thus making it difficult to extract the protein for further analysis. Because of these limitations, the art is in need of protein mapping methods that are efficient, automated, and have broader resolution capabilities than presently available technologies.

SUMMARY OF THE INVENTION

The present invention relates to multi-phase protein separation methods capable of resolving and characterizing large numbers of cellular proteins, including methods for efficiently facilitating the transfer of protein samples between separation phases. In particular, the present invention provides an automated system for the separation, identification, and characterization of protein samples.

Accordingly, in some embodiments, the present invention provides a computer system comprising computer software configured to generate 3-dimensional protein maps representing a separated protein sample comprising a plurality of proteins; and a display screen configured to display the three dimensional protein maps, wherein the display screen is operably linked to said computer software. In some embodiments, the 3-dimensional protein maps display isoelectric point, hydrophobicity, and mass of the separated protein sample. In some embodiments, the 3-dimensional protein map represents the plurality of proteins as spots, wherein each of the spots represents one of the plurality of proteins. In some embodiments, the protein hydrophobicity is calculated based on percent of solvent required to elute each of the plurality of proteins from an NP RP HPLC column. In some embodiments, the solvent is acetonitrile. In some embodiments, the 3-dimensional protein map further comprises hyperlinks to a protein information database. In some embodiments, each of the hyperlinks correspond to one of the spots, and wherein said information database comprises information selected from the group consisting of protein identity, molecular weight, relative abundance, isolectric point, and hydrophobicity.

In some embodiments, the present invention additionally provides a method for displaying 3-dimensional protein maps, comprising providing a computer system comprising software and a display screen operably linked to said software; and data describing 3 or more properties of a separated protein sample, wherein the separated protein sample comprises a plurality of proteins; and generating a 3-dimensional protein map from the data using the software; and displaying the 3-dimensional protein map using the display screen. In some embodiments, the 3 or more properties are protein isoelectric point, hydrophobicity, and mass, and the 3-dimensional protein map displays the protein isoelectric point, hydrophobicity, and mass of said separated protein sample. In some embodiments, the 3-dimensional protein map represents the plurality of proteins as spots, wherein each of the spots corresponds to one of the plurality of proteins. In some embodiments, the protein hydrophobicity is calculated based on percent of solvent required to elute each of the plurality of proteins from an NP RP HPLC column. In some embodiments, the solvent is acetonitrile. In some embodiments, the 3-dimensional protein map further comprises hyperlinks to a protein information database. In some embodiments, each of the hyperlinks correspond to one of the spots, and wherein the information database comprises information selected from the group consisting of protein identity, molecular weight, relative abundance, isolectric point, and hydrophobicity.

DESCRIPTION OF THE FIGURES

FIG. 11B shows the resulting molecular weight mass spectrum for actin where the two forms of actin are separated.

GENERAL DESCRIPTION OF THE INVENTION

Figure 1:
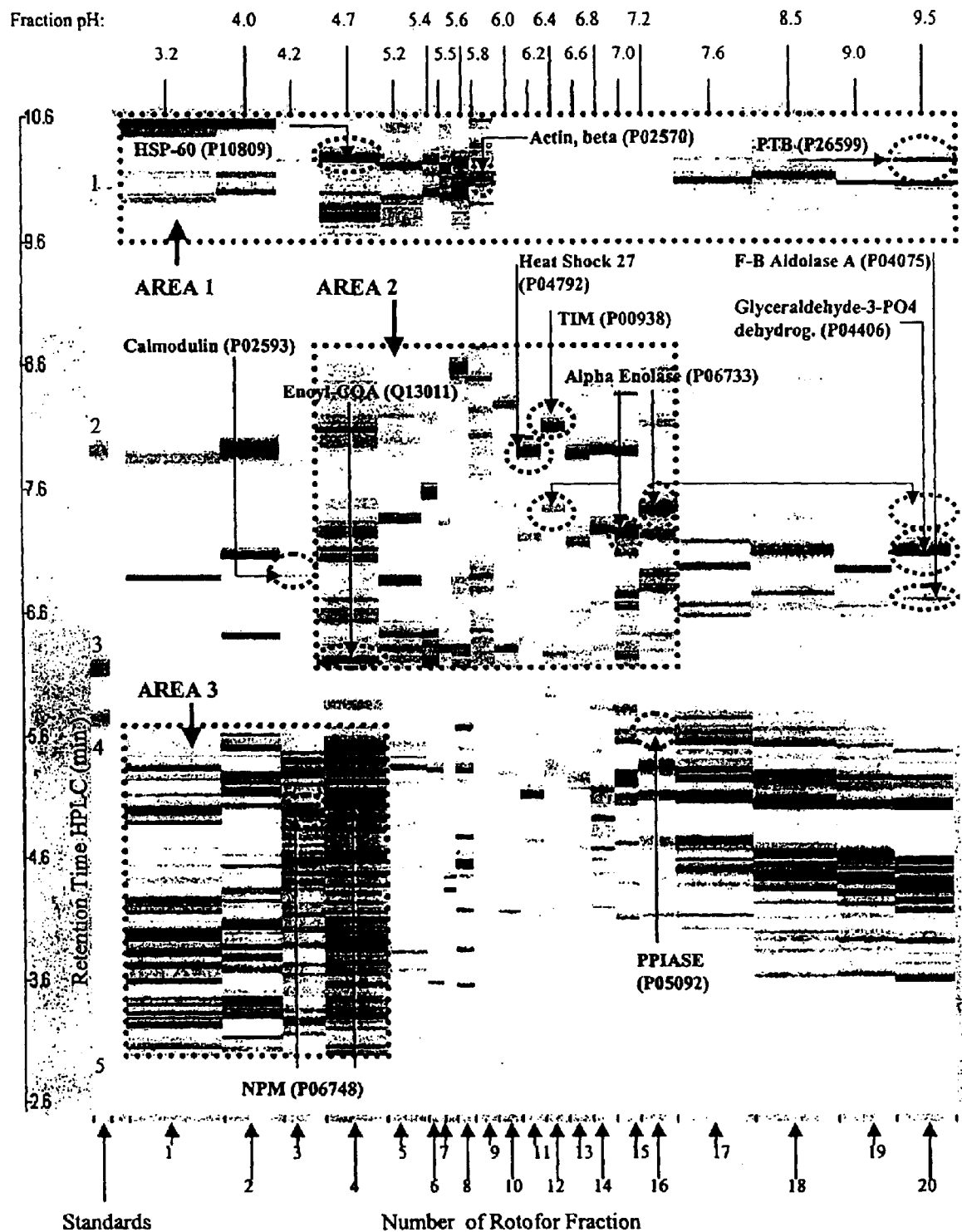
FIG. 1 shows an example 2-D protein display using Isoelectric Focusing Non-Porous Reverse Phase HPLC (IEF-NP RP HPLC) separation of human erythroleukemia cell lysate proteins in one embodiment of the present invention.

The present invention relates to multi-phase protein separation methods capable of resolving large numbers of cellular proteins, including methods for efficiently facilitating the transfer of protein samples between separation phases. The methods of the present invention provide protein profile maps for imaging and comparing protein expression patterns. The present invention provides alternatives to traditional 2-D gel separation methods for the screening of protein profiles. Many limitations of traditional 2-D PAGE arise from its use of the gel as the separation media. The present invention provides alternative media for the separation that offer significant advantages over 2-D PAGE techniques. For example, in some embodiments, the present invention provides methods that use two dimensional separations, where the second dimensional separation occurs in the liquid phase, rather than 2-D PAGE techniques where the final separation occurs in gel.

The present invention provides systems and methods for protein separation and mapping that are highly efficient, amenable to automation, and provide detailed resolution. For example, in some methods of the present invention, proteins are separated according to their pI, using isoelectric focusing (IEF) (e.g., in the Rotofor); according to their hydrophobicity using non-porous reverse phase HPLC (NPS RP HPLC); and according to mass using ESI oa TOF/MS or other mass spectrometry techniques. The present invention further provides novel techniques for eluting proteins from a separation apparatus (e.g., the first phase separation apparatus). For example, in one embodiment of the present invention, the proteins eluted from the first dimension are "peeled off" from the column according to their pH, either one pH unit or fraction thereof, at a time. In some embodiments, these focused liquid fractions are then separated according to their hydrophobicity and size (or other desired properties) in the second dimension. Liquid fractions from, for example, NP-RP-HPLC can be conveniently analyzed directly on-line using mass spectrometry (e.g., ESI-oaTOF) to obtain their molecular weight and relative abundance, which provides a third dimension. As a result, a virtual 2-D protein image is created and is analogous to a 2-D gel image.

Experiments conducted during the development of the present invention have demonstrated that these methods are capable of separating large numbers of proteins. The 2-D image of these proteins, analogous to that of a 2-D gel, can be generated for the purpose of observing distinctive patterns from a particular cell line. This protein pattern provides relative quantitative information, high mass resolution and high accuracy pI and mass values. Given that the intensity, mass and pI values are reproducible, one can study differential expression of proteins where the resulting 2-D images from different cells, tissues, or samples can be quantitatively compared to identify points of interest. Furthermore, automation and speed of analysis are greatly facilitated given that the proteins remain in the liquid phase throughout the separation. The method, abbreviated IEF-NPS RP HPLC-ESI oa TOF/MS is shown to be a viable alternative for the separation of complex protein mixtures and the generation of high-resolution 2-D images of cellular protein expression.

In some embodiments of the present invention, proteins are separated in a first dimension using any of a large number of protein separation techniques including, but not limited to, ion exclusion, ion exchange, normal/reversed phase partition, size exclusion, ligand exchange, liquid/gel phase isoelectric focusing, and adsorption chromatography. In some preferred embodiments of the present invention, the first dimension is a liquid phase separation method. The sample from the first separation is passed through a second dimension separation. In preferred embodiments of the present invention, the second dimension separation is conducted in liquid phase. The products from the second dimension separation are then characterized. For example, in preferred embodiments, the products of the second separation step are detected and displayed in a 2-D format based on the physical properties of the proteins that were distinguished in the first and second separation steps (e.g., under conditions such that the first and the second physical properties are revealed for at least a portion of the proteins). The products may be further analyzed, for example, by mass spectrometry to determine the mass and/or identity of the products or a subset of the products. In these embodiments, a three dimensional characterization can be applied (i.e., based on the physical properties of the first two separation steps and the mass spectrometry data). It is contemplated that other protein processing steps can be conducted at any stage of the process.

In certain embodiments of the present invention, the steps are combined in an automated system. In preferred embodiments, each of the steps is automated. For example, the present invention provides a system that includes each of the separation and detection elements in operable combination so that a protein sample is applied to the system and the user receives expression map displays or other desired data output. To achieve automation, in preferred embodiments, the products of each step should be compatible with the subsequent step or steps.

In one illustrative embodiment of the present invention proteins are separated according to their pI, using isoelectric focusing (IEF) in a Rotofor and according to their hydrophobicity and molecular weight using NP RP HPLC. This combined separation method is abbreviated IEF-NP RP HPLC. When coupled with mass spectrometry (MS) this technique becomes three-dimensional and allows for the creation of a protein map that tells the pI and the molecular weight of the proteins in question. This information can be plotted in an image that also depicts protein abundance. The end result is a high-resolution image showing a complex pattern of proteins separated by pI and molecular weight and indicating relative protein abundances. This image can be used to determine how the proteins in a given cell line or tissue may change due to some disease state, pharmaceutical treatment, natural or induced differentiation, or change in environmental conditions. The image allows the observer to determine changes in pI, molecular weight, and abundance of any protein in the image. When interfaced to MS the identity of any target protein may also be obtained via enzymatic digests and peptide mass map analyses. In addition, this technique has the advantage of very high loadability (e.g., 1 gram) such that the lower abundance proteins may be detected.

In traditional 2-D PAGE separation and display techniques, the second phase separation is conducted in a gel (i.e., not a liquid phase) and the proteins are separated and detected by differences in molecular weight. In contrast, in some embodiments of the present invention, the second phase separation is conducted in liquid phase. The products of the second phase separation techniques of the present invention are much more amenable to further characterization and to interpretation of data produced from the second phase. For example, in some embodiments of the present invention, the second phase is conducted using HPLC where the separated protein products are readily detected as peak fractions and interpreted and displayed in two dimensions by a computer based on the physical properties of the first and second separation steps. The products of HPLC separation, being in the liquid phase, are readily used in further detection steps (e.g., mass spectrometry). The methods of the present invention, as compared to traditional 2-D PAGE, allow more sample to be analyzed, are more efficient, facilitate automation, and allow for the analysis of proteins that are not detectable with 2-D PAGE.

For example, in one illustrative embodiment of the present invention, the protein profile of human erythroleukemia (HEL) cells has been analyzed using the methods of the present invention as well as traditional gel based methods for comparison purposes. Two-dimensional images were generated representing each of the separation methods used. Proteins were separated and then collected using both the IEF-NP RP HPLC of the present invention and 2-D PAGE methods. These proteins were then enzymatically digested and the peptide mass maps were determined by MALDI-TOF MS (if a protein cannot be unambiguously identified by this method, further analysis is made by any number of techniques including, but not limited to, LC/MS-MS, PSD-MALDI, NMR, Western blotting, Edman sequence analysis and mass spectrometry can help with further analysis of proteins [See e.g., Yates, J. Mass Spec., 33:1 (1998); Chen et al., Rap. Comm. Mass Spec., 13:1907 (1999); Neubauer and Mann, Anal. Chem. 71:235 (1999); Zugaro et al., Electrophoresis 19:867 (1998); Immler et al., Electrophoresis 19:1015 (1998); Reid et al, Electrophoresis 19:946 (1998); Rosenfeld, et al., Anal. Biochem., 203:173 (1992); Matsui et al., Electrophoresis 18:409 (1997); Patterson and Aebersold, Electrophoresis 16:1791 (1995)]).

In some embodiments, the proteins were tentatively identified using MS-Fit to search the peptide mass maps against the Swiss and NCBInr protein databases. This work demonstrated that a large number of proteins, with a useful mass range, were separated using the methods of the present invention and that a 2-D image of these proteins was reproducibly generated for the purpose of observing distinctive patterns that are associated with a particular cell line. The methods of the present invention allowed for the detection of proteins not observed with the 2-D PAGE technique. Automation and speed of analysis are also greatly facilitated given that the proteins remain in the liquid phase throughout the separation.

In some embodiments, the present invention provides an automated protein separation and characterization system. The system is fully integrated and transfers and coordinates multi-phase, orthogonal separation methods. In some embodiments, the information is transferred by the automated system to software for the generation of multi-dimensional protein maps. Automation provides increased speed, efficiency, and sample recovery while eliminating potential sources of contamination and sample loss.

Thus, the methods of the present invention are shown to be an advantageous technique for the generation of images of protein expression profiles as well as for the collection of individual proteins for further analyses. These capabilities allow one to monitor changes in protein expression that are linked to differentiation pathways as well as particular conditions such as cancer (See e.g., Hanash, Advances in Electrophoresis; Chrambach, A., Editor, pp 1–44 [1998]), cell aging (See e.g., Steller, Science 267:1445 [1995]), the response of cells to environmental insult (See e.g., Welsh et al., Biol. Reprod., 55:141 [1996]), or the response of cells to some pharmaceutical agent. Having identified significant changes in protein expression, one can then further analyze proteins of interest to determine their identity and whether they have been altered from their expected structure by sequence changes or post-translational modifications.

Definitions

To facilitate an understanding of the present invention, a number of terms and phrases are defined below:

As used herein, the term "multiphase protein separation" refers to protein separation comprising at least two separation steps. In some embodiments, multiphase protein separation refers to two or more separation steps that separate proteins based on different physical properties of the protein (e.g., a first step that separates based on protein charge and a second step that separates based on protein hydrophobicity).

As used herein, the term "protein profile maps" refers to representations of the protein content of a sample. For example, "protein profile map" includes 2-dimensional and 3-dimensional displays of total protein expressed in a given cell. In some embodiments, protein profile maps may also display subsets of total protein in a cell. Protein profile maps may be used for comparing "protein expression patterns" (e.g., the amount and identity of proteins expressed in a sample) between two or more samples. Such comparing find use, for example, in identifying proteins that are present in one sample (e.g., a cancer cell) and not in another (e.g., normal tissue), or are over- or under-expressed in one sample compared to the other. As used herein, the term "3-dimensional protein map" refers to a "protein profile map" that simultaneously displays three distinct properties of proteins (e.g., on separate axis of a graph).

As used herein, the term "separating apparatus capable of separating proteins based on a physical property" refers to compositions or systems capable of separating proteins (e.g., at least one protein) from one another based on differences in a physical property between proteins present in a sample containing two or more protein species. For example, a variety of protein separation columns and composition are contemplated including, but not limited to ion exclusion, ion exchange, normal/reversed phase partition, size exclusion, ligand exchange, liquid/gel phase isoelectric focusing, and adsorption chromatography. These and other apparatuses are capable of separating proteins from one another based on their size, charge, hydrophobicity, and ligand binding affinity, among other properties. A "liquid phase" separating apparatus is a separating apparatus that utilizes protein samples contained in liquid solution, wherein proteins remain solubilized in liquid phase during separation and wherein the product (e.g., fractions) collected from the apparatus are in the liquid phase. This is in contrast to gel electrophoresis apparatuses, wherein the proteins enter into a gel phase during separation. Liquid phase proteins are much more amenable to recovery/extraction of proteins as compared to gel phase. In some embodiments, liquid phase proteins samples may be used in multi-step (e.g., multiple separation and characterization steps) processes without the need to alter the sample prior to treatment in each subsequent step (e.g., without the need for recovery/extraction and resolubilization of proteins).

As used herein, the term "3-dimensional protein maps representing a separated protein sample" refers to a 3-dimensional protein map that displays quantitative or qualitative data corresponding to proteins in the separated protein sample. Any data that describes proteins may be displayed, including but not limited to protein hydrophobicity, isoelectric point, mass, and abundance.

As used herein, the term "data describing 3 or more properties of a separated protein sample" refers to quantitative or qualitative data corresponding to proteins in the separated protein sample. Any data that describes proteins may be displayed, including but not limited to protein hydrophobicity, isoelectric point, mass, and abundance.

As used herein, the term "displaying proteins" refers to a variety of techniques used to interpret the presence of proteins within a protein sample. Displaying includes, but is not limited to, visualizing proteins on a computer display representation, diagram, autoradiographic film, list, table, chart, etc. "Displaying proteins under conditions that first and second physical properties are revealed" refers to displaying proteins (e.g., proteins, or a subset of proteins obtained from a separating apparatus) such that at least two different physical properties of each displayed protein are revealed or detectable. For example, such displays include, but are not limited to, tables including columns describing (e.g., quantitating) the first and second physical property of each protein and two-dimensional displays where each protein is represented by an X,Y locations where the X and Y coordinates are defined by the first and second physical properties, respectively, or vice versa. Such displays also include multi-dimensional displays (e.g., three dimensional displays) that include additional physical properties.

As used herein, the terms "display system" and "display component" refers to systems and components capable of physically displaying protein maps (e.g., 3-dimensional protein maps). In some embodiments, display systems and display components comprise "computer processors," "computer memory," "software," and "display screens."

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refers to a device that is able to read a program from a computer memory (e.g., ROM or other computer memory) and perform a set of steps according to the program.

As used herein, the term "hyperlink" refers to a navigational link from one document to another, or from one portion (or component) of a document to another. Typically, a hyperlink is displayed as a highlighted word or phrase that can be selected by clicking on it using a mouse to jump to the associated document or documented portion.

As used herein, the term "display screen" refers to a screen (e.g., monitor) for the visual display of computer or electronically generated images. Images are generally displayed as a pluarlity of pixels.

As used herein, the term "computer system" refers to a system comprising a computer processor, computer memory, and a computer video screen in operable combination. Computer systems may also include computer software.

As used herein, the term "protein information database" refers to a database comprising information relating to quantitative and physical parameters of a separated protein cell sample. In some embodiments, information contained in the database includes but is not limited to, protein identity, molecular weight, relative abundance, isoelectric point, hydrophobicity, cell type, and cell origin. In some embodiments, protein informational databases are located on a server that is connected to a network (e.g., an internet or intranet).

As used herein, "characterizing protein samples under conditions such that first and second physical properties are analyzed" refers to the characterization of two or more proteins, wherein two different physical properties are assigned to each analyzed (e.g., displayed, computed, etc.) protein and wherein a result of the characterization is the categorization (i.e., grouping and/or distinguishing) of the proteins based on these two different physical properties. For example, in some embodiments, two proteins are separated based on isoelectric point and hydrophobicity.

As used herein, the term "comparing first and second physical properties of separated protein samples" refers to the comparison of two or more protein samples (or individual proteins) based on two different physical properties of the proteins within each protein sample. Such comparing includes grouping of proteins in the samples based on the two physical properties and comparing certain groups based on just one of the two physical properties (i.e., the grouping incorporates a comparison of the other physical property).

As used herein, the term "delivery apparatus capable of receiving a separated protein from a separating apparatus" refers to any apparatus (e.g., microtube, trough, chamber, etc.) that receives one or more fractions or protein samples from a protein separating apparatus and delivers them to another apparatus (e.g., another protein separation apparatus, a reaction chamber, a mass spectrometry apparatus, etc.).

As used herein, the term "detection system capable of detecting proteins" refers to any detection apparatus, assay, or system that detects proteins derived from a protein separating apparatus (e.g., proteins in one or fractions collected from a separating apparatus). Such detection systems may detect properties of the protein itself (e.g., UV spectroscopy) or may detect labels (e.g., fluorescent labels) or other detectable signals associated with the protein. The detection system converts the detected criteria (e.g., absorbance, fluorescence, luminescence etc.) of the protein into a signal that can be processed or stored electronically or through similar means (e.g., detected through the use of a photomultiplier tube or similar system).

As used herein, the term "buffer compatible with an apparatus" and "buffer compatible with mass spectrometry" refer to buffers that are suitable for use in such apparatuses (e.g., protein separation apparatuses) and techniques. A buffer is suitable where the reaction that occurs in the presence of the buffer produces a result consistent with the intended purpose of the apparatus or method. For example, a buffer compatible with a protein separation apparatus solubilizes the protein and allows proteins to be separated and collected from the apparatus. A buffer compatible with mass spectrometry is a buffer that solubilizes the protein or protein fragment and allows for the detection of ions following mass spectrometry. A suitable buffer does not substantially interfere with the apparatus or method so as to prevent its intended purpose and result (i.e., some interference may be allowed).

As used herein, the term "automated sample handling device" refers to any device capable of transporting a sample (e.g., a separated or un-separated protein sample) between components (e.g., separating apparatus) of an automated method or system (e.g., an automated protein characterization system). An automated sample handling device may comprise physical means for transporting sample (e.g., multiple lines of tubing connected to a multi-channel valve). In some embodiments, an automated sample handling device is connected to a centralized control network.

As used herein, the term "switchable multi channel valve" refers to a valve that directs the flow of liquid through an automated sample handling device. The valve preferably has a plurality of channels (e.g., 2 or more, and preferably 4 or more, and more preferably, 6 or more). In addition, in some embodiments, flow to individual channels is "switched" on an off. In some embodiments, valve switching is controlled by a centralized control system. A switchable multi-channel valve allows multiple apparatus to be connected to one automated sample handler. For example, sample can first be directed through one apparatus of a system (e.g., a first chromatography apparatus). The sample can then be directed through a different channel of the valve to a second apparatus (e.g., a second chromatography apparatus).

As used herein, the terms "centralized control system" or "centralized control network" refer to information and equipment management systems (e.g., a computer processor and computer memory) operable linked to multiple devices or apparatus (e.g., automated sample handling devices and separating apparatus). In preferred embodiments, the centralized control network is configured to control the operations or the apparatus an device linked to the network. For example, in some embodiments, the centralized control network controls the operation of multiple chromatography apparatus, the transfer of sample between the apparatus, and the analysis and presentation of data.

As used herein, the term "directly feeding" a protein sample from one apparatus to another apparatus refers to the passage of proteins from the first apparatus to the second apparatus without any intervening processing steps. For example, a protein that is directly fed from a protein separating apparatus to a mass spectrometry apparatus does not undergo any intervening digestion steps (i.e., the protein received by the mass spectrometry apparatus is undigested protein).

As used herein, the term "sample" is used in its broadest sense. In one sense it can refer to a cell lysate. In another sense, it is meant to include a specimen or culture obtained from any source, including biological and environmental samples. Biological samples may be obtained from animals (including humans) and encompass fluids, solids, tissues, and gases. Biological samples include blood products (e.g., plasma and serum), saliva, urine, and the like and includes substances from plants and microorganisms. Environmental samples include environmental material such as surface matter, soil, water, and industrial samples. These examples are not to be construed as limiting the sample types applicable to the present invention.

DETAILED DESCRIPTION OF THE INVENTION

The present invention provides a novel multi-dimensional separation method that is capable of resolving large numbers of cellular proteins. The following discussion is provided in four sections: I) two-phase separation techniques; II) improved elution techniques; III) mass spectroscopic analysis and 2-D display systems and methods; and IV) automated 3D HPLC/MC methods for rapid protein characterization.

I) Two-Phase Separation Techniques

The first dimension separates proteins based on a first physical property. For example, in some embodiments of the present invention proteins are separated by pI using isoelectric focusing in the first dimension (See e.g., Righetti, Laboratory Techniques in Biochemistry and Molecular Biology; Work, T. S.; Burdon, R. H., Elsevier: Amsterdam, p 10 [1983]). However, the first dimension may employ any number of separation techniques including, but not limited to, ion exclusion, ion exchange, normal/reversed phase partition, size exclusion, ligand exchange, liquid/gel phase isoelectric focusing, and adsorption chromatography. In some embodiments (e.g., some automated embodiments), it is preferred that the first dimension be conducted in the liquid phase to enable products of the separation step to be fed directly into a second liquid phase separation step.

The second dimension separates proteins based on a second physical property (i.e., a different property than the first physical property) and is preferably conducted in the liquid phase (e.g., liquid-phase size exclusion). For example, in some embodiments of the present invention proteins are separated by hydrophobicity using non-porous reversed phase HPLC in the second dimension (See e.g., Liang et al, Rap. Comm. Mass Spec., 10:1219 [1996]; Griffin et al., Rap. Comm. Mass Spec., 9:1546 [1995]; Opiteck et al., Anal. Biochem. 258:344 [1998]; Nilsson et al., Rap. Comm. Mass Spec., 11:610 [1997]; Chen et al., Rap. Comm. Mass Spec., 12:1994 [1998]; Wall et al., Anal. Chem., 71:3894 [1999]; Chong et al., Rap. Comm. Mass Spec., 13:1808 [1999]). This method provides for exceptionally fast and reproducible high-resolution separations of proteins according to their hydrophobicity and molecular weight. The non-porous (NP) silica packing material used in these reverse phase (RP) separations eliminates problems associated with porosity and low recovery of larger proteins, as well as reducing analysis times by as much as one third. Separation efficiency remains high due to the small diameter of the spherical particles, as does the loadability of the NP RP HPLC columns. However, the second dimension may employ any number of separation techniques. For example, in one embodiment, 1-D SDS PAGE lane gel is used. Having the second dimension conducted in the liquid phase facilitates efficient analysis of the separated proteins and enables products to be fed directly into additional analysis steps (e.g., directly into mass spectrometry analysis).

In certain embodiments of the present invention, proteins obtained from the second separation step are mapped using software (available from Dr. Stephen J. Parus, University of Michigan, Department of Chemistry, 930 N. University Ave., Ann Arbor, Mich. 48109-1055) in order to create a protein pattern analogous to that of the 2-D PAGE image—although based on the two physical properties used in the two separation steps rather than by a second gel-based size separation technique. In some embodiments, RP HPLC peaks are represented by bands of different intensity in the 2-D image, according to the intensity of the peaks eluting from the HPLC. In some embodiments, peaks are collected as the eluent of the HPLC separation in the liquid phase.

In some embodiments, the proteins collected from the second dimension were identified using proteolytic enzymes, MALDI-TOF MS and MSFit database searching. In an example using human erythroleukemia cell lysate, using IEF-NP RP HPLC, approximately 700 bands were resolved in a pI range from 3.2 to 9.5 and 38 different proteins with molecular weights ranging from 12 kDa to 75 kDa were identified. In comparison to a 2-D gel separation of the same human erythroleukemia (HEL) cell line lysate, the IEF-NP RP HPLC produced improved resolution of low mass and basic proteins. In addition, the proteins remained in the liquid phase throughout the separation, thus making the entire procedure highly amenable to automation and high throughput.

Certain preferred embodiments are described in detail below. These illustrative examples are not intended to limit the scope of the invention. For example, although the examples are described using human tissues and samples, the methods and apparatuses of the present invention can be used with any desired protein samples including samples from plants and microorganisms.

A. IEF-NP RP HPLC Method

The following description provides certain preferred embodiments for conducting isoelectric separation (first dimension) and NP RP HPLC separation (second dimension) according to the methods of the present invention.

1. IEF Separation

Proteins are extracted from cells using a lysis buffer. To facilitate an efficient process, this lysis buffer should be compatible with the downstream separation and analysis steps (e.g., NP RP HPLC and MALDI-TOF-MS) to allow direct use of the products from each step into subsequent steps. Such a buffer is an important aspect of automating the process. Thus, the preferred buffer should meet two criteria: 1) it solubilizes proteins and 2) it is compatible with each of the steps in the separation/analysis methods. Although the present invention provides suitable buffers for use in the particular method configurations described below, one skilled in the art can determine the suitability of a buffer for any particular configuration by solubilizing protein sample in the buffer. If the buffer solubilizes the protein, the sample is run through the particular configuration of separation and detection methods desired. A positive result is achieved if the final step of the desired configuration produces detectable information (e.g., ions are detected in a mass spectrometry analysis). Alternately, the product of each step in the method can be analyzed to determine the presence of the desired product (e.g., determining whether protein elutes from the separation steps).

After extraction in the lysis buffer, proteins are initially separated in a first dimension. The goal in this step is that the proteins are isolated in a liquid fraction that is compatible with subsequent NP RP HPLC and mass spectrometry steps. In these embodiments, n-octyl β-D-glucopyranoside (OG1, from Sigma) is used in the buffer, n-octyl β-D-glucopyranoside is one of the few detergents that is compatible with both NP RP HPLC and subsequent mass spectrometry analyses. It is contemplated that detergents of the formula n-octyl SUGARpyranoside find use in these embodiments. The lysis buffer utilized was 6M urea, 2M thiourea, 1.0% n-octyl β-D-glucopyranoside, 10 mM dithioerythritol and 2.5% (w/v) carrier ampholytes (3.5 to 10 pI)). After extraction, the supernatant protein solution is loaded to a device that can separate the proteins according to their pI by isoelectric focusing (IEF). Here the proteins are solubilized in a running buffer that again should be compatible with NP RP HPLC. A suitable running buffer is 6M urea, 2M thiourea, 0.5% n-octyl β-D-glucopyranoside, 10 mM dithioerythritol and 2.5% (w/v) carrier ampholytes (3.5 to 10 pI).

Three exemplary devices that may be used for this step are:

a) Rotofor

This device (Biorad) separates proteins in the liquid phase according to their pI (See e.g., Ayala et al., Appl. Biochem. Biotech. 69:11 [1998]). This device allows for high protein loading and rapid separations that require only four to six hours to perform. Proteins are harvested into liquid fractions after a 5-hour IEF separation. These liquid fractions are ready for analysis by NP RP HPLC. This device can be loaded with up to 1 g of protein.

b) Carrier Ampholyte Based Slab Gel IEF Separation with a Whole Gel Eluter

In this case the protein solution is loaded onto a slab gel and the proteins separate in to a series of gel-wide bands containing proteins of the same pI. These proteins are then harvested using a whole gel eluter (WGE, from Biorad). Proteins are then isolated in liquid fractions that are ready for analysis by NP RP HPLC. This type of gel can be loaded with up to 20 mg of protein.

c) IPG Slab Gel IEF Separation with a Whole Gel Eluter

Here the proteins are loaded onto a immobiline pI gradient slab gel and separated into a series of gel-wide bands containing proteins of the same pI. These proteins are electro-eluted using the WGE into liquid fractions that are ready for analysis by NP RP HPLC. The IPG gel can be loaded with at least 60 mg of protein.

2. Protein Separation by NP RP HPLC

Having obtained liquid fractions containing large amounts of pI-focused proteins, the second dimension separation is non-porous RP HPLC. The present invention provides the novel combination of employing non-porous RP packing materials (Eichrom) with another RP HPLC compatible detergent (e.g., n-octyl β-D-galactopyranoside) to facilitate the multi-phase separation of the present invention. This detergent is also compatible with mass spectrometry due to its low molecular weight. The use of these types of RP HPLC columns for protein separations as a second dimension separation after IEF in order to obtain a 2-D protein separation is a novel feature of the present invention. These columns are well suited to this task as the non-porous packing they contain provides optimal protein recovery and rapid efficient separations. It should be noted that though several detergents have been mentioned thus far for increasing protein solubility while being compatible with RP HPLC there are many other different low molecular weight non-ionic detergents that could be used for this purpose. Several important features that allow the RP HPLC to work as a second dimension are as follows: The mobile phase should contain a low level of a non-ionic low molecular weight detergent such as n-octyl β-D-glucopyranoside or n-octyl β-D-galactopyranoside as these detergents are compatible with RP HPLC and also with later mass spectrometry analyses (unlike many other detergents); the column should be held at a high temperature (around 60° C.); and the column should be packed with non-porous silica beads to eliminate problems of protein recovery associated with porous packings.

3. Protein Detection and Identification via Mass Spectrometry

In some embodiments of the present invention, the products of the second separation step are further characterized using mass spectrometry. For example, the proteins that elute from the NP RP HPLC separation are analyzed by mass spectrometry to determine their molecular weight and identity. For this purpose the proteins eluting from the separation can be analyzed simultaneously to determine molecular weight and identity. A fraction of the effluent is used to determine molecular weight by either MALDI-TOF-MS or ESI oa TOF (LCT, Micromass) (See e.g., U.S. Pat. No. 6,002,127). The remainder of the eluent is used to determine the identity of the proteins via digestion of the proteins and analysis of the peptide mass map fingerprints by either MALDI-TOF-MS or ESI oa TOF. The molecular weight 2-D protein map is matched to the appropriate digest fingerprint by correlating the molecular weight total ion chromatograms (TIC's) with the UV-chromatograms and by calculation of the various delay times involved. The UV-chromatograms are automatically labeled with the digest fingerprint fraction number. The resulting molecular weight and digest mass fingerprint data can then be used to search for the protein identity via web-based programs like MSFit (UCSF).

4. Automation

All of the above described steps are automated, for example, into one discrete instrument. In one illustrative embodiment, the first dimension is carried out by a Rotofor, with the harvested liquid fractions being directly applied to the second dimension non-porous RP HPLC apparatus through the appropriate tubing. The products from the second dimension separation are then scanned and the data interpreted and displayed as a 2-D representation using the appropriate computer hardware and software. Alternately, the products from the second dimension fractions are sent through the appropriate microtubing to a mass spectrometry pre-reaction chamber where the samples are treated with the appropriate enzymes to prepare them for mass spectrometry analysis. The samples are then analyzed by mass spectrometry and the resulting data is received and interpreted by a processor. The output data represents any number of desired analyses including, but not limited to, identity of the proteins, mass of the proteins, mass of peptides from protein digests, dimensional displays of the proteins based on any of the detected physical criteria (e.g. size, charge, hydrophobicity, etc.), and the like. In preferred embodiments, the proteins samples are solubilized in a buffer that is compatible with each of the separation and analysis units of the apparatus. Using the automated systems of the present invention provides a protein analysis system that is an order of magnitude less expensive than analogous automation technology for use with 2-D gels (See e.g., Figeys and Aebersold, J. Biomech. Eng. 121:7 [1999]; Yates, J. Mass Spectrom., 33:1 [1998]; and Pinto et al., Electrophoresis 21:181 [2000]).

5. Software and Data Presentation

The data generated by the above listed techniques may be presented as 2-D images much like the traditional 2-D gel image. In some embodiments, the chromatograms, TIC's or integrated and deconvoluted mass spectra are converted to ASCII format and then plotted vertically, using a 256 step gray scale, such that peaks are represented as darkened bands against a white background. The scale could also be in a color format. The image generated by this method provides information regarding the pI, hydrophobicity, molecular weight and relative abundance of the proteins separated. Thus the image represents a protein pattern that can be used to locate interesting changes in cellular protein profiles in terms of pI, hydrophobicity, molecular weight and relative abundance. Naturally the image can be adjusted to show a more detailed zoom of a particular region or the more abundant protein signals can be allowed to saturate thereby showing a clearer image of the less abundant proteins. This information can be used to assess the impact of disease state, pharmaceutical treatment, and environmental conditions. As the image is automatically digitized it may be readily stored and used to analyze the protein profile of the cells in question. Protein bands on the image can be hyper-linked to other experimental results, obtained via analysis of that band, such as peptide mass fingerprints and MSFit search results. Thus all information obtained about a given 2-D image, including detailed mass spectra, data analyses, and complementary experiments (e.g., immuno-affinity and peptide sequencing) can be accessed from the original image.

The data generated by the above-listed techniques may also be presented as a simple read-out. For example, when two or more samples are compared (See, Section J, below), the data presented may detail the difference or similarities between the samples (e.g., listing only the proteins that differ in identity or abundance between the samples). In this regard, when the differences between samples (e.g., a control sample and an experimental sample) are indicative of a given condition (e.g., cancer cell, toxin exposure, etc.), the read-out may simply indicate the presence or identity of the condition. In one embodiment, the read-out is a simple +/- indication of the presence of particular proteins or expression patterns associated with a specific condition that is to be analyzed.

6. IEF-NP RP HPLC in Operation

Figure 2:
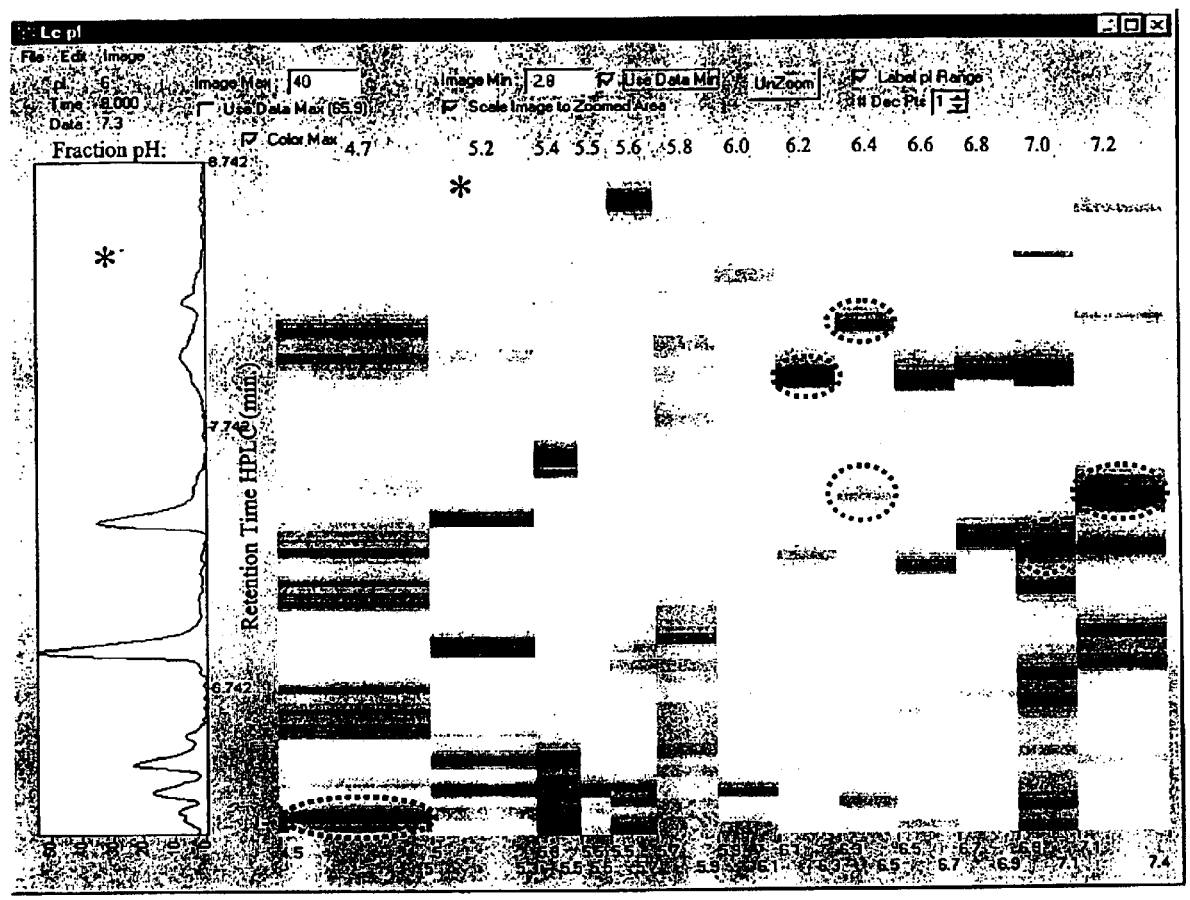
FIG. 2 shows a zoom area of a portion of the display in FIG. 1 (pI=4.2 to 7.2 and tR=6.0 to 9.0) (right panel showing banding patterns) and a corresponding example of linked HPLC data (left panel showing peaks).
Figure 3:
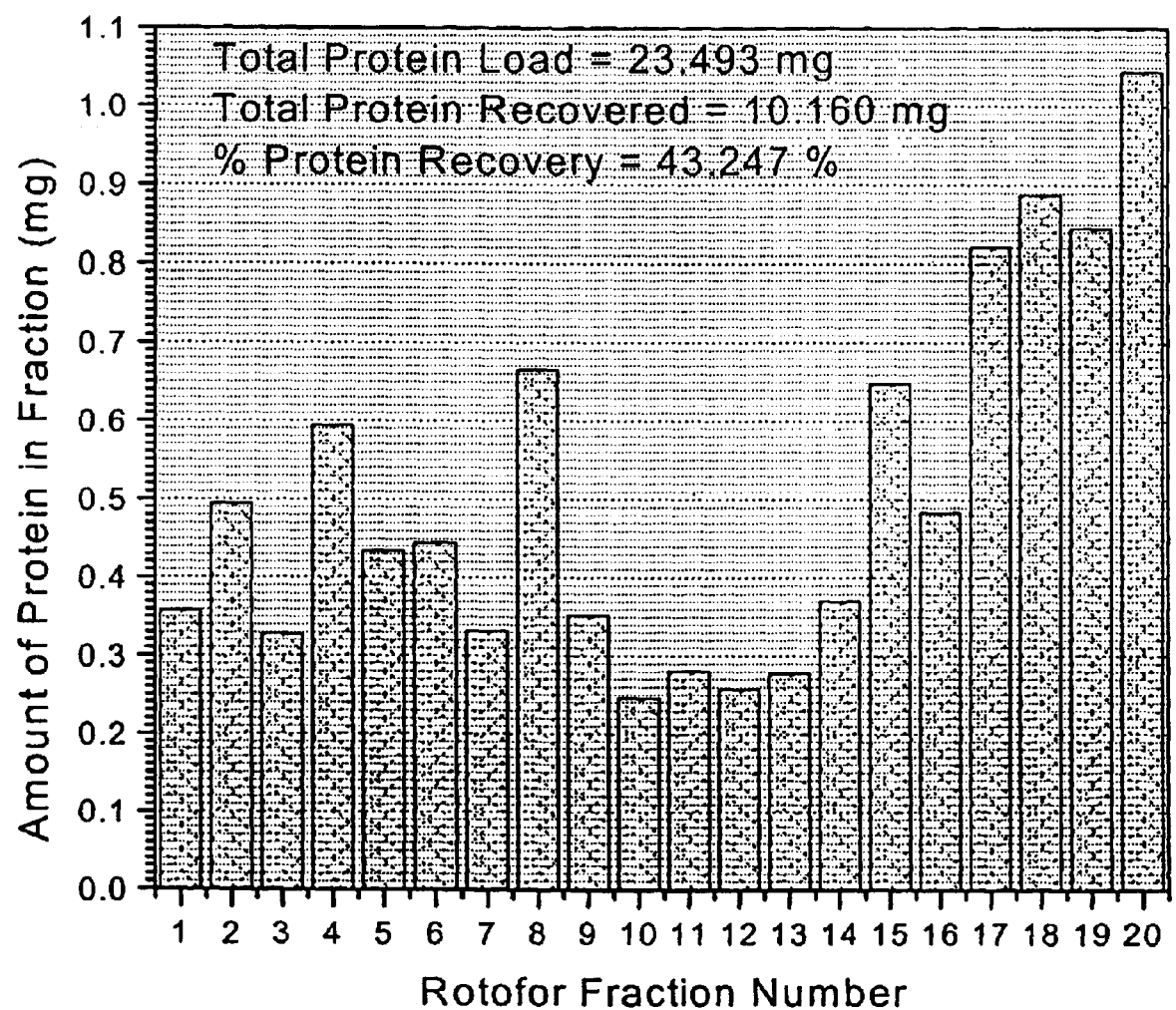
FIG. 3 shows a quantification of rotofor fractions in one embodiment of the present invention.
Figure 4:
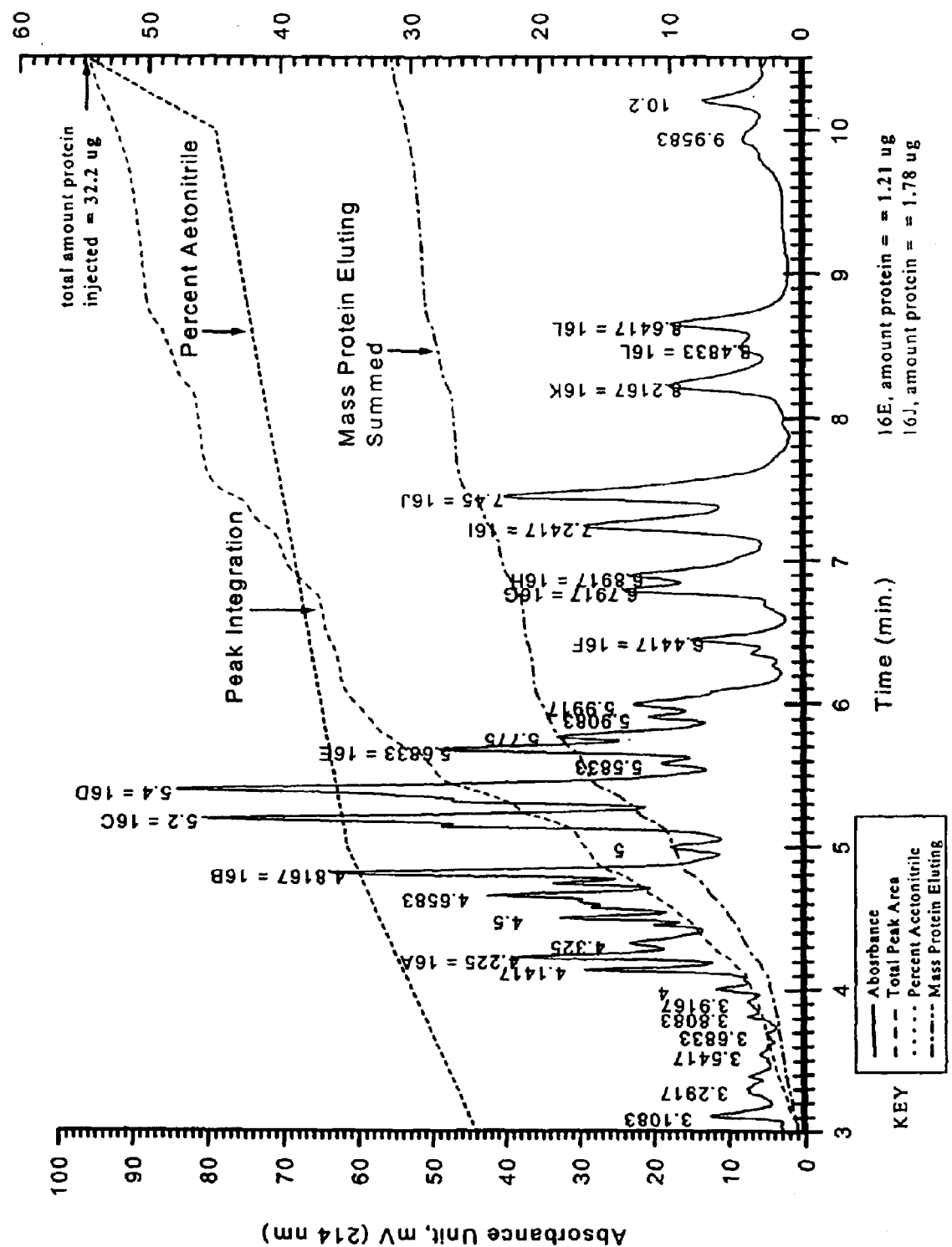
FIG. 4 shows NP RP HPLC separation from a Rotofor fraction of HEL cell lysate in one embodiment of the present invention.

The IEF-NP RP HPLC image shown in FIG. 1 is a digital representation of a 2-dimensional separation of a whole cell protein lysate from a human erythroleukemia (HEL) cell line. This image is designed to offer the same advantages of pattern recognition and protein profiling that may be obtained using a 2-D gel. The horizontal and vertical dimensions are in terms of isoelectric point and protein hydrophobicity, respectively. The isoelectric focusing step, performed using the Rotofor, resulted in 20 protein fractions ranging in pH from 3.2 to 9.5. These fractions were then injected onto a non-porous reversed phase column for separation by HPLC and detection by UV absorbance (214 nm). The resulting chromatograms were converted to ASCII format and then plotted vertically, using a 256 step gray scale, such that peaks are represented as darkened bands against a white background. Protein profiles may be viewed in greater detail by using the zoom feature as shown in FIG. 2 and/or by selecting a particular Rotofor fraction and observing the NP RP HPLC chromatogram as shown in the left panel of FIG. 2. The zoom and chromatogram image features provide a means to observe details in band patterns that may not be observable in the original image (See, FIG. 1). In addition, because of the limitations of the 256 step gray scale representation the band intensities in areas 1, 2 and 3 of FIG. 1 were rescaled by a factor of 3 to better show the low abundance proteins. This was preferred since the presence of several high abundance protein bands may cause low intensity bands in some regions to be undetected. In FIG. 1, the total peak area for each individual chromatogram was scaled to reflect the relative amount of protein that was found in the original Rotofor fraction (See, FIG. 3). The band intensities in different chromatograms can therefore be compared directly thus providing a true image of relative protein abundance in the cell lysate. The width of the Rotofor fraction columns was adjusted to represent their estimated pH range. The molecular weight of proteins observed by IEF-NP RP HPLC ranged from 12 kDa to 75 kDa. Typical NP RP HPLC separations, as shown in FIG. 4, resulted in 35 peaks in 10.5 minutes. The total number of peaks that could be observed from all 20 fractions is estimated to be approximately 700.

Figure 5:
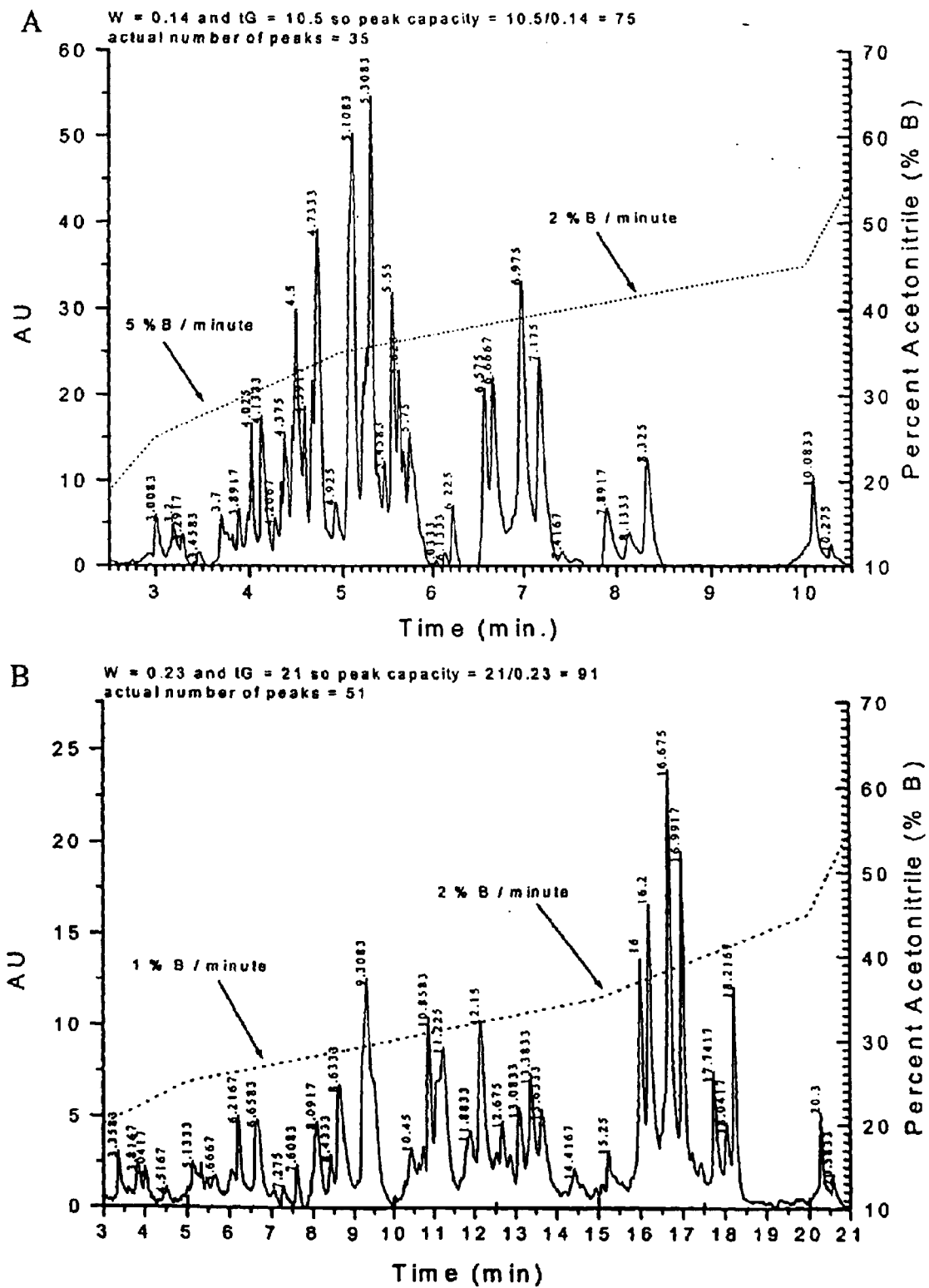
FIGS. 5A and 5B show short (5A) and long (5B) NP RP HPLC separation gradient times for a rotofor fraction of HEL cell lysate in one embodiment of the present invention.

The gradient time ($t_G$) used in the above experiments is very short and a significant increase in peak capacity is expected with longer gradients. This is shown using Rotofor fraction 17 where two separations were performed with gradient times of 10.5 minutes (See, FIG. 5A) and 21 minutes (See, FIG. 5B). With $t_G$=10.5 minutes, the average peak width was 0.14 minutes and the peak capacity was therefore 75. The actual number of peaks resolved was 35. With $t_G$=21 minutes the average peak width was 0.23 minutes and the peak capacity was therefore 91. The actual number of peaks resolved was 51. Using the longer separation time with $t_G$=21 minutes the total number of peaks observed should increase from 700 to 1000. However, it should be noted that when using mass spectrometric detection, that sufficient resolution should be available to ultimately resolve the same number of peaks without using a longer gradient time.

The proteins in a representative sampling of these peaks were identified using the traditional approach of enzymatic digestion, MALDI-TOF MS peptide mass analysis and MSFit database searching. The magnification of the IEF-NP RP HPLC image enables the viewer to perceive more bands than is possible to observe from the whole image. In addition, as shown in FIG. 2, the viewer may select a particular band format chromatogram and observe the traditional peak format of the chromatogram in a window to the left of the image. This allows the observer to use the peak format chromatogram to find partially resolved peaks that may not be observable in the band format chromatogram. Five standard protein bands are shown in the left-most column where the masses range from 14.2 kDa up to 67 kDa. As RP HPLC separates proteins by hydrophobicity, these standards are not molecular weight markers as in a traditional 1-D gel. Rather, they are used to indicate the range of protein molecular weights that may be observed. Ten different proteins are labeled on the image although many more proteins were identified as shown in Table 1, below. In some embodiments of the present invention, where it is desired that certain proteins or classes of proteins are to be detected, the starting protein sample may be selectively labeled. After the proteins are passed through the separation step, detection of the proteins can be limited to those that contain the selective label.

B. Protein Separation by 2-D SDS PAGE

Figure 6:
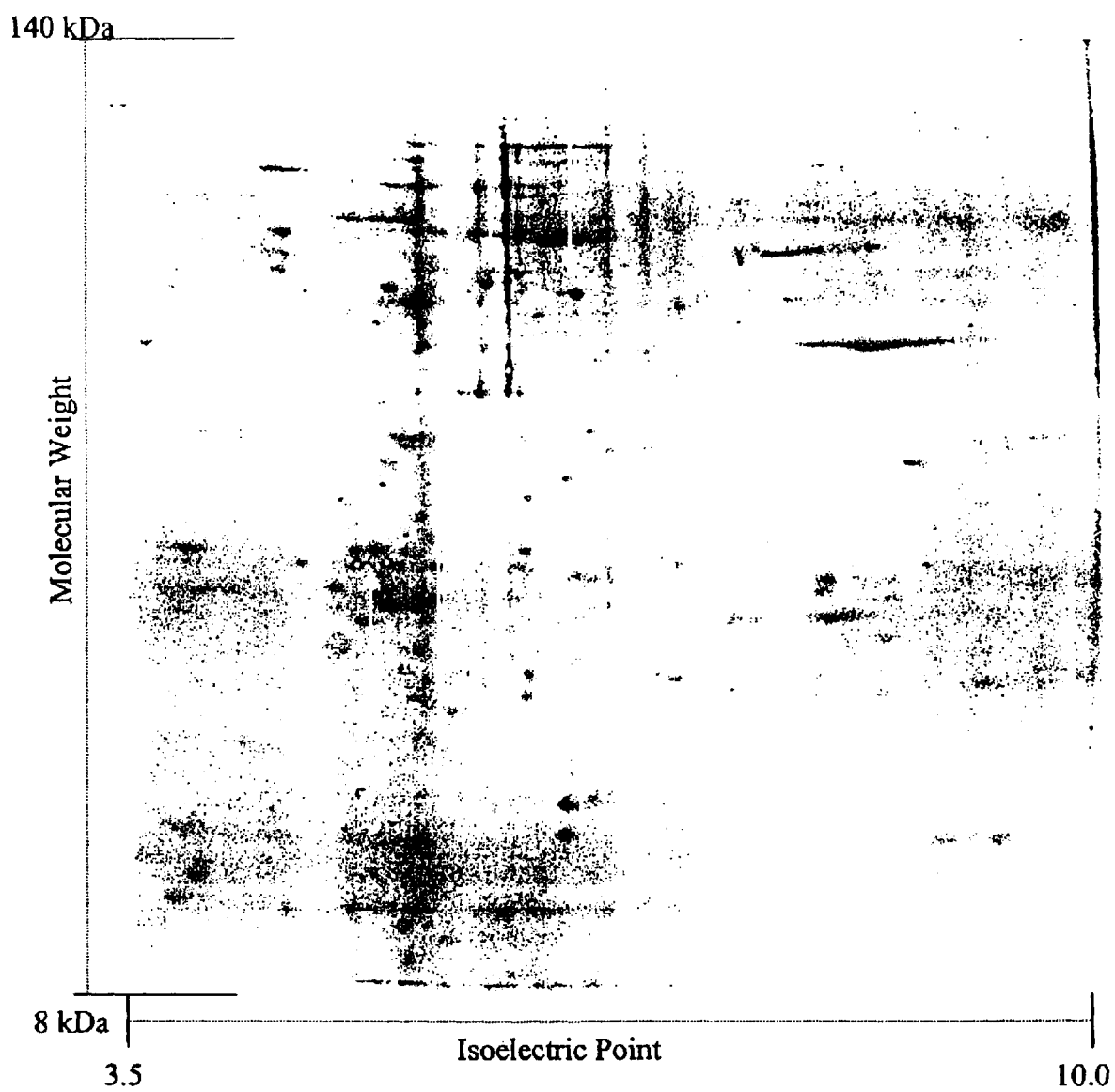
FIG. 6 shows an example of Coomassie blue stained 2-D PAGE separation of HEL cell lysate proteins.

The image in FIG. 1 represents the IEF-NP RP HPLC separation of the HEL cell protein lysate and the image in FIG. 6 represents the Coomassie blue (CBB) stained 2-D SDS PAGE separation of the same HEL cell line lysate. The pI range for this gel is the same as that used for the Rotofor separation and the molecular weight range is from 8 kDa to 140 kDa. As with the IEF-NP RP HPLC separation a representative sampling of the isolated proteins was identified using enzymatic digestion, MALDI-TOF MS and MSFit methods (See e.g., Rosenfeld et al., Anal. Biochem.

203:173 [1992]). For the target protein mass range of this study (10 kDa–70 kDa) approximately 188 protein spots are observed on the CBB stained gel, 355 from the CBB stained polyvinylidefle difluoride (PVDF) blot, and 652 from the silver stained gel as estimated using BioImage 2D Analyzer Version 6.1 software (Genomic Solutions). The total spot capacity for the 2-D gel separation is estimated to be 2100. The proteins identified from the gel are labeled on the image and also shown in Table 2, below. An image of another 2-D gel separation of HEL cell proteins can be observed via the Swiss-2DPAGE database (See e.g., the Internet world wide web site of the Swiss-2DPAGE database; Sanchez et al., Electrophoresis 16:1131 [1995]). In addition, it is possible to view the latest protein list for the HEL cell in which 19 protein entries are shown (See e.g., the Internet world wide web site of the Swiss-2DPAGE database).

TABLE 1

Thirty Eight Proteins Identified From HEL Cell IEF-NP RP HPLC Separation

| Rotofor Fraction # | pH | Retention Time (min.) | Enzyme* | MWt/pI: database calculated | Swiss, NCBInt Accession # | Protein Name |
|---|---|---|---|---|---|---|
| 3 | 4.20 | 5.34 | trypsin | 32575.2/4.64 | P06748 | NPM |
| 3 | 4.20 | 6.20 | trypsin | 11665.0/4.42 | P05387 | 60S RIBOSOMAL PROTEIN P2 |
| 3 | 4.20 | 6.91 | trypsin | 16837.7/4.09 | P02593 | CALMODULIN |
| 3 | 4.20 | 10.15 | trypsin | 41737.0/5.29 | P02570 | BETA-ACTIN & GAMMA ACTIN |
| 3 | 4.20 | 10.25 | trypsin | 61055.0/5.70 | P10809 | HSP-60 |
| 4 | 4.70 | 5.38 | trypsin | 32575.2/4.64 | P06748 | NPM |
| 4 | 4.70 | 6.24 | trypsin | 35994.6/6.61 | Q13011 | ENOYL-COA HYDRATASE |
| 4 | 4.70 | 7.07 | trypsin | 57914.2/7.95 | P14786 | PYRUVATE KINASE, M2 |
| 4 | 4.70 | 10.28 | trypsin | 61055.0/5.70 | P10809 | HSP-60 |
| 5 | 5.40 | 4.93 | trypsin | 22988.1/5.10 | P52566 | RHO GDI 2 |
| 5 | 5.40 | 10.15 | trypsin | 70898.4/5.38 | P11142 | HEAT SHOCK COGNATE 71 KD PROTEIN |
| 8 | 5.60 | 4.99 | trypsin | 22988.1/5.10 | P52566 | RHO GDP-DISSOCIATION INHIBITOR 2 |
| 8 | 5.60 | 7.94 | trypsin | 69224.5/5.49 | P23588 | EIF-4B |
| 8 | 5.60 | 10.35 | trypsin | 49831.3/4.79 | P05217 | TUBULIN BETA-2 CHAIN |
| 9 | 5.80 | 6.90 | trypsin | 56782.7/5.99 | P30101 | ERP60 |
| 9 | 5.80 | 8.05 | trypsin | 17148.8/5.83 | P15531 | METASTASIS INHIBITION FACTOR NM23 |
| 9 | 5.80 | 8.50 | trypsin | 26669.6/6.45 | P00938 | TRIOSEPHOSPHATE ISOMERASE (TIM) |
| 9 | 5.80 | 10.15 | trypsin | 41737.0/5.29 | P02570 | BETA-ACTIN & GAMMA ACTIN |
| 11 | 6.20 | 5.62 | trypsin | 36926.7/6.37 | 5542020 | (L32610) ribonucleoprotein |
| 11 | 6.20 | 7.65 | trypsin | 33777.2/6.26 | 4885153 | (X59656) CRKL |
| 11 | 6.20 | 7.91 | trypsin | 22327.3/7.83 | P04792 | HEAT SHOCK 27 |
| 11 | 6.20 | 8.80 | trypsin | 74674.0/8.51 | Q92935 | EXOSTOSIN-L |
| 11 | 6.20 | 9.22 | trypsin | 37374.9/5.85 | P19883 | FOLLISTATIN 1 AND 2 PRECURSOR |
| 11 | 6.20 | 10.40 | trypsin | 47033.1/5.30 | 5032183 | cargo selection protein TIP47 |
| 12 | 6.40 | 5.08 | trypsin | 13802.0/6.43 | P49773 | HINT |
| 12 | 6.40 | 5.90 | trypsin | 70021.3/5.56 | P54652 | HEAT SHOCK 70 KD PROTEIN 2 |
| 12 | 6.40 | 7.48 | trypsin | 47169.2/7.01 | P06733 | ALPHA ENOLASE |
| 12 | 6.40 | 8.12 | trypsin | 26669.6/6.45 | P00938 | TRIOSEPHOSPHATE ISOMERASE (TIM) |
| 13 | 6.60 | 4.88 | trypsin | 48058.0/5.34 | P05783 | KERATIN, TYPE 1 CYTOSKELETAL 18 |
| 13 | 6.60 | 8.28 | trypsin | 62639.6/6.40 | P31948 | TRANSFORMATION-SENSITIVE PROTEIN |
| 13 | 6.60 | 8.65 | trypsin | 34902.4/7.42 | 4505059 | carcinoma-associated antigen GA733-2 |
| 15 | 7.00 | 4.70 | trypsin | 37429.9/8.97 | P22626 | NUCLEAR RIBONUCLEOPROTEINS A2/B1 |
| 15 | 7.00 | 8.70 | trypsin | 22391.6/8.41 | P37802 | SM22-ALPA HOMOLOG |
| 15 | 7.00 | 7.25 | trypsin | 47169.2/7.01 | P06733 | ALPHA ENOLASE |
| 16 | 7.20 | 5.68 | trypsin, Glu-C(E) | 18012.6/7.68 | P05097 | PPIASE |
| 16 | 7.20 | 6.89 | trypsin | 35940.7/7.18 | P01861 | IG GAMMA-4 CHAIN C REGION |
| 16 | 7.20 | 7.24 | trypsin | 36053.4/8.57 | P04406 | GLYCERALDEHYDE 3-PHOSPHATE |
| 16 | 7.20 | 7.45 | trypsin, Glu-C(E) | 47169.2/7.01 | P06733 | ALPHA ENOLASE |
| 16 | 7.20 | 8.64 | trypsin, Glu-C(E) | 22391.6/8.41 | P37802 | SM22-ALPHA HOMOLOG |
| 19 | 9.00 | 4.88 | trypsin | 38846.0/9.26 | P09651 | NUCLEAR RIBONUCLEOPROTEIN A1 |
| 19 | 9.00 | 5.13 | trypsin | 37429.9/8.97 | P22626 | NUCLEAR RIBONUCLEOPROTEINS A2/B1 |
| 19 | 9.00 | 5.85 | trypsin | 46987.1/7.58 | P13929 | BETA ENOLASE |
| 19 | 9.00 | 7.47 | trypsin | 36053.4/8.57 | P04406 | GLYCERALDEHYDE 3-PHOSPHATE |
| 19 | 9.00 | 8.70 | trypsin | 38604.2/7.58 | P07355 | ANNEXIN II |
| 19 | 9.00 | 9.07 | trypsin | 22391.6/8.41 | P37802 | SM22-ALPHA HOMOLOG |
| 19 | 9.00 | 10.53 | trypsin | 57211.6/9.22 | P26599 | PTB. NUCLEAR RIBONUCLEOPROTEIN I |
| 20 | 9.50 | 4.46 | trypsin, Glu-C(E) | 38846.0/9.26 | P09651 | NUCLEAR RIBONUCLEOPROTEIN A1 |
| 20 | 9.50 | 4.67 | trypsin, Glu-C(E) | 37429.9/8.97 | P22626 | NUCLEAR RIBONUCLEOPROTEINS A2/B1 |
| 20 | 9.50 | 6.72 | trypsin, Glu-C(E) | 39420.1/8.30 | P04075 | FRUCTOSE-BISPHOSPHATE ALDOLASE A |
| 20 | 9.50 | 7.06 | trypsin | 36053.4/8.57 | P04406 | GLYCERALDEHYDE 3-PHOSPHATE |
| 20 | 9.50 | 7.39 | trypsin, Glu-C(E) | 47169.2/7.01 | P06733 | ALPHA EMOLASE |
| 20 | 9.50 | 8.52 | trypsin, Glu-C(E) | 22391.6/8.41 | P37802 | SM22-ALPHA HOMOLOG |
| 20 | 9.50 | 10.16 | trypsin | 44728.1/8.30 | P00558 | PHOSPHOGLYCERATE KINASE 1 |
| 20 | 9.50 | 10.35 | trypsin | 57211.6/9.22 | P26599 | PTB, NUCLEAR RIBONUCLEOPROTEIN I |

*Note that all proteins labelled only with trypsin were not digested with Glu-C(E)

TABLE 2

Nine Proteins Identified From HEL Cell CBB 2-D Gel

| Gel Spot I.D. Number | Enzyme | MWt/pI: database calculated | SwissProt Accession # | Protein Name |
|---|---|---|---|---|
| g1 | trypsin | 18012.6/7.68 | P05092 | PPIASE |
| g2 | trypsin | 26669.6/6.45 | P00938 | TRIOSEPHOSPHATE ISOMERASE (TIM) |
| g3 | trypsin | 26669.6/6.45 | P00938 | TRIOSEPHOSPHATE ISOMERASE (TIM) |
| g8 | trypsin | 29032.8/4.75 | P12324 | TROPOMYOSIN, CYTOSKELETAL TYPE (TM30-NM) |
| g10 | trypsin | 32575.2/4.64 | P06748 | NPM |
| g11 | trypsin | 41737.0/5.29 | P02570 | BETA-ACTIN |
| g12 | trypsin | 61055.0/5.70 | P10809 | HSP-60 |
| g13 | trypsin | 56782.7/5.99 | P30101 | ERP60 |
| g14 | trypsin | 47169.2/7.01 | P06733 | ALPHA ENOLASE |

C. IEF-NP RP HPLC versus 2-D SDS PAGE: Protein Loading and Quantification

Each separation method relies upon orthogonal mechanisms of separation generating a large number of isolated proteins. Protein profiles may be compared in terms of their pattern as well as the relative amounts of isolated proteins. It is shown, however, that the loadability of the liquid phase methods of the present invention greatly surpasses that of the gel phase.

The limit of detection for the gel method when stained with the silver stain is approximately 1 to 10 ng. The Coomassie blue stain can detect 100 ng of protein and the amount of protein in the spot can be quantified over 2.5 orders of magnitude. For the NP RP HPLC of standard proteins used in certain embodiments of the methods of the present invention, the limit of detection for the UV detector was 10 ng. The protein in the peak can be quantified from 10 ng up to 20 µg providing 3.1 orders of magnitude. Quantification of an HPLC peak involves integrating the peak to find the area. For the gel, the spots must first be digitized and then this image must be analyzed to determine the integrated optical density of each spot of interest. The sensitivity of the UV detector in embodiments of the present invention utilizing HPLC is competitive with the silver stain and quantification is much simpler. The limits of detection for both the silver stained gel and the HPLC UV peak detection are mass dependent. For the gel, resolution and sensitivity are proportional to the molecular weight of the protein. For IEF-NP RP HPLC, the resolution and sensitivity are inversely proportional to the molecular weight of the protein. The gel appears to provide improved results for both acidic proteins and proteins above 50 kDa whereas IEF-NP RP HPLC performs better with proteins in the basic region and proteins that are below 50 kDa (See e.g., FIG. 1 and FIG. 6). These results show the complementary nature of these two techniques where the gel and IEF-NP RP HPLC each provide important information of protein content.

In one experiment using the methods of the present invention, 23.5 mg of protein was loaded into the Rotofor, and after a five-hour IEF separation period fractions ranging from 2 to 4 mL were collected into polypropylene microtubes. The amount of protein in the individual fractions ranged from 0.25 mg to 1.05 mg. Summing the amounts of protein in each fraction led to the determination that a total of 10.2 mg of protein was recovered from the Rotofor. This amount can be increased by increasing the amount of non-ionic detergent in the Rotofor buffer above the current 0.1% level as well as by the addition of thiourea. In contrast, the amount of protein loaded on the 2-D gel in FIG. 6 is 200 µg. The amount of protein that actually makes it through the gel and focuses to a spot has not been quantified, relative to the amount of protein that is actually loaded on the gel, though it is known that many hydrophobic proteins are lost during the separation (Herbert, Electrophoresis 20:660 [1999]). The amount of protein that may theoretically be loaded on a gel ranges from 5 µg up to 250 µg whereas for IEF-NP RP HPLC the initial loading of protein may be as high as 1 gram. The amount of protein actually used to produce the separation shown in FIG. 1 is only a fraction of the amount initially loaded into the Rotofor. The image in FIG. 1 actually represents the separation of a total of 1 to 2 mg of protein though 10.2 mg of protein was recovered from the Rotofor. The loading of the HPLC column being used currently could be increased though the peak capacity may suffer. Alternatively a larger column could be used in series with the smaller column to allow for higher loadability with no loss of separation efficiency (See e.g., Wall et al., Anal. Chem., 71:3894 [1999]).

A 2-D gel provides a two dimensional separation from one initial loading of the cell lysate. The intensities of different spots on the same gel are representative of the relative protein abundances in the original lysate. However, in the IEF-NP RP HPLC methods of the present invention the proteins are loaded for the IEF and the HPLC separations so that the band intensities in the 2-D IEF-NP RP HPLC image depend on the amount of protein loaded to the HPLC from each Rotofor fraction. Since the amount of material in each Rotofor fraction is different, the total area of each chromatogram was scaled to represent the total amount of protein that was recovered for each Rotofor fraction (See, FIG. 3). The result is that the protein band intensities can be compared both within the Rotofor fraction and between the different fractions.

In some embodiments of the present invention, 2-D gel techniques are used side-by-side with IEF-NP RP HPLC. In embodiments where specific proteins are desired for further characterization, the gel can provide information indicating which fraction obtained with IEF-NP RP HPLC contains the desired protein or proteins.

D. Isoelectric Focusing: Liquid vs. Gel Phase

The principal concern with liquid phase IEF is that the protein is not isoelectrically focused as effectively as it would be in a gel due to diffusion of the protein in solution. In the case of α-enolase, if one compares the liquid and gel phase images, it can be seen that in both cases substantial spreading of the protein occurs over a wide pI range. This range spans from pI 6.5 to pI 9.5 in both the liquid phase and the gel phase. For more acidic proteins such as β-actin, it appears that in the liquid phase the protein is more dispersed in the pI dimension than for the corresponding gel separated protein. Both methods provide a reasonably accurate assessment of the pI of the protein of interest. Referring to Table 1, it can be seen that as the Rotofor fraction pH increases, so generally does the pI of identified proteins therein. The pH of fraction 3 measures 4.2 and the proteins identified from this fraction range in pI from 4.09 to 5.7. The pH of fraction 9 was 5.8 and the proteins identified from that fraction ranged from 5.29 to 6.45. The pH of fraction 16 was 7.2 and the pI range of proteins found there ranged from 7.01 to 8.93. The pI accuracy therefore ranges from +/−0.65 to 1.73 pI units. This is comparable to the carrier ampholyte based gel. It should be remembered that the pI of a given protein may vary significantly due to post-translational modifications such as phosphorylation and glycosylation, as well as to artifactual modifications such as carbamylation and oxidation.

E. Second Dimension Liquid Separation

Fraction 16, FIG. 4, may be used as an example of the quantification of isolated proteins. For fraction 16, the volume of injection was 160 μL. This means that if the concentration of protein was 201.4 μg/mL then the amount of protein loaded was 32.2 μg. The chromatogram was integrated using Microcal Origin software and the total area was determined to be 97.78. The areas of peaks 16E and 16J were 3.68 and 5.41 respectively. Dividing the peak area by the total area gives the fraction of protein represented by the peak. Therefore, if one assumes 100% protein recovery, the amount of PPIASE (16E, $t_R$=5.68) in 16 was (0.0376*32.2 μg) 1.21 μg and the amount of α-enolase (16J, $t_R$=7.45) was (0.0553*32.3 μg) 1.78 μg. The peak areas were generated by absorbance of 214 nm light at the amide bonds of the proteins and so should offer low selectivity thereby allowing for a good measure of the amount of protein in the peak regardless of the type of protein.

FIG. 4 shows how the continuous integration of the chromatogram may be used to estimate the amount of protein isolated in a given peak. The peak area line is simply converted into mass units from which the observer can measure the change in the vertical mass axis that occurs over the width of the peak of interest. If one knows the initial concentration of protein in the cell lysate and the number of cells that were lysed, a quantitative comparison of different cell lysates can be made. This comparison is important to studying changes in protein expression levels due to some disease state or pharmacological treatment. In gel work, a technique used for protein quantification in different samples is to normalize the integrated optical density of the spot of interest to that of standard proteins whose expression levels are thought to be constant. In this way any experimental variation in spot intensity can be corrected. This same method is applied to the IEF-NP RP HPLC image to allow for reliable quantification of proteins of interest such that changes in expression level are quantitatively observed.

The assumption in these experiments is 100% protein recovery. One can determine the actual % recovery of protein and the dependence on elution time. Typical protein recoveries have been shown to range from 70 to 95% in NP RP HPLC (Wall et al., Anal. Chem., 71:3894 [1999]) and so, with a more likely percent recovery of 80%, the amount of PPIASE and α-enolase in fraction 16 would be estimated to be 1.0 μg and 1.42 μg, respectively.

F. Rotofor Fraction Analysis by NP RP HPLC vs. 1-D SDS PAGE

Figure 7:
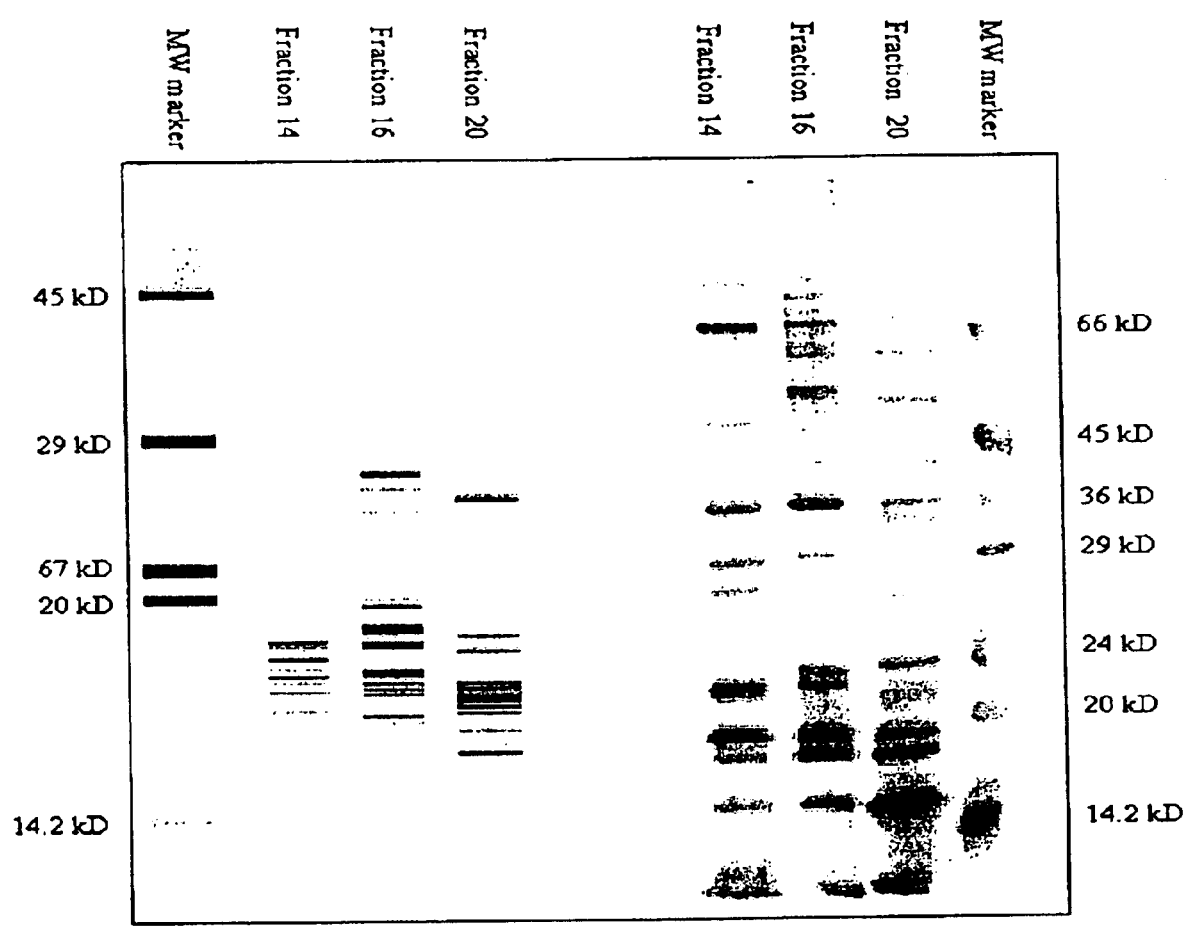
FIG. 7 shows a direct side-by-side comparison of IEF-NP RP HPLC (four lanes on the left) with 1-D SDS PAGE (four lane on the right) for several Rotofor fractions in certain embodiments of the present invention.

NP RP HPLC provides highly efficient protein separations (See e.g., Chen et al., Rap. Comm. Mass Spec., 12:1994 [1998]; Wall et al., Anal. Chem., 71:3894 [1999]; and Chong et al., Rap. Comm. Mass Spec., 13:1808 [1999]), and is a far easier method to automate as compared to gels in terms of injection, data processing and protein collection. In addition the NP RP HPLC separations provided by the present invention are 70 times faster than the equivalent separation by 1-D SDS-PAGE, which requires 14 hours. In the experiments described above, the NP RP HPLC method has greater resolving power generating 35 bands where the 1-D gel generates only 26 bands. A direct comparison of the two methods, as shown in FIG. 7, reveals that the NP RP HPLC bands are much narrower than those of the 1-D SDS PAGE over a similar molecular weight range. Also it is clear that as molecular weight decreases, the 1-D gel band width increases substantially. In NP RP HPLC the opposite trend occurs where the lower molecular weight proteins show improved resolution and sensitivity. This image may appear to show that the NP RP HPLC separation fails with larger proteins as there are few bands in the upper region of the image. However, this is not the case as it is important to remember that the vertical dimension for NP RP HPLC is not protein molecular weight but rather protein hydrophobicity. This is evidenced by the observation of the elution of bovine serum albumin (66 kDa), a relatively hydrophilic protein, half way up an image.

G. Elution Time Prediction for Known Target Protein

One of the advantages of the 2-D gel is that the vertical coordinate of the gel may be used to estimate the molecular weight of the protein with a +/-10% error. The position of a protein of interest can therefore be estimated before the protein is identified from the gel. In an attempt to correlate elution time in the methods of the present invention with the mass of the protein, a linear fit to a plot of percent acetonitrile at time of elution (% B) versus the log(MWt)/protein polar ratio was generated. The polar ratio (PR) is the number of polar amino acids divided by the total number of amino acids in the protein and the molecular weight is in kDa. The proteins used for this plot were four of the standards listed in FIG. 1 as well as a sampling of six of the proteins from Table 1 (HSP60, β-actin, TIM, α-enolase, PPIASE and glyceraldehyde-3-phosphate). The resulting equation (equation 1: % B/100=0.079805*(logMWt)/PR+0.077686, (R=0.9677, SD=0.014722, N=7)) is used to predict the elution time of target proteins. For HSP60, β-actin and α-enolase the experimental elution times were 10.28, 10.15 and 7.25 respectively. The predicted elution times were 10.20, 10.13 and 9.78. In the cases of HSP60 and β-actin the prediction works well, whereas for α-enolase the prediction is not as good. While not precise, this prediction does give some idea of when a protein will elute such that a given target protein, for which the molecular weight and hydrophobicity are known, can be found more readily.

H. Protein Identification by Enzymatic Digestion, MALDI-TOF MS and MSFit Database Searching The proteins that were identified from a representative sampling of the bands from the IEF-NP RP HPLC separation are listed in Table 1. A sampling of approximately 80 proteins from 12 of the Rotofor fractions were digested and their peptide mass maps successfully obtained by MALDI-TOF MS. Of these 80, 38 different proteins were identified. In this case, identifying roughly 50% of the proteins searched is to be expected as not all the proteins are in the available databases. Similar results were observed for proteins analyzed from 2-D gels of the HEL cell samples. The current table in Swiss-2DPAGE lists 19 protein entries for the HEL cell. Of these 19 proteins, five were identified from the IEF-NP RP HPLC separation. In the gel, these same five proteins were also identified.

Figure 8A:
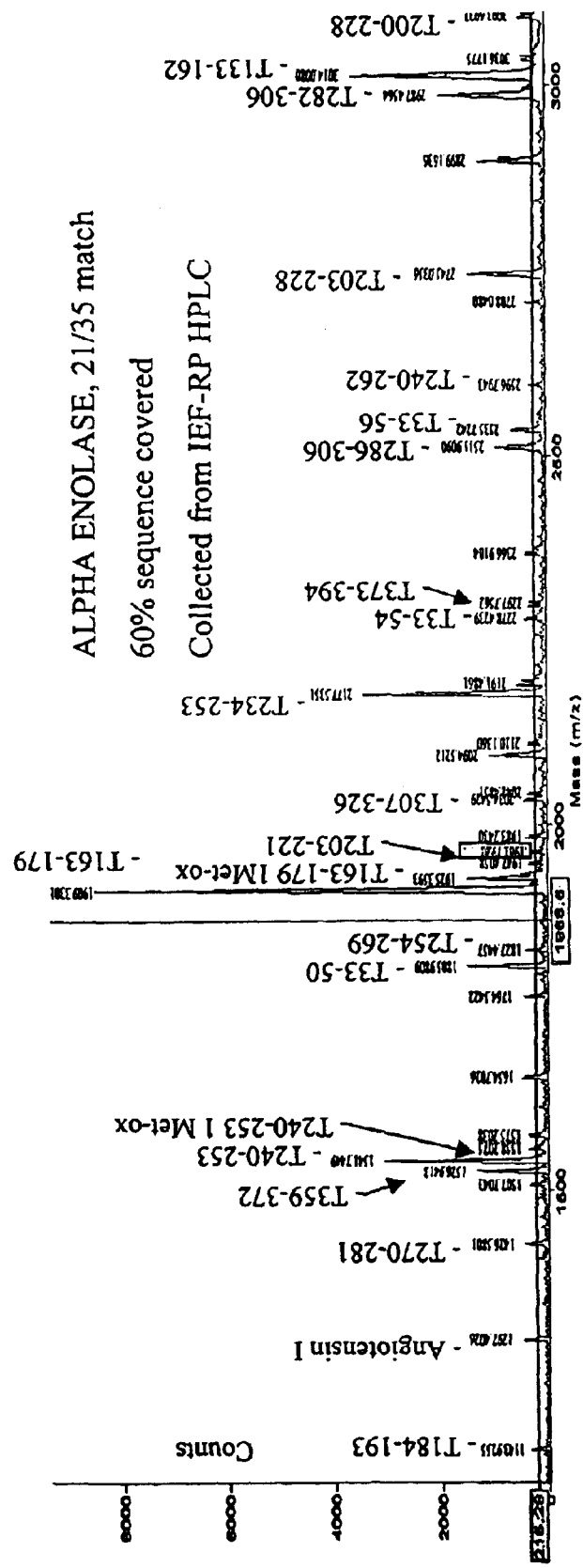
FIGS. 8A and 8B show MALDI-TOF MS tryptic peptide mass maps for α-enolase isolated by IEF-NP RP HPLC (8A) and by 2-D PAGE (8B).
Figure 8B:
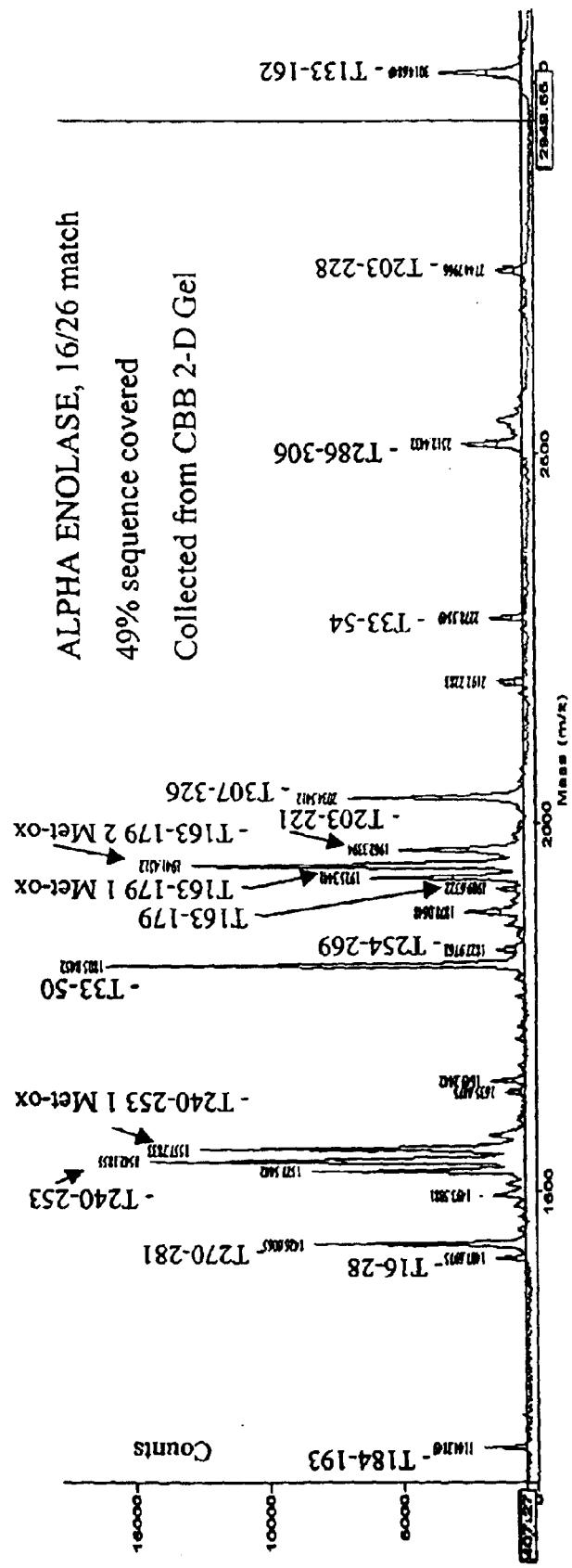

In general, it appears that the gel MSFit results are better than those from the liquid phase. This can be attributed to the fact that the gel proteins were reduced and alkylated with DTE and iodoacetamide respectively prior to the running of the second dimension. This step would help insure that all disulfide bonds are broken and optimal proteolysis is produced. Thus, this derivatization step can be added to the IEF-NP RP HPLC method, by performing the reduction and alkylation step prior to NP RP HPLC or during cell lysis. Nevertheless, in some cases the IEF-NP RP HPLC digestions surpassed those from the gel in coverage and quality. This is evidenced in FIG. 8, which shows a direct comparison of the MALDI-TOF MS for α-enolase as isolated via the IEF-NP RP HPLC method and the gel method. These mass spectra were calibrated externally at first and the mass profiles used to search the Swiss protein database with a mass accuracy of 400 ppm. These searches gave strong hits to α-enolase for both the gel and the liquid protein digests. Each mass spectrum was then recalibrated internally using matched peptide peaks from the initial externally calibrated match. The new peak table was then used to search the same Swiss protein database but with 200 ppm mass accuracy. FIG. 8 clearly shows that the digestion from the liquid phase is improved compared to that from the gel. The IEF-NP RP HPLC mass spectrum matches to 60% of the protein sequence whereas that from the gel matches to 49%. Achieving a match to 60% of the sequence of a 47 kDa protein is very unusual for MALDI-TOF MS analysis and represents a significant improvement over gel digests. Although the present invention is not limited to any particular mechanism, the increase in sequence coverage may be due to the fact that the protein is digested in the liquid phase, is relatively pure, and because the peptides are not lost due to being embedded inside the gel piece. Also if one observes the level of methionine oxidation in the peak that matches to T163–179, it is clear that the protein isolated by IEF-NP RP HPLC is far less oxidized than that from the gel.

Many of the NP RP HPLC chromatograms contain some peaks that are not fully resolved to baseline. This need not be a problem as partially resolved proteins can still be effectively identified using MALDI-TOF MS analysis. In Rotofor fraction 3 there are peaks at 10.15 minutes and 10.25 minutes (See, Table 1). These peaks are only resolved to 50% above the baseline and yet it is clear that the peak eluting at 10.15 minutes is β-actin and the peak eluting at 10.25 minutes is HSP-60. Note that the predicted elution times for these proteins are 10.13 and 10.20 minutes respectively. As proteins can be identified from partially resolved peaks, faster separations with more rapid gradients are possible. The reproducibility of the pattern of bands can be determined by looking at the retention times for particular proteins as observed from different Rotofor fractions. β-actin elutes at 10.15 minutes in both fractions 3 and 9; α-enolase elutes at 7.25, 7.45 and 7.39 minutes in fractions 12, 16 and 20 respectively; and HSP-60 elutes at 10.28 and 10.25 minutes in fractions 3 and 4 respectively. Clearly, with +/−0.1 minutes variation in the retention times, these separations are quite reproducible from run to run.

Thus, the methods of the present invention have been shown to provide advantageous methods for the reproducible separation of large numbers of proteins. In the human erythroleukemia cell lysate example, the methods are capable of resolving 700 bands with a rapid gradient, and 1000 bands with a longer gradient. There were 38 different proteins tentatively identified, by MALDI-TOF MS and MSFit database searching, after analysis of a fraction of these bands. This compares favorably with the 19 different proteins that have been identified to date from the 2-D gel. Some of the proteins found in the human erythroleukemia cell lysate; including α-enolase (Rasmussen et al., Electrophoresis 19:818 [1998] and Mohammad et al., Enz. Prot., 48:37 [1994]), glyceraldehyde-3-phosphate dehydrogenase (Bini et al., Electrophoresis 18:2832 [1997] and Sirover, Biochim. Biophys. Acta 1432:159 [1999]), NPM (Redner et al., Blood 87:882 [1996]), CRKL (ten Hoeve et al., Oncogene 8:2469 [1993]), and heat shock protein (HS27)(Fuqua et al., Cancer Research 49:4126 [1989]), have been linked to various forms of cancer. NPM and CRKL have been linked specifically to leukemias.

The proteins identified in one exemplary experiment ranged from 12 kDa up to 75 kDa (although broader ranges are contemplated by the present invention); this range may include many of the proteins of interest to current research involving protein profiling, identification and correlation to some disease state or cell treatment. In sharp contrast to 2-D gels, this method is well-suited to automation. Mass spectrometric methods can be applied, such as ESI-MS and MALDI-TOF MS, to the detection of whole proteins and protein digests. Most importantly, the methods of the present invention provide an alternative 2-D protein map to the traditional 2-D gel and appears to improve results for lower mass proteins and more basic proteins. A key advantage of the liquid 2-D separation is that the end product is a purified protein in the liquid phase. Also, since the initial protein load can be fifty times that of the gel, the amount of a target protein that may be isolated by one IEF-NP RP HPLC separation is potentially fifty times higher than that obtainable from a 2-D gel separation. Additionally, in the case that the investigator is interested in specific proteins where the pI is known, this method may be used to isolate and identify the target protein in less than 24 hours, since only the fraction of interest need be analyzed via the second dimension separation. The gel-based method would require three days to achieve the same result.

I. Identification of Novel Tumor Antigens

There is substantial interest in identifying tumor proteins that are immunogenic. Autoantibodies to tumor antigens and the antigens themselves represent two types of cancer markers that can be assayed in patient serum and other biological fluids. IEF-NP RP HPLC-MS has been implemented for the identification of tumor proteins that elicit a humoral response in patients with cancers. The identification of proteins that specifically react with sera from cancer patients was demonstrated using this approach. Solubilized proteins from a tumoral cell line are subjected to IEF-NP RP HPLC-MS. Individual fractions defined on the basis of pI range are subjected simultaneously to one-dimensional electrophoresis as well as to HPLC. Sera from cancer patients are reacted with Western blots of one-dimensional electrophoresis fractions. One band which reacted specifically with sera from lung cancer patients and not from controls was found to contain both Annexin II and aldoketoreductase. The ability to subfractionate further proteins contained in this fraction by HPLC led to the identification of Annexin II as the tumor antigen that elicited a humoral response in lung cancer patients.

J. Comparative Analysis

As is clear from the above description, the methods of the present invention offer the opportunity to compare protein profiles between two or more samples (e.g., cancer vs. control cells, undifferentiated vs. differentiated cells, treated vs. untreated cells). In one embodiment of the present invention, the two samples to be compared are run in parallel. The data generated from each of the samples is compared to determine differences in protein expression between the samples. The profile for any given cell type may be used as a standard for determining the identity of future unknown samples. Additionally, one or more proteins of interest in the expression pattern may be further characterized (e.g. to determine its identity). In an alternative embodiment, the proteins from the samples are run simultaneously. In these embodiments, the proteins from each sample are separately labeled so that, during the analysis stage, the protein expression patterns from each sample are distinguished and displayed. The use of selective labeling can also be used to analyze subsets of the total protein population, as desired.

As is clear from the above description, the methods and compositions of the present invention provide a range of novel features that provide improved methods for analyzing protein expression patterns. For example, the present invention provides methods that combine IEF, resulting in pI-focused proteins in liquid phase fractions, with nonporous RP HPLC to produce 2-dimensional liquid phase protein maps. The data generated from such methods may be displayed in novel and useful formats such as viewing a collection of different pI NP RP HPLC chromatograms in one 2-D image displaying the chromatograms in a top view protein band format, not the traditional side view peak format. As shown in FIG. 2, the side view peak format is shown to the left and the top view band format is shown to the right. The present invention also provides detergents that are compatible with automated systems employing multi-phase separation and detection steps.

The present invention provides additional characterization steps, including the identification of proteins separated by IEF-NP RP HPLC using enzymatic digestions and mass spectrometric analysis of the resulting peptide mass fingerprints. Proteins may be detected to determine their molecular weights by analyzing the effluent from the HPLC with either off-line collection to a MALDI plate (Perseptive) or on-line analysis using orthogonal extraction time-of-flight. The data generated from such methods may be displayed in novel and useful formats such as using the data from the MALDI or LCT generated protein molecular weights to generate total ion chromatograms (TIC) that would be virtually identical to the original UV-absorbance chromatograms. The signal of these chromatograms would be based on the number of ions generated from the HPLC effluent of a given group of pI-focused proteins, not by absorption of light. These chromatograms are plotted in the same 2-D top view band format as mentioned above. These methods allow one to fully integrate and deconvolute each of the TIC's generated to display complete mass spectra of each collection of pI-focused proteins. The methods also allow the display of all the integrated TIC's in one 2-D image where the vertical dimension is in terms of protein molecular weight and the horizontal dimension is in terms of protein pI. The protein mass spectra appears as bands as they are also viewed from the top. This image would therefore also contain quantitative information (in the case of the LCT) and so the bands would vary in intensity depending on the amount of protein present.

The liquid phase methods for protein mass mapping would also allow for collection of protein fractions to microtubes such that the proteins could be digested and the peptide mass maps analyzed to determine the identity of said proteins simultaneously. Laser induced fluorescence (LIF) detection schemes are used in conjunction with this method to increase the overall sensitivity by three orders of magnitude. The liquid phase LIF detector provides more sensitive fluorescence detection than in the gel as there would be no gel background fluorescence. This LIF detection method could be used in a number of ways including, but not limited to:

1) Combining equal amounts of two cell lysates that have each been previously stained with a different fluorescent dye followed by use of a dual fluorescence detector to simultaneously detect the same proteins from two different cell lysates. This would allow for very accurate comparisons of the relative amounts of proteins found for different cell lines or tissues; and 2) Using a fluorescently tagged antibody to label specific target proteins in a cell lysate such that they can be targeted for thorough analysis without looking at all the other proteins.

The methods and apparatuses of the present invention also offer an efficient system for combining with other analysis techniques to obtain a thorough characterization of a given cell, tissue, or the like. For example, the methods of the present invention may be used in conjunction with genetic profiling technologies (e.g., gene chip or hybridization based nucleic acid diagnostics) to provide a fuller understanding of the genes present in a sample, the expression level of the genes, and the presence of protein (e.g., active protein) associated with the sample.

II) Improved Elution Techniques Using Chromatofocusing

As described above, the present invention provides novel liquid chromatographic methods involving a 2-column 2-D separation of proteins from whole cell lysates followed by on-line mass mapping with by mass spectrometry (e.g., using ESI-oaTOF MS as described in detail below). It is a 3-D protein analysis system as proteins are separated based upon, for example, their isoelectric points (pI) in the first LC dimension.

The present invention further provides novel techniques for eluting proteins from a separation apparatus (e.g., the first phase separation apparatus). For example, in one embodiment of this technique, the proteins eluted from the first dimension are "peeled off" from the column according to their pH, either one pH unit or fraction thereof, at a time—referred to as chromatofocusing (CF). These focused liquid fractions are then separated according to their hydrophobicity and size (or other desired properties) in the second dimension. Liquid fractions from, for example, NP-RP-HPLC can be conveniently analyzed directly on-line using mass spectrometry (e.g., ESI-oaTOF) to obtain their molecular weight and relative abundance, which provides a third dimension. As a result, a virtual 2-D protein image is created and is analogous to a 2-D gel image. Furthermore, this 2-D protein image includes vital information such as the pI, hydrophobicity, molecular weight, and relative abundance. This "Protein Peeling" 2-D LC-MS method is a practical alternative to 2-D gels in order to study protein expression between normal and disease whole cell lysates, for example. This whole system can be fully automated and integrated into a single unit for rapid proteome analysis, providing a more accurate and less expensive automation technology compared to automation technologies for use with 2-D gels.

Figure 14:
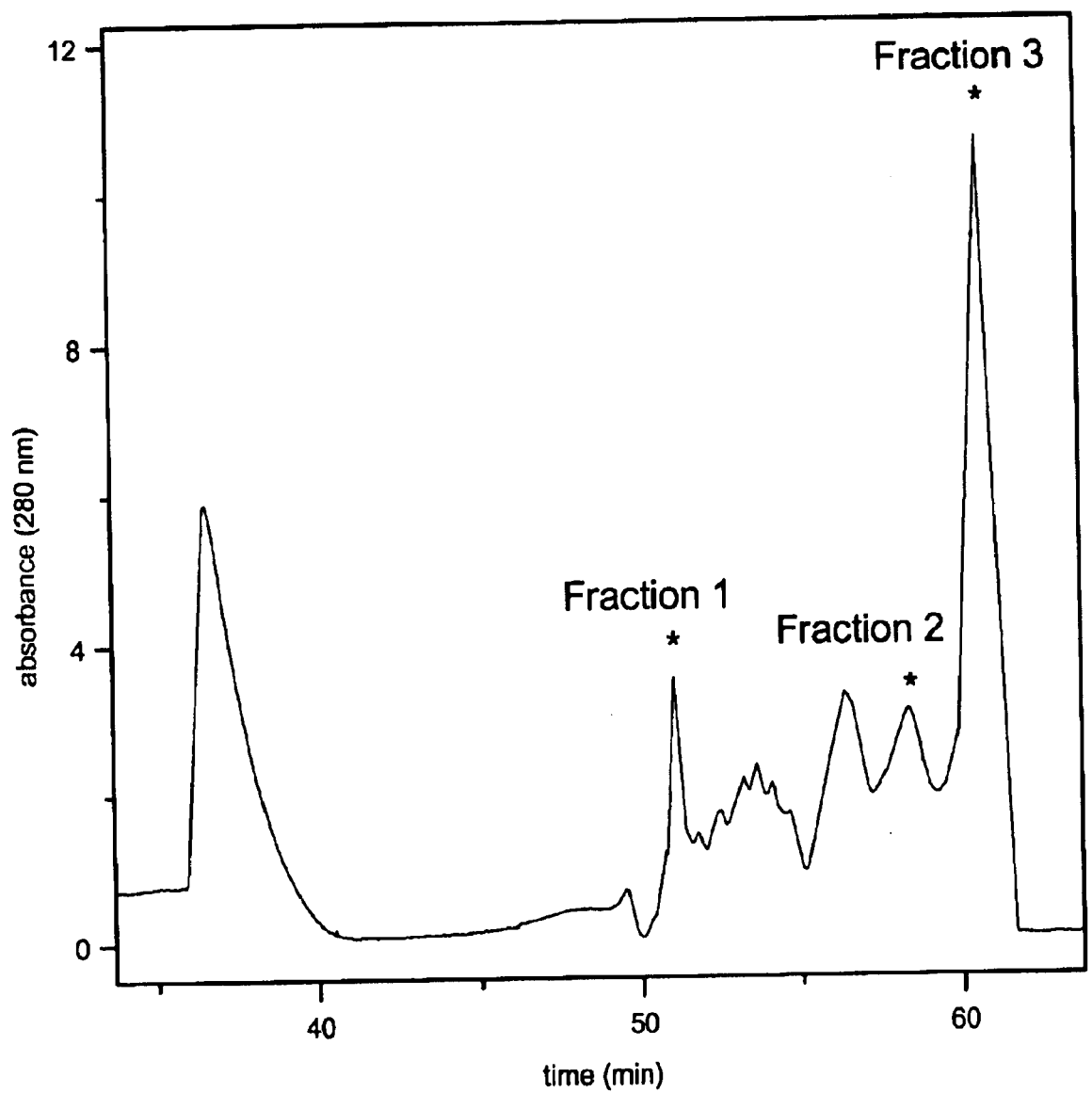
FIG. 14 shows a chromatofocusing profile of MCF-10A whole cell lysate.
Figure 15:
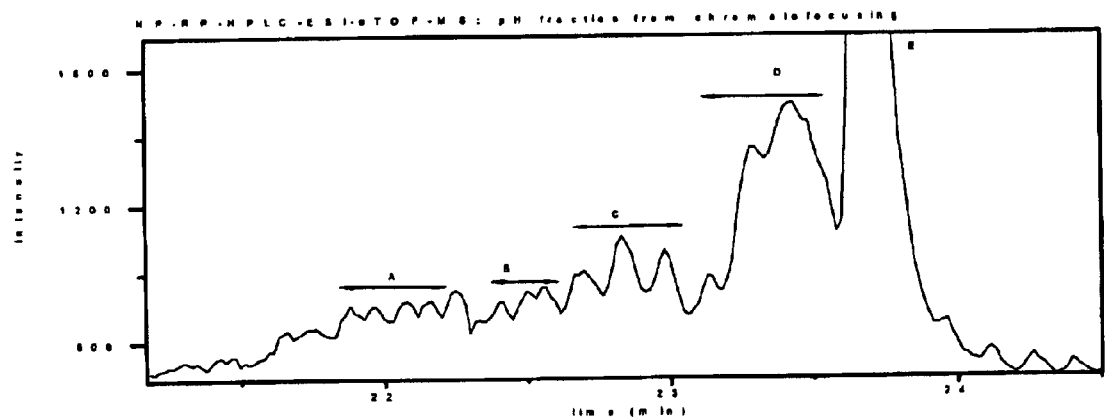
FIGS. 15A, B, and C show NP-RP-HPCL-ESI-oaTOF TIC (total ion count) profile of three sample fractions identified in FIG. 14.
Figure 15:
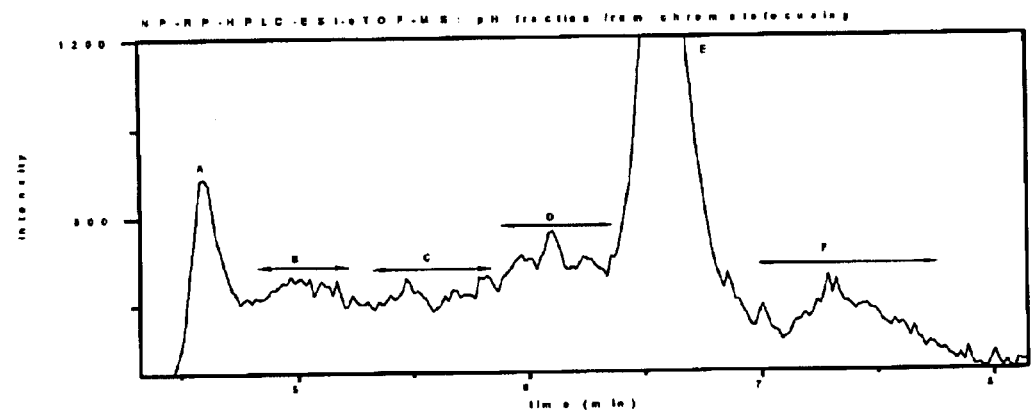
Figure 15:
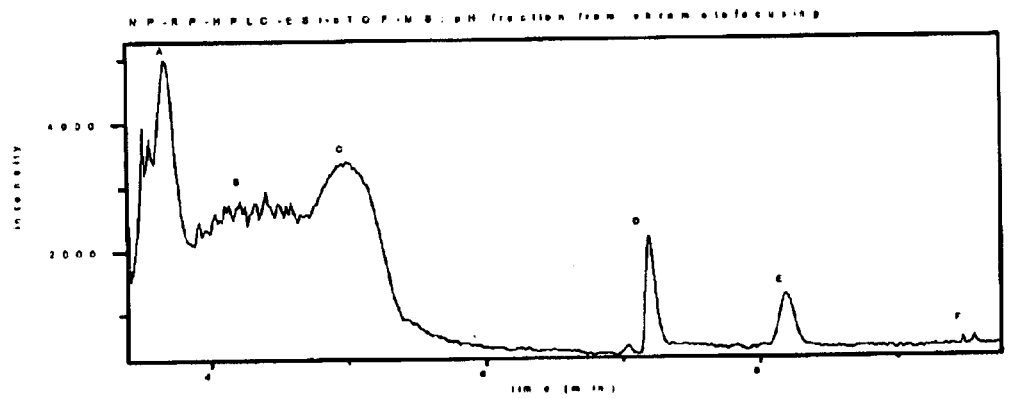
Figure 16:
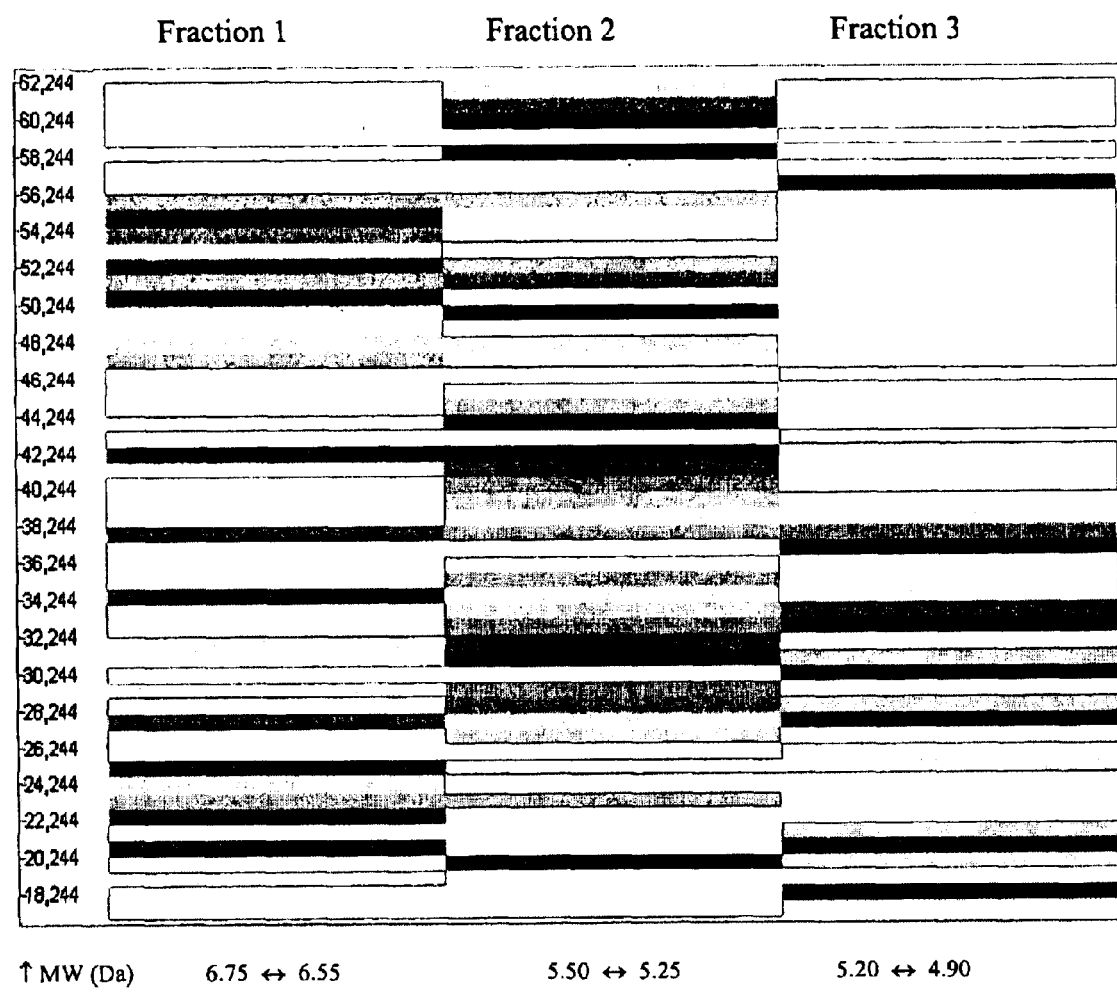
FIG. 16 shows an integrated and deconvoluted TIC profile of the three sample fractions from FIG. 15, as generated with MaxEnt1 software.

An exemplary embodiment of the chromatofocusing techniques of the present invention are provided in Example 7. Data from these experiments is shown in FIGS. 14–16. FIG. 14 shows the CF profile of MCF-10A whole cell lysate (pH 7 to 4). Fractions 1 to 3 were further analyzed with NP-RP-HPLC-ESI-oaTOF MS (described in detail below). FIGS. 15A–C show the NP-RP-HPLC-ESI-oaTOF TIC (total ion count) profile of the three fractions from FIG. 14: (A) fraction 1 (pH 6.75–6.55); (B) fraction 2 (pH 5.50–5.25); and (C) fraction 3 (pH 5.20–4.90). By integrating and deconvoluting the TIC profiles with the MaxEnt1 software (described in detail below), the mass spectra for all three fractions are displayed in a 2-D format as shown in FIG. 16. FIG. 16 shows the integrated TIC in one 2-D protein map where the vertical column is the molecular weight while the horizontal dimension is the protein pI point. This map also contains the relative abundance information whereby the bands vary in intensity (shades of gray) depending on the amount of the protein present.

The data generated by CF-NP-RP-HPLC-ESI-oaTOF MS can be presented as 2-D maps or 2-D images much like the traditional 2-D gel images. For example, in some embodiments, the chromatograms, TICs, integrated and deconvoluted mass spectra are converted into the ASCII format before being plotted vertically, using a 256-step gray scale, such that peaks are represented as darkened bands against a white background. This scale comes in a variety of color formats. Therefore, this 2-D map provides vital information on pI, hydrophobicity, molecular weight as well as the relative abundance of separated proteins. This map can also be adjusted by zoom into a specific area of interest, for a more detailed image of all the bands therein. All the information gathered from this 2-D map can be used to examine protein expression in a cell system due to the disease state, pharmaceutical treatment or environmental change. Since the image is automatically digitized, it can be easily stored and the bands can be hyperlinked to other experimental results or related data. As a result, all the information is available from the original image.

The use of chromatofocusing with the separation, analysis, and display methods of the present invention provide a number of important advantages not previously available. For example, by combining chromatofocusing with a second separation phase (e.g., NP-RP-HPLC) and mass spectrometry analysis, a 2-D liquid phase protein map is generated which is analogous to a 2-D gel. In preferred embodiments, this is a multi-dimensional liquid chromatography (LC) whereby both chromatographic techniques are performed on-line (i.e., in an automated fashion) between two or multiple LC units with a switching valve to deliver fractions from CF to, for example, NP-RP-HPLC. Proteins are "peeled off" the CF column according to their pH, one pH unit or fraction thereof, at a time. This "peeling" feature allows for further focusing of the protein bands at their respective pI regions. The protein concentration of each pI band is thus enhanced during elution. As with the method described above, buffers can be used that are compatible with each step of the process. For example, in some embodiments, the sample preparation and CF separation involves the use of guanidine-hydrochloride and a nonionic detergent (e.g., n-octyl β-D-glucopyranoside) that is compatible with the NP-RP-HPLC and ESI-oaTOF MS.

III) Mass Spectroscopic Analysis and 2-D Display Systems and Methods

In some preferred embodiments of the present invention, separated proteins are analyzed by mass spectrometry to facilitate the generation of detailed and informative 2-D protein maps. The present invention is not limited by the nature of the mass spectrometry technique utilized for such analysis. For example, techniques that find use with the present invention include, but are not limited to, ion trap mass spectrometry, ion trap/time-of-flight mass spectrometry, quadrupole and triple quadrupole mass spectrometry, Fourier Transform (ICR) mass spectrometry, and magnetic sector mass spectrometry. The following description of mass spectroscopic analysis and 2-D protein display is illustrated with ESI oa TOF mass spectrometry. Those skilled in the art will appreciate the applicability of other mass spectroscopic techniques to such methods.

In some embodiments of the present invention, ESI oa TOF mass spectrometry is used following two dimensional protein separation to provide an accurate protein separation map. For example, in one embodiments of the present invention, proteins were analyzed from human erythroleukemia (HEL) cells. The human erythroleukemia (HEL) cell line was obtained from the Department of Pediatrics at The University of Michigan. HEL cells were cultured according to the methods described in Example 1. A preparative scale Rotofor (Biorad) was used in the first dimension separation. In this experiment, 20 mg of protein was loaded. The proteins were separated by isoelectric focusing over a 5 hour period with slight modifications to the Rotofor methods described elsewhere herein. The separation temperature was 10° C., and the separation buffer contained 0.5% n-octyl β-D-glucopyranoside (OG)(Sigma), 6 M urea (ICN), 2 M thiourea (ICN), 2% β-mercaptoethanol (Biorad) and 2.5% Biolyte ampholytes, pH 3.5–10 (Biorad).

The procedure used for running the Rotofor (Rotofor Purification System, Biorad) was a modified version of the standard procedure described in the manual from Biorad. The starting power, voltage and current were 12 W, 400 V and 36 mA respectively. The ending power, voltage and current were 12 W, 1000 V and 5 mA respectively. The 20 fractions contained in the Rotofor were collected simultaneously into separate vials using a vacuum source attached by plastic tubing to an array of 20 needles which were punched through a septum. The Rotofor fractions were aliquotted in 400 µL amounts into polypropylene microcentrifuge tubes and stored at −80° C. for further analysis as desired. The pH of the fractions was determined using pH indicator paper (Type CF, Whatman). Fractions from the Rotofor were quantified using a Bradford assay (See e.g., Wall et al., Anal. Chem., 72:1099 [2000]).

For NPS RP HPLC, separations were performed at a flow rate of 0.4 mL per minute on an analytical (3.0*33 mm) NPS RP HPLC column containing 1.5 µm C18 (ODSI) nonporous silica beads (Eichrom Technologies). The use of the 3 mm column provided more than sufficient sensitivity with the use of the LCT as well as reduced solvent consumption. The column was placed in a column heater (Timberline, Boulder Colo.) and maintained at 65° C. The separations were performed using water/acetonitrile (0.1% TFA, 0.3% formic acid) gradients. The gradient profile used was as follows: 1) 0 to 20% acetonitrile (solvent B) in 1 minutes; 2) 20 to 30% B in 2 minutes; 3) 30 to 54% B in 8 minutes; 4) 54 to 65% B in 1 minute; 5) 65 to 100% B in 1 minute; 6) 100% B in 3 minutes; 7) 100 to 5% B in 1 minute. The effective start point of this profile was one minute into the gradient due to a one-minute dwell time. The acetonitrile was 99.93+% HPLC grade (Sigma), the TFA was from 1 mL sealed glass ampules (Sigma) and the formic acid was ACS grade (Sigma). The non-ionic detergent used was n-octyl β-D-galactopyranoside (OG) (Sigma). The HPLC instrument used was a Beckman model 127s/166 and the peaks were detected on-line by a commercial ESI oa TOF/MS (LCT, Micromass, Manchester U.K.). In preferred embodiments, a detergent is used throughout the separation and detection steps that is compatible with the steps of RP HPLC and ESI oa TOF/MS (e.g., detergents of the formula n-octyl (SUGAR)pyranoside).

The ESI oa TOF/MS analyses were performed on a Micromass LCT equipped with a reflectron, a 0.5 meter flight tube and a dual micro-channel plate detector. The instrument produced protein mass spectra with a mass resolution of 5000 (FWHM). The flow from the HPLC column eluent was split to the ESI stainless steel capillary at a 1:1 ratio leaving a flow to the mass spectrometer of 0.2 mL/minute. The source temperature was held at 150° C., the desolvation temperature was 400° C., the nebulizer gas ($N_2$) was left at 50% maximum flow and the desolvation gas was held at 600 L/minute. The capillary voltage was held at +2500 V and the sample cone voltage was held at +45 V. The extraction cone was held at +3 V. The RF voltage was set at 1000 V with the first hexapole being biased to a positive DC offset of +7 V and the second hexapole being biased to a negative DC offset of −2 V. The detector voltage was held at 2900 V. Data was acquired for a maximum mass/charge range of 5000 resulting in a pusher cycle time of 90 µs. The data was stored to the ECP at a rate of 1 Hz and then transferred from this data-collecting computer to the main data analysis computer for generation of the data files and TIC.

Software used to analyze the mass spectra was the MaxEnt (version 1) software and Mass Lynx version 3.4 (Micromass). Typical deconvolution was performed with a wide target mass range, 1 Dalton resolution, 0.75 Da peak width and 60% peak height values. All deconvoluted mass spectra from a given TIC were added together to produce one mass spectrum for each TIC. The TIC mass spectra from each of the Rotofor fractions were then input to the 2D mapping software (available from Dr. Stephen J. Parus, University of Michigan, Department of Chemistry, 930 N. University Ave., Ann Arbor, Mich. 48109-1055).

Figure 9:
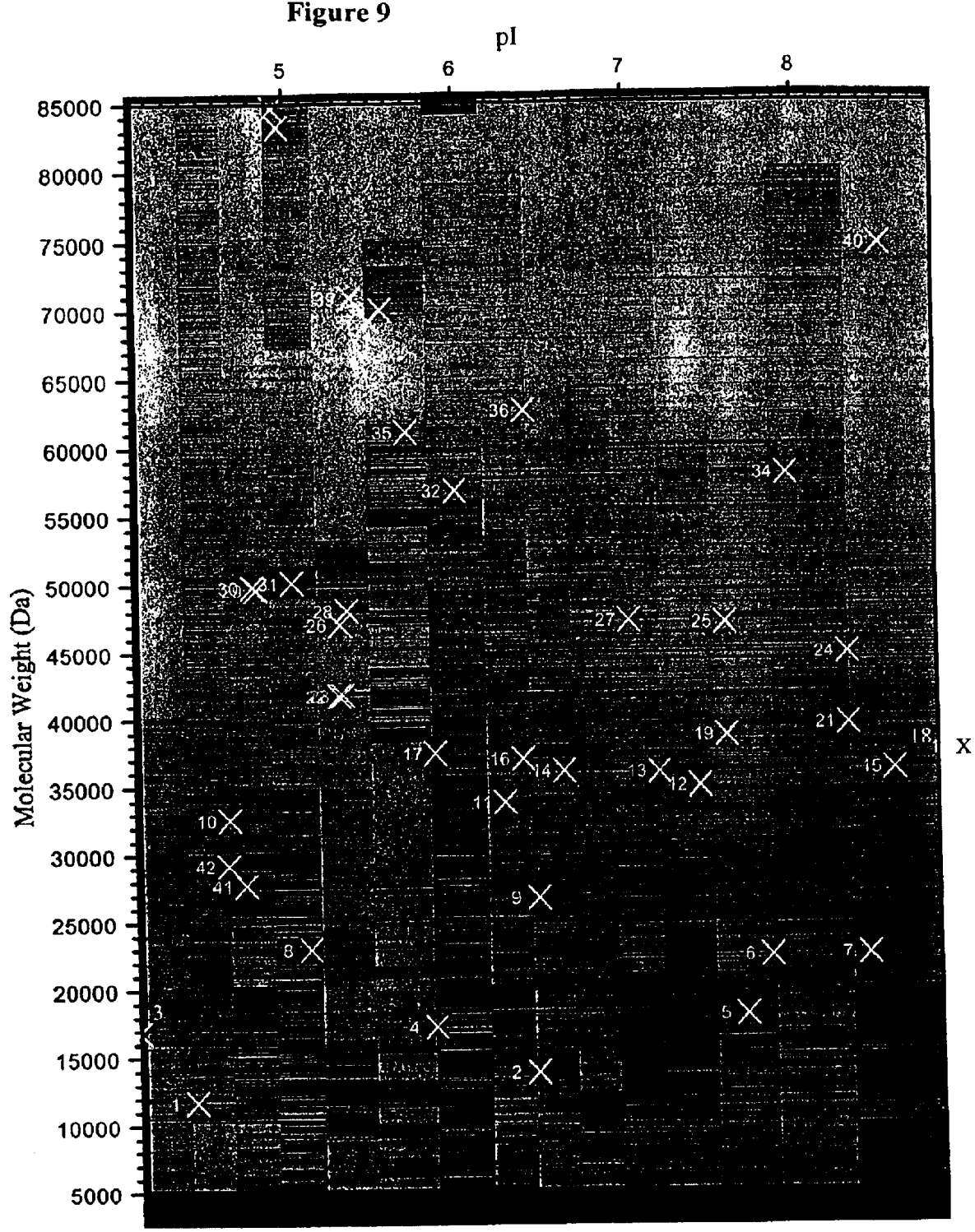
FIG. 9 shows a 2D protein image of Isoelectric Focusing-Non-porous RP HPLC-ESI oa TOF/MS (IEF-NPS RP HPLC-ESI oa TOF/MS) separation of human erythroleukemia cell lysate proteins.

The 2-D image in FIG. 9 shows protein molecular weight in the vertical dimension and protein pI in the horizontal dimension. Individual proteins are represented as bands within the grayscale image. Protein identities were matched to this image by overlaying a virtual map of all proteins rreviously identified via the NPS RP HPLC separation method described above and digest analysis with MSFit database searching.

The experimental mass values were typically better than 150 to 200 parts per million of the value recorded in the SWISS-PROT database when using the Peptident database (available at the Internet world wide web site of the SWISS-PROT database) to correct for possible post translational modifications. The pI could be estimated to within 0.01 to 0.5 pI units using intensity profiling as described below. Each vertical lane represents, in band format, all proteins observed via LCT mass spectral detection from the NPS RIP HPLC analysis of that particular Rotofor fraction. The NPS RP HPLC separations were performed on from 17 to 60 µg of protein per Rotofor fraction. The bands in the image vary in gray scale intensity according to the intensity of the source molecular weight peaks. This image has been magnified in the intensity dimension by allowing virtual saturation of the signal of the more abundant proteins. The magnification factor is 27X or 53615/2000 (max intensity/magnification intensity). The intensity has a linear dynamic range of at least 3 orders of magnitude. Some of the same protein patterns can be seen in both the liquid phase separation and a 2D gel image from Swiss-Prot the Internet world wide web site of the SWISS-PROT database). Five of the nineteen proteins identified in the 2D gel image also were found in the liquid phase separation. When comparing these images it must be kept in mind that the mass scale is linear from the liquid phase separation and logarithmic in the gel phase separation. When comparing these images it must be kept in mind that the mass scale is linear from the liquid phase separation and logarithmic in the gel phase separation.

Figure 10:
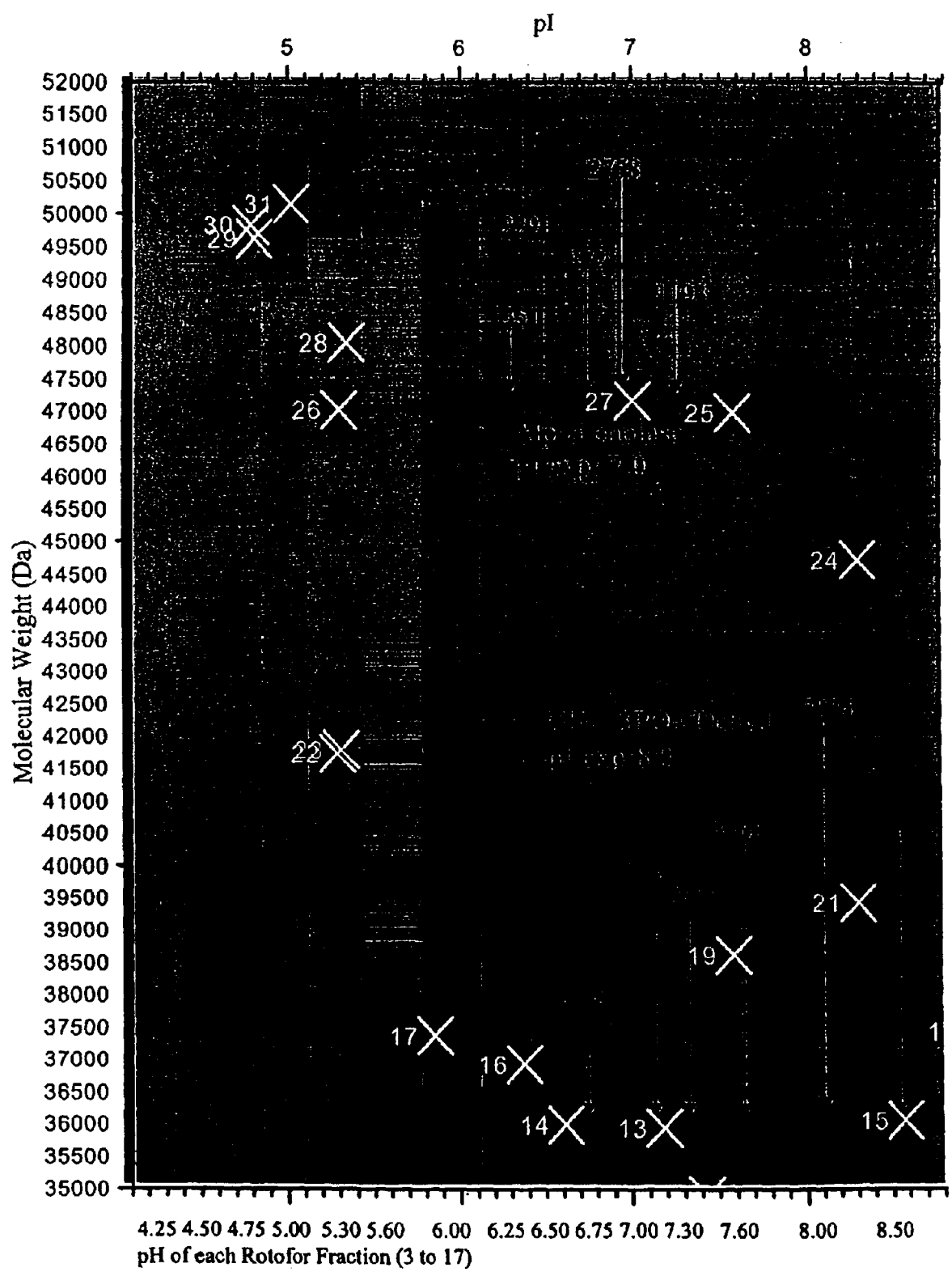
FIG. 10 shows a zoom of the 2D protein image from FIG. 9 of 35 kDa to 52 kDa mass range.
Figure 13:
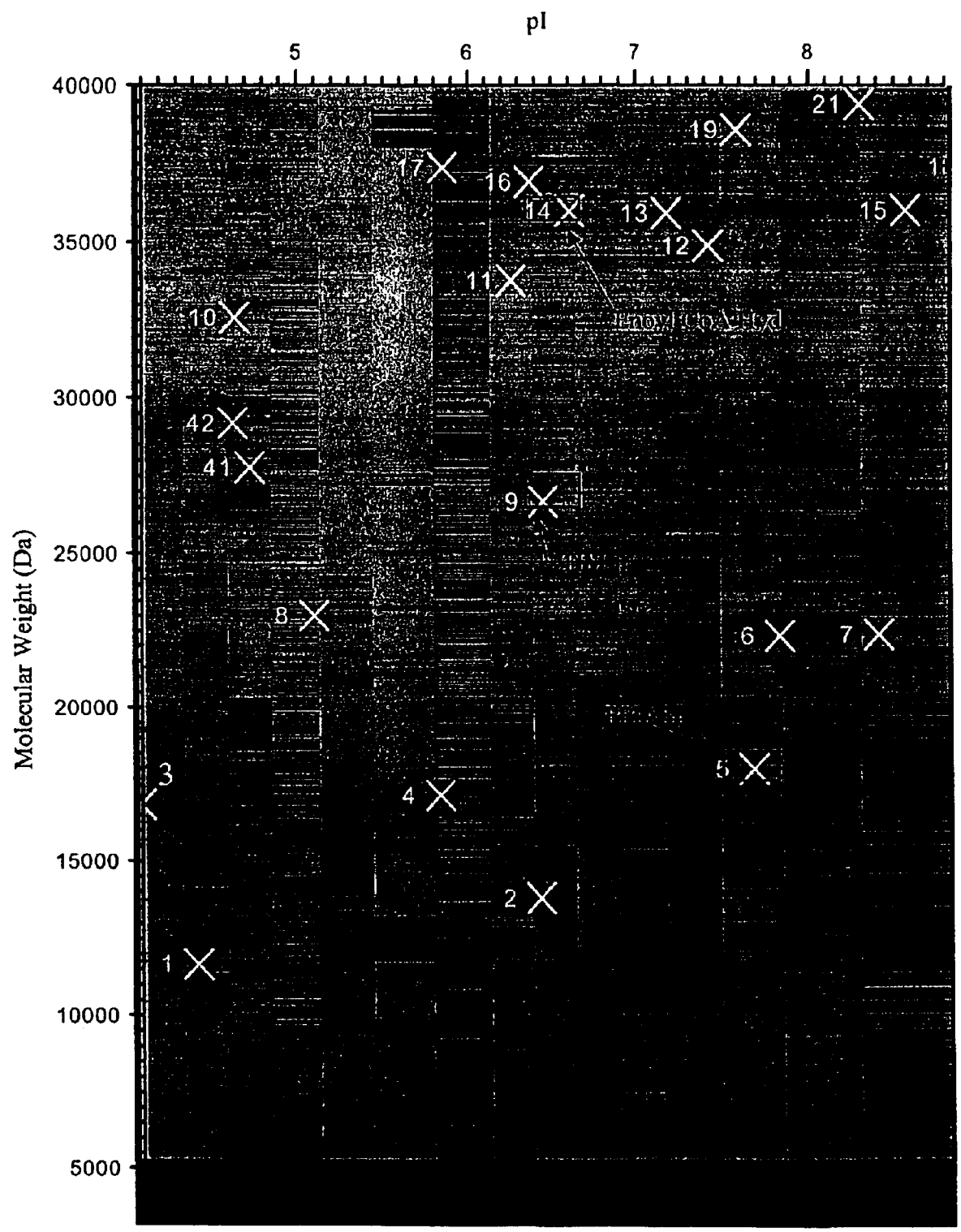
FIG. 13 shows a zoom of 2D protein image from FIG. 9 of 5 kDa to 40 kDa mass range.

The pI of proteins isolated in the 3D liquid separation method can be estimated by observing the intensity of a given protein peak over a range of pI fractions. As a protein may spread anywhere from 2 to 6 pI fractions due to diffusion and basic cathodic drift, it should be most abundant in that fraction that is closest to its own pI. This can be observed in the zoom image of FIG. 10 (See also, zoom image of FIG. 13). Using this approach, the pI of alpha-enolase is estimated to be 7.0 (database value of 7.01), and the pI of glyceraldehyde 3-$PO_4$ dehydrogenase is estimated to be 8.0 (database value of 8.57). This acidic shift may be due to a post-translational modification such as phosphorylation or glycosylation.

Figure 11:
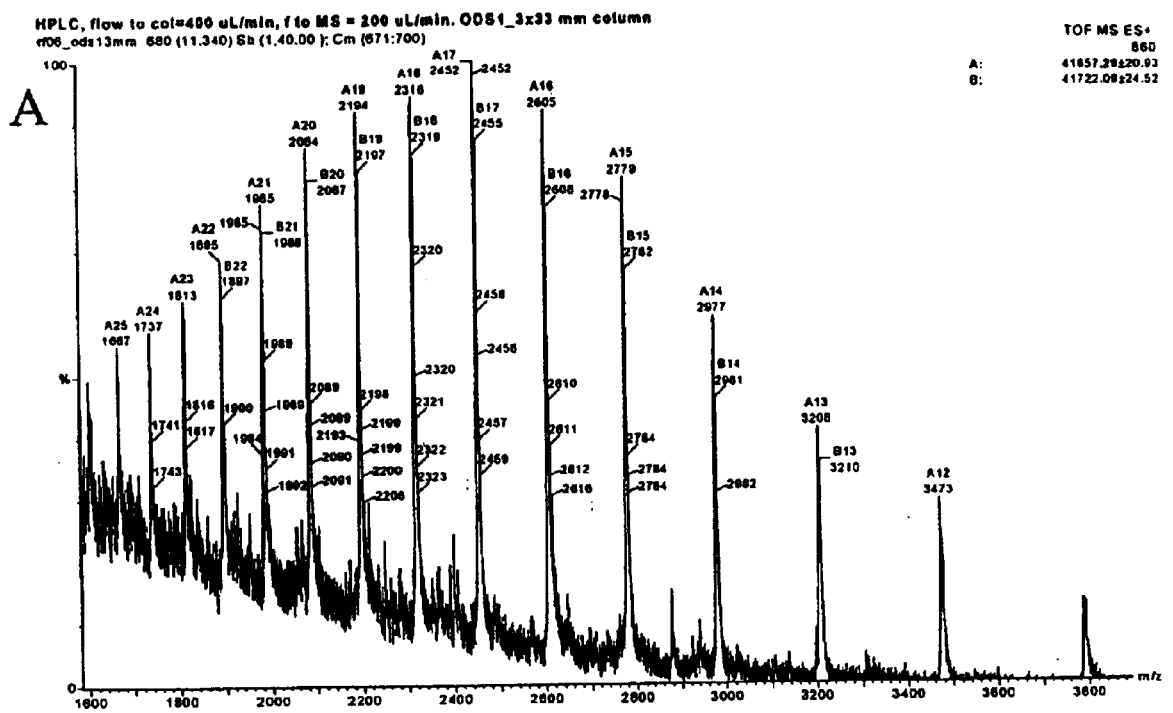
FIGS. 11A and 11B show actin multiply charged umbrella with MaxEnt deconvoluted molecular weight mass spectrum. The umbrella for beta and gamma actin is shown in FIG. 11A, each form of actin being labeled with the charge state.
Figure 11:
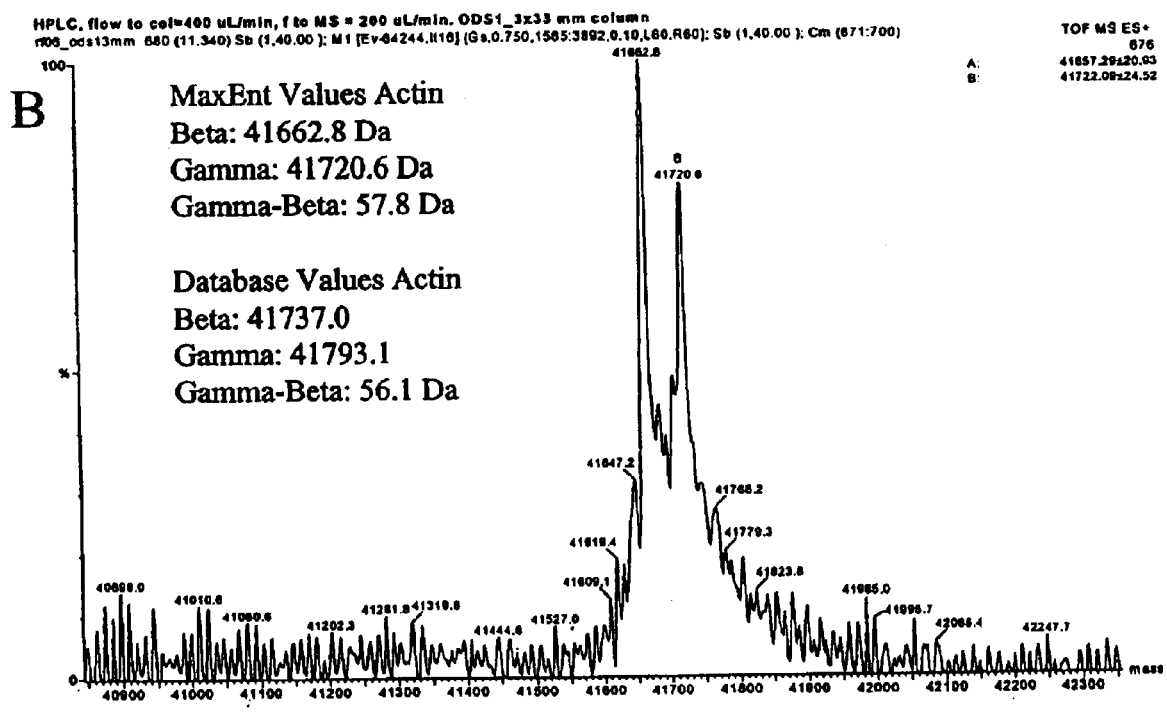

The protein molecular weights were determined by MaxEnt deconvolution of multiply charged protein umbrella mass spectra that were obtained by combining anywhere from 10 to 60 seconds of data from the initial total ion chromatogram (TIC). The umbrella for beta and gamma actin is shown in FIG. 11A, each form of actin being labeled with the charge state. FIG. 11B shows the resulting molecular weight mass spectrum for actin where the two forms of actin are separated. Note that the two forms of actin are clearly resolved from one another unlike in gel images where the actin spot always represents the co-migration of beta and gamma actin. A useful feature of the liquid phase method of the present invention is the capability of the high resolution mass spectrometry to quantitate which allows the observer to record relative levels of each form of a given protein. Consequently, it is contemplated that one cam determine the relative abundances of the phosphorylated and non-phosphorylated forms of a given protein. In addition, post-translational modifications such as phosphorylation can be found by searching the data for intervals of some integer value times 80 Da.

Figure 12:
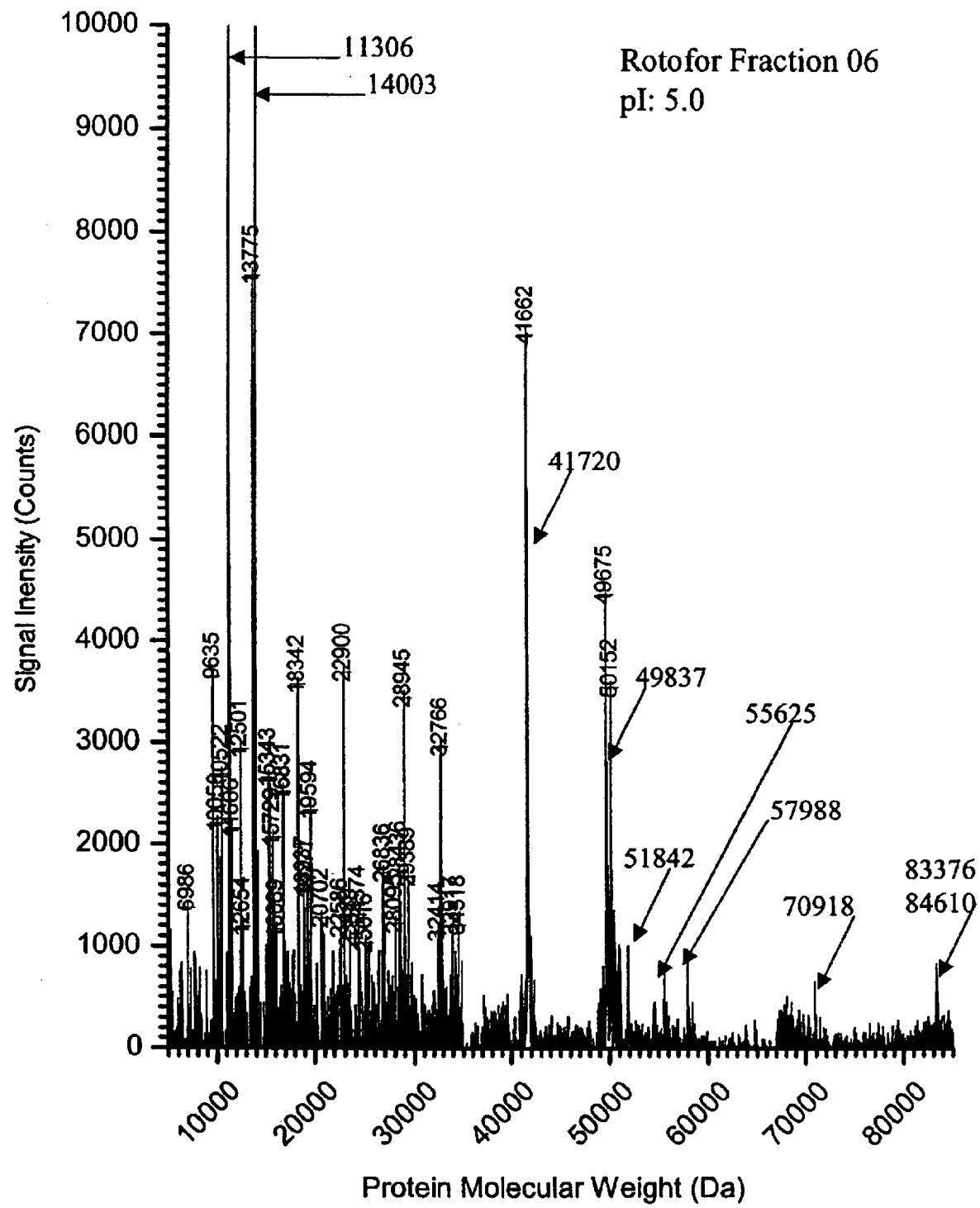
FIG. 12 shows combined protein molecular weight mass spectrum from a Rotofor fraction shown in traditional peak format.

FIG. 12 shows the traditional peak view format of one of the Rotofor fraction's combined molecular weight mass spectra. All proteins were deconvoluted and then added together into one mass spectrum. There are 44 unique protein molecular weights observed in this mass spectrum. Assuming similar numbers of unique masses in all 15 of the Rotofor fractions analyzed herein, and accounting for longitudinal diffusion between fractions, it is estimated that approximately 220 unique protein masses in the image from a pI of 4.1 to a pI of 8.75. The Rotofor produces 20 fractions, though only 15 were analyzed in this work, so that around 300 unique masses should be observed in the full analysis of all Rotofor fractions. It is contemplated that lower level proteins not obtained in the above experiment can be obtained using improved HPLC gradients, 53 mm long columns and more detailed MaxEnt analyses. Using such methods, it is contemplated that the number of unique masses will be around 750.

As shown in the above experiments, the 2D protein image from the IEF-NPS RP HPLC-ESI oa TOF/MS separation of the human erythroleukemia cell lysate provides high mass resolution and high accuracy imaging of the proteins. The mass resolution allows the image to show very different forms of the same protein that have small differences in mass. With a mass resolution of 5000 Da, a 50000 Da protein can be resolved from a 50010 Da protein. Clearly, single phosphorylations on entire proteins can be observed with this level of resolution. Quantitative comparison between 2-D images can be achieved by spiking samples with known amounts of standard proteins and normalizing images through landmark proteins. Thus, the observer can detect significant abundance changes in the protein profiles of different samples. The differences can then be targeted for more detailed analysis. For example, protein bands on the image can be hyper-linked to other experimental results, obtained via analysis of that band, such as peptide mass fingerprints and MSFit search results. Thus all information obtained about a given 2-D image, including detailed mass spectra, data analyses and complementary experiments (immuno-affinity, peptide sequencing) can be accessed from the original image.

Having identified and characterized the proteins that have changed in abundance due to some disease state or drug treatment, it is possible to identify biomarkers for disease states as well as drug targets for pharmaceutical agents and monitor the presence of, or change in, such markers in a particular biological sample (e.g., tissue samples with and without exposure to a candidate drug). Indeed, drug screening and diagnostic techniques can be automated using the systems and methods of the present invention, wherein cells (e.g., experimental and control cells) are cultured, treated, and lysed using robotics and wherein the lysate is fed into the automated separation and analysis systems of the present invention.

As is clear from the above description, the methods and systems of the present invention provide a range of novel features that provide improved methods for analyzing protein expression patterns. For example, the present invention provides a combination of IEF, resulting in pI-focused proteins in liquid phase fractions, with nonporous RP HPLC and ESI oa TOF/MS to produce a 2-dimensional liquid phase protein map image analogous to that of a 2-D gel. These methods allow the identification of proteins separated by IEF-NPS RP HPLC using enzymatic digestions and mass spectrometric analysis of the resulting peptide mass fingerprints and correlation of this data with the pI and molecular of the protein found via the whole protein 3-D separation method. In some improved display embodiments of the present invention, one can view a collection of different IEF-NPS RP HPLC-ESI oa TOF/MS chromatograms in one 2-D image displaying the mass spectra in a top view protein band format, not the traditional side view peak format. The methods also allow the detection of proteins and determination of their molecular weights by analyzing the eluent from the HPLC with computational (e.g., on-line) analysis using ESI oa TOF/MS.

The IEF-NPS RP HPLC-ESI oa TOF/MS method also allows one to fully integrate and deconvolute each of the TIC's generated to display complete mass spectra of each collection of pI-focused proteins. The method also allows the display of all the integrated TIC's in one 2-D image where the vertical dimension is in terms of protein molecular weight and the horizontal dimension is in terms of protein pI. In such displays, the protein mass spectra appear as bands as they will also be viewed from the top. This image would therefore also contain relative quantitative information wherein the bands vary in intensity depending on the amount of protein present. The use of liquid phase separation techniques with the method allows for collection of protein fractions to micro-tubes or 96-well plates such that the proteins could be digested and the peptide mass maps analyzed to determine the identity of said proteins simultaneously.

IV) Automated 3D HPLC/MC Methods for Rapid Protein Characterization

In some embodiments, the present invention provides an automated system for the separation and identification of protein samples based on multiple physical properties. Accordingly, in some embodiments, the protein separation and analysis techniques described in the preceding sections are automated into one integrated, on-line system. Protein samples are separated in a first phase and a second orthogonal phase, followed by mass spectroscopy analysis. In preferred embodiments, all of the steps are automated and coordinated through an automated sample handler and a centralized control network.

Accordingly, in some embodiments, the entire separation and characterization process is controlled through one centralized control network. The network is integrated with all of the apparatus and software used for the automated process. In some preferred embodiments, the centralized control network includes a computer system. The use of a centralized control network allows for the entire separation and characterization process to be controlled from one computer terminal by one operator. The network directs sample through the appropriate separation phases. The network then controls the transfer of protein information to analysis software. The analysis software is integrated into the network and can be programmed to generate a customized report based on the information required by the user.

A. Protein Separation

As described above, the present invention provides methods for the separation of protein samples in two phases. In preferred embodiments, the methods are orthogonal, and thus allow for the generation of a two-dimensional map. In some preferred embodiments, the present invention further provides methods of automating the two phase separation.

1. Separation in a First Phase

The automated separation methods of the present invention may be used on any suitable protein sample. As discussed above, in some embodiments, the sample is solubilized in a buffer comprising a compound of the formula n-octyl SUGAR pyranoside (e.g., including, but not limited to, n-octyl β-D-glucopyransoside and n-octyl β-D-galactopyransoside).

The first dimension of the automated separation process separates proteins based on a first physical property. For example, in some embodiments of the present invention proteins are separated by charge (e.g., ion exchange chromatography). In some preferred embodiments, cation exchange chromatography is used to separate positive proteins and anion exchange chromatography is used to separate negatively charged proteins. However, the first dimension may employ any number of separation techniques including, but not limited to, ion exclusion, isoelectric focusing, normal/reversed phase partition, size exclusion, ligand exchange, liquid/gel phase isoelectric focusing, and adsorption chromatography.

In some preferred embodiments, the first separation phase is conducted in the liquid phase. In some embodiments, the first phase is ion exchange. In such embodiments, it is preferred that samples are de-salted prior to the second separation phase. In some embodiments, desalting is performed on an automated solid phase extraction (SPE) system. In some embodiments, both the ion exchange and the desalting are performed on the same automated SPE system. In other embodiments, the ion exchange is performed on a column and the eluate is directed into the automated SPE system.

In some embodiments, if proteins are present in small amounts, samples can be loaded onto the SPE columns multiple times in order to obtain a sufficient amount for analysis. Thus, the present invention has the added advantage of allowing the identification of proteins with a low level of expression.

2. Automated Sample Handling

As described in the preceding section, in preferred embodiments, samples are processed using an automated sample handling system. The present invention is not limited to any one automated sample handling system. However, in some preferred embodiments, an on-line automated, SPE system is utilized (e.g., including, but not limited to, the Prospekt automated SPE system; Spark Holland Instrumenten, The Netherlands). The advantage of on-line SPE is the direct elution of the extract from the SPE cartridge into the second phase (e.g., LC system) by the LC mobile phase. Several laborious handling steps are thus omitted, making on-line SPE much more efficient and providing superior analytical results. The superior analytical performance of on-line SPE is derived from the elimination of eluate collection, evaporation, reconstitution and injection, thus eliminating several major error sources. In addition, on-line elution transfers 100% of the purified analytes from the extraction cartridge into the LC (e.g., HPLC). This provides maximum precision and sensitivity, as well as reduced costs, thus saving solvents, glassware, and labor time. In addition, samples and SPE cartridges are processed in a completely closed system making sample tracking easy and protecting samples against light and air. It also protects the operator from contact with hazardous samples or solvents. Furthermore, less handling means fewer failures and high pressure solvent control for SPE makes the process independent of cartridge back pressure.

3. Separation in a Second Phase

In some preferred embodiments, following the first separation phase, products of the separation step are fed directly into a second liquid phase separation step. The second dimension separates proteins based on a second physical property (i.e., a different property than the first physical property) and is preferably conducted in the liquid phase (e.g., liquid-phase size exclusion). For example, in some embodiments of the present invention, proteins are separated by hydrophobicity using non-porous reversed phase HPLC (See e.g., Liang et al., Rap. Comm. Mass Spec., 10:1219 [1996]; Griffin et al., Rap. Comm. Mass Spec., 9:1546 [1995]; Opiteck et al., Anal. Biochem. 258:344 [1998]; Nilsson et al., Rap. Comm. Mass Spec., 11:610 [1997]; Chen et al, Rap. Comm. Mass Spec., 12:1994 [1998]; Wall et al., Anal. Chem., 71:3894 [1999]; Chong et al., Rap. Comm. Mass Spec., 13:1808 [1999]).

This method provides for exceptionally fast and reproducible high-resolution separations of proteins according to their hydrophobicity and molecular weight. The non-porous (NP) silica packing material used in these reverse phase (RP) separations eliminates problems associated with porosity and low recovery of larger proteins, as well as reducing analysis times by as much as one third.

In preferred embodiments, an automated on-line sample handling system utilized in the present invention fully integrates the second separation phase with the first separation step. The sample flows directly from the first phase (e.g., ion exchange) through a desalting step (e.g., SPE) to the second phase (e.g., NP-RP HPLC). In preferred embodiments (e.g., those utilizing the Prospekt system) the HPLC column is integrated into the automated sample handling system. For example, a multi valve system can be utilized where valve-switching is used to bring the extraction cartridge into the HPLC system. In some embodiments, a sample is passed through the second phase separation step (e.g., NP-RP HPLC) greater than one time (e.g., twice) in order to improve selectivity and resolution. For example, in some embodiments, two different NP-RP-HPLC columns are utilized in tandem. The automation of protein separation increases efficiency and speed as well as decreases sample loss or potential contamination that may occur through handling.

B. Protein Identification by Mass Spectroscopy

Following separation in the first and second phase, the automated sample handling system transfers samples to the mass spectroscopy step. The present invention is not limited to any one mass spectroscopy technique. Indeed, a variety of techniques are contemplated. For example, techniques that find use with the present invention include, but are not limited to, ion trap mass spectrometry, ion trap/time-of-flight mass spectrometry, quadrupole and triple quadrupole mass spectrometry, Fourier Transform (ICR) mass spectrometry, and magnetic sector mass spectrometry. In preferred embodiments, the MS analysis is automated and is performed on-line. In some embodiments, the eluent from the second separation phase is split into two fractions. A fraction of the effluent is used to determine molecular weight by either MALDI-TOF-MS or ESI oa TOF (LCT, Micromass) (See e.g., U.S. Pat. No. 6,002,127). The remainder of the eluent is used to determine the identity of the proteins via digestion of the proteins and analysis of the peptide mass map fingerprints by either MALDI-TOF-MS or ESI oa TOF. The molecular weight 2-D protein map is matched to the appropriate digest fingerprint by correlating the molecular weight total ion chromatograms (TIC's) with the UV-chromatograms and by calculation of the various delay times involved. The UV-chromatograms are automatically labeled with the digest fingerprint fraction number. The resulting molecular weight and digest mass fingerprint data can then be used to search for the protein identity via web-based programs like MSFit (UCSF).

A detailed discussion of the use of 3-D maps generated by the automated separation process of the present invention to identify and characterize proteins is provided in the above sections. In some embodiments, the present invention provides a 3-D map in which the first dimension represents a first physical property (e.g., charge or isoelectric point), the second dimension represents a second physical property (e.g., hydrophobicity or molecular weight), and the third dimension represents the molecular weight and relative abundance of proteins present in the sample. In some embodiments, the data from the 3-D protein map is used to search protein data bases in order to determine the identity of the proteins.

In some embodiments of the present invention, sample analysis is automated and integrated with the centralized control network. For example, mass spectroscopy data is transferred to an integrated computer system containing software for the generation of 3-D protein maps. The integrated computer system is also capable of searching databases and generating a report. The report is provided to the operator in a format that is customized to the particular application. For example, if an experiment was designed to identify unknown components of a solution, the report identifies components of the 3-D map as particular proteins. Conversely, if an experiment is designed to compare the protein expression profiles of two samples, the report may identify proteins that are present in one sample and absent in another or are present at different abundances between the two samples.

C. Automated Protein Separation and Characterization in Practice

Figure 17:
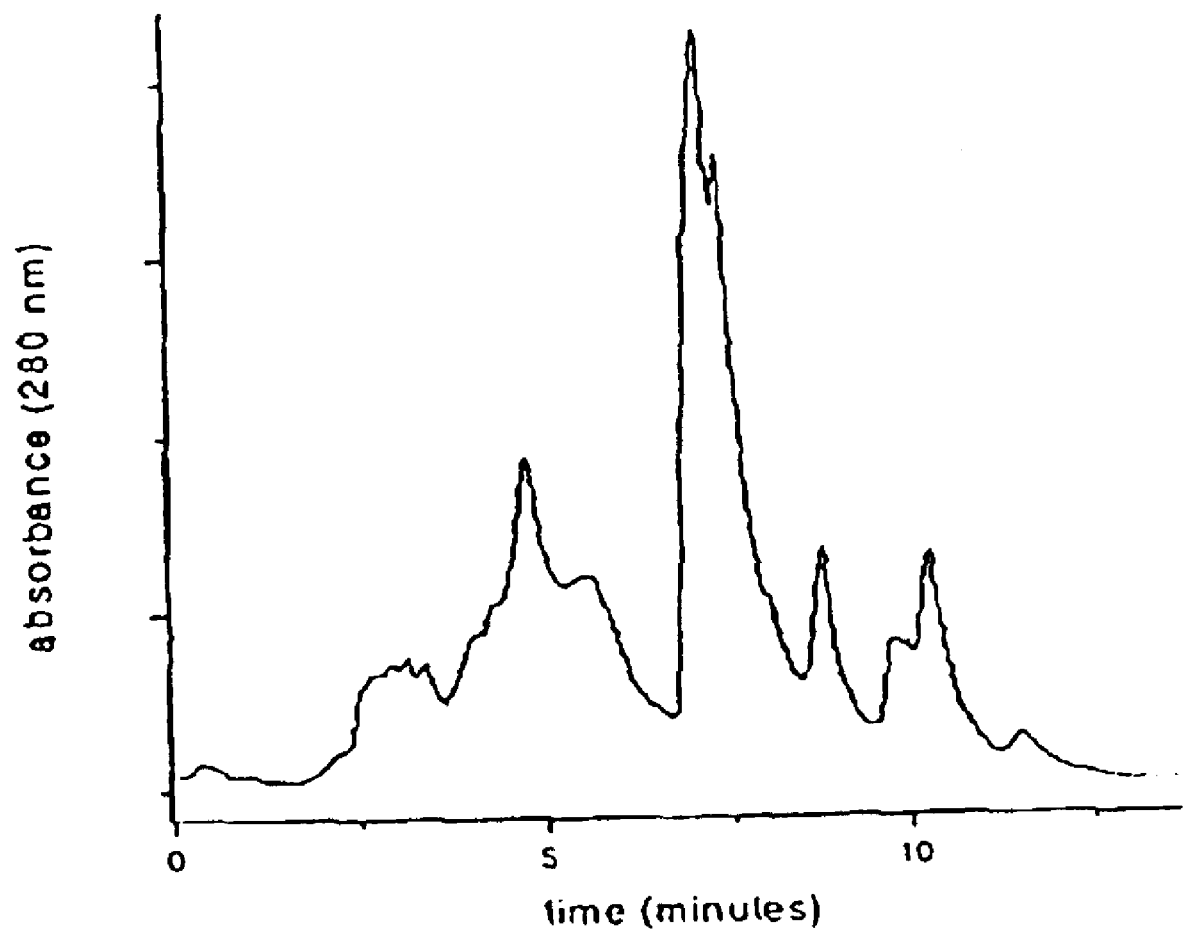
FIG. 17 shows the anion exchange profile of Siberian Permafrost whole cell lysate of sample 23-9-25.

Illustrative Example 8 describes one particular embodiment of the present invention where an automated on-line Prospekt system was used to separate a protein sample based on charge and hydrophobicity. Siberian Permafrost whole cell lysate was first separated using a mini MonoQ anion exchange column. A graph of the Mini Q column eluent is shown in FIG. 17. Fractions (1 minute each) from the anion exchange column gradient were fed directly into the second step using the automated Prospekt system. The Prospekt then trapped the fractions on 10 C4 SPE cartridges. Each cartridge was washed with the reverse-phase HPLC starting buffer to remove residual salt. The Prospekt system integrates the HPLC and SPE steps with a multi valve switching system. Following the wash step, the eluent from the SPE cartridge was directly transferred to the NP-RP HPLC column.

The fractions were separated using a tandem column method. A gradient was applied to the HPLC column. The HPLC column was then switched back to the initial buffer and allowed to equilibrate. The eluent from the first gradient is then passed through a second (different) HPLC column. The use of a second tandem column increases resolution and selectivity. This step is repeated for each of the SPE cartridges (each representing one anion exchange fraction).

Figure 18:
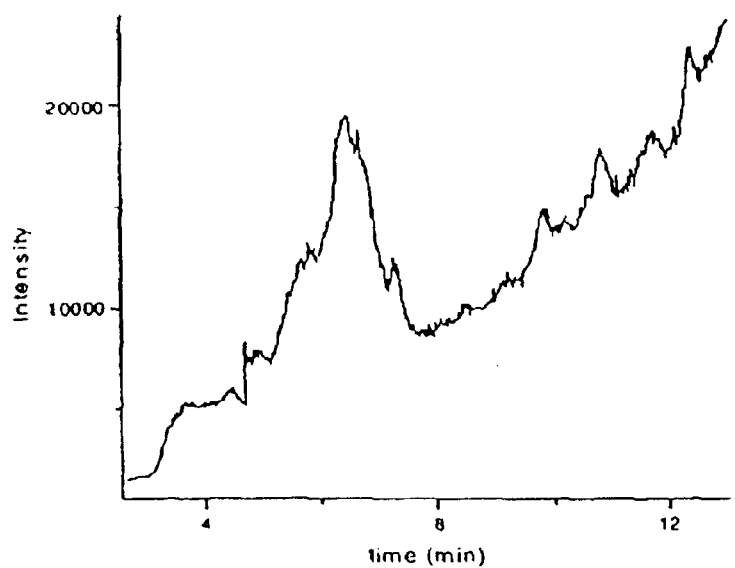
FIGS. 18A and 18B show the NP-RP-HPLC-ESI-oaTOF TIC profile of two fractions from FIG. 17.
Figure 18:
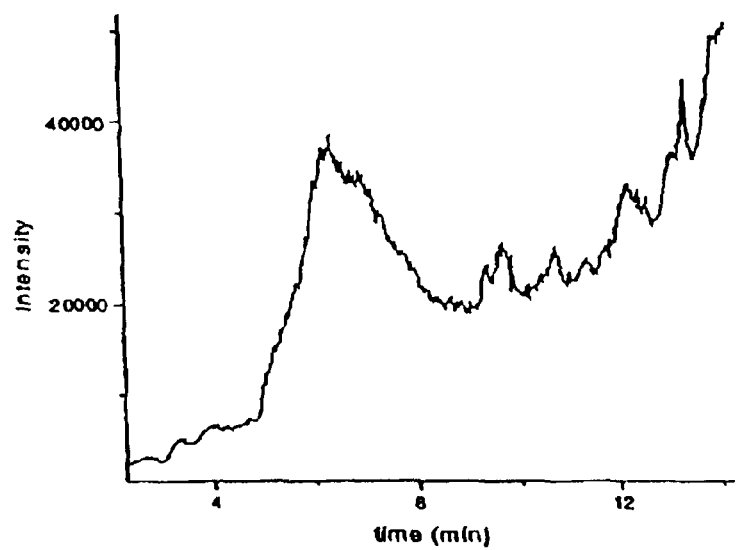

Following separation by NP-RP-HPLC, protein fractions were analyzed online by MS to determine their molecular weight and abundance. The eluent from the column was split into two fractions. One fraction is digested enzymatically before MS. Both the digested and non-digested sample were analyzed by ESI oa TOF TIC (total ion count) mass spectroscopy. Total ion count profiles are shown in FIGS. 18A and 18B.

V) 3-D Protein Mapping

In some embodiments, the present invention provides a novel gel-free 3-D protein map useful in the determination of accurate protein MWs, protein mapping and protein identification. The map is generated by separating proteins in a first and second dimension and then identifying proteins using mass spectroscopy. In some embodiments, the IEF-NPS RP HPLC-ESI TOFiMS separation method described in Example 9 is utilized. ESI TOF/MS provides rapid mass analysis of specific protein pH fractions and yields high mass resolution and high mass accuracy of intact protein molecular weights. The proteins are identified by the use of the protein MW, pI, hydrophobicity and tryptic digest mass mapping results. However, the present invention is not limited to the separation and identification method described in Example 9. Any separation method that provides the necessary information (e.g., protein pI, hydrophobicity, MW or other quantitative or physical characteristics of proteins) may be utilized.

Figure 20:
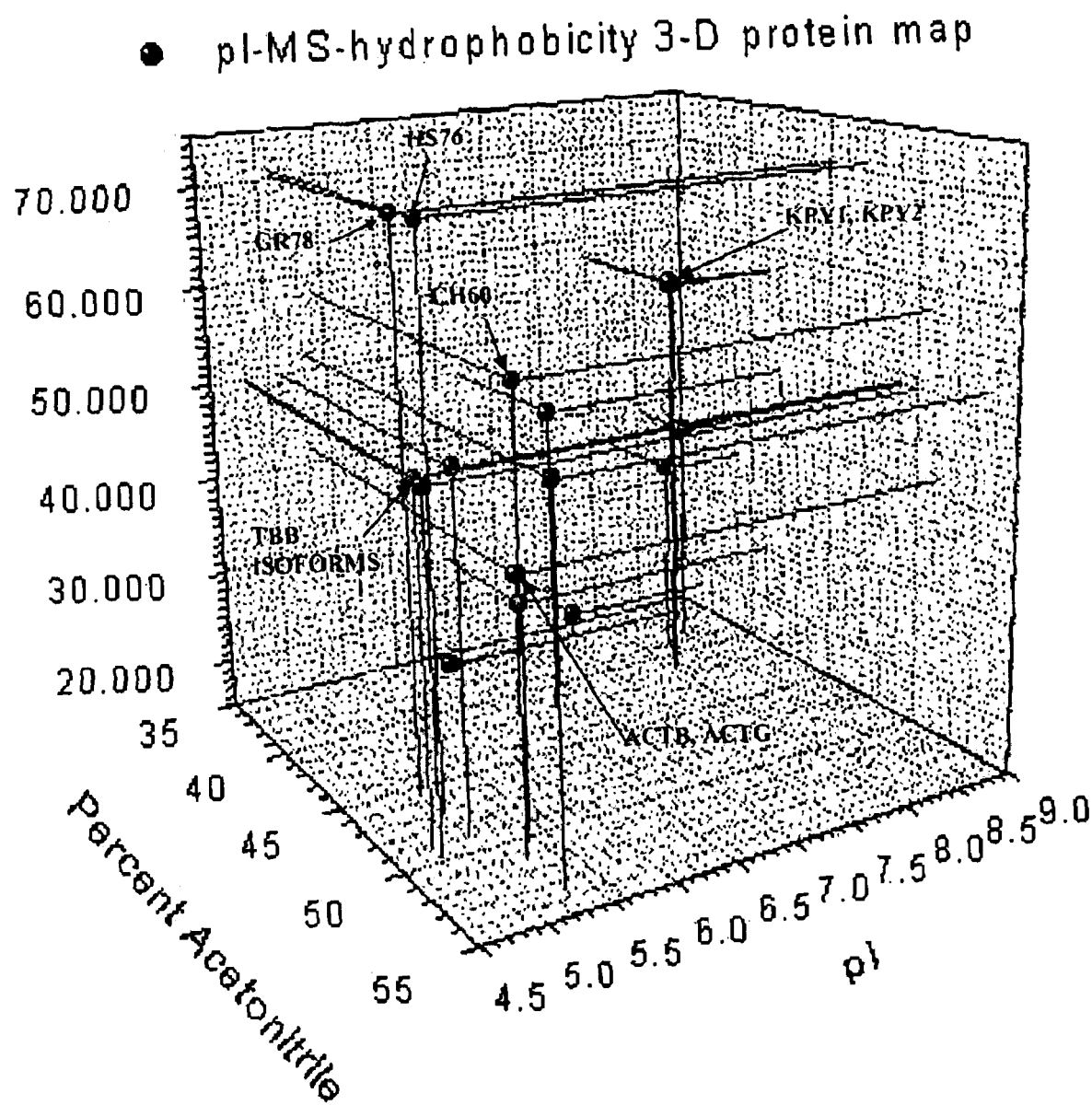
FIG. 20 shows a 3-D plot of pI vs. % B vs. MW for a IEF NP-RP-HPLC-ESI-oaTOF/MS separated HEL cell sample.
Figure 22:
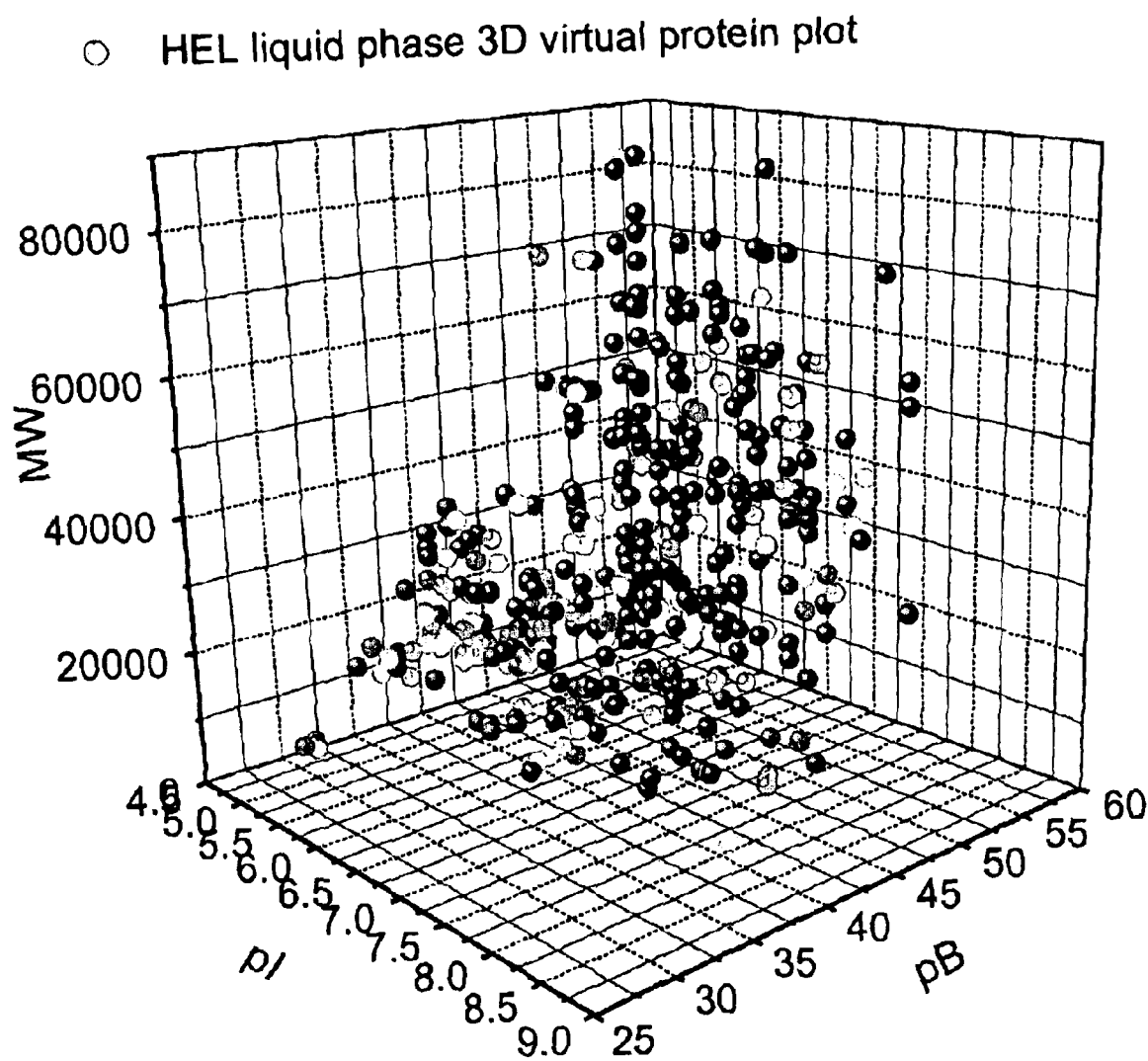
FIG. 22 shows a HEL liquid phase 3D virtual protein plot.
Figure 23:
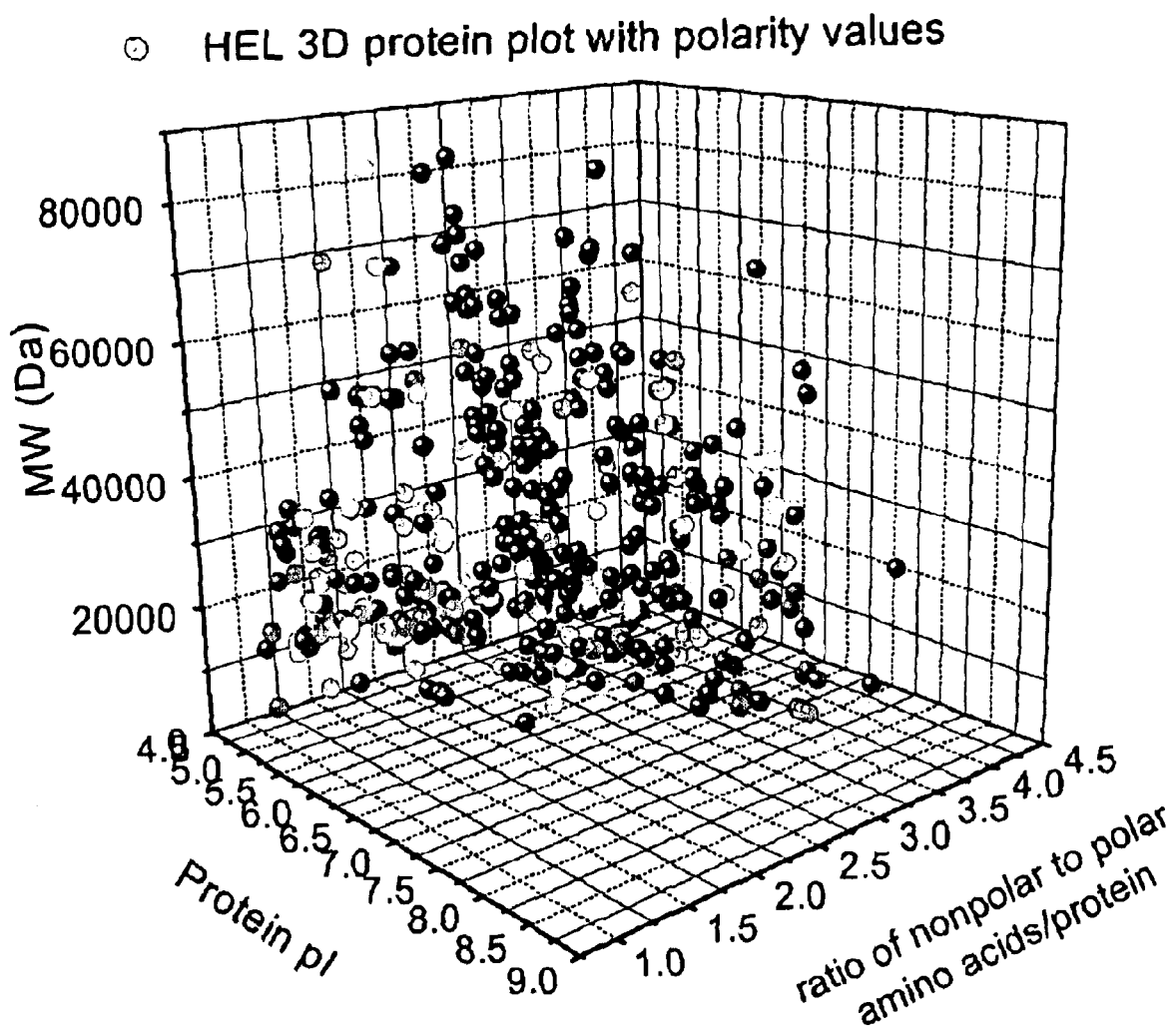
FIG. 23 shows a HEL 3D protein plot with polarity values.

In some embodiments, results are plotted in a protein map 3-D format (See FIGS. 20, 22, and 23 for illustrative examples). Proteins are mapped according to their pI, MW and, for example, percent acetonitrile at time of elution (% B). In some embodiments, spheres corresponding to individual proteins are coded (e.g., using color or greyscale) according to their relative abundance.

The % B has been correlated to the ratio of nonpolar to polar amino acids (See Example 9) and thus is representative of a fundamental and unique characteristic of the proteins just as are the pI and MW. The relationship is described by the equation % $B=23.03+6.36*(NP/P)*(7/pI)$. Accordingly, in some embodiments, the ratio of nonpolar to polar amino acids, or absolute protein hydrophobicity in a particular protein is calculated from the experimental pI, MW and % B data. For example, FIG. 23 shows a 3-D plot of the ratio of nonpolar to polar amino acids/protein, pI, and MW for a separated HEL cell extract. In other embodiments, the equation is used to calculate the % B at which a known target protein will elute from the RP HPLC separation. Such calculation are used to increase the efficiency of collecting proteins as they elute from the RP HPLC.

The methods of the present invention provide an additional parameter (i.e., third parameter) useful in deciding to reject or accept a particular protein's identification. This not only provides further evidence to either confirm or reject the identity of the protein but also may be indicative of whether or not the protein is from the cytosol, the membrane, or other cellular location. The ability of such an image to show many protein features is clearly enhanced by use of three versus two dimensions. The 3D map of the present invention can also be used as a central platform from which to track and summarize all results from an IEF-NPS RP HPLC-ESI TOF/MS experiment.

The 3-D protein mass mapping methods of the present invention are used to visualize patterns of proteins in three-dimensions just as 2D gels are now used to visualize patterns of proteins in two-dimensions. However, the 3-D protein mass map of the present invention has the advantage of providing the same information as a 2-D gel but with improved accuracy and additional information. For example, the mass accuracy from this method is typically less than +/−150 ppm while the 2-D gel has a mass accuracy of +/−10% as well as much lower mass resolution. Not only does the third dimension allow for more proteins to be resolved in one image but also it relays an important characteristic of the protein, its hydrophobicity. Accordingly, in some embodiments, the 3-D protein mass mapping method of the present invention allows for the discovery of new proteins that were previously unresolved by 2-D gel mapping methods, and that may be related to pharmaceutical drug treatments or disease states and thus aid in the discovery of new biomarkers for biomedical research.

In some embodiments, databases of 3D protein maps are created. Such databases provide information about cells, tissues and proteins that a user is working on. In addition, in some embodiments, 3D maps serve as a central point from which a user can locate a protein of interest and then, through hyperlinks to information stored in public or private databases, find out more about that protein (e.g., including but not limited to, protein identity, molecular weight, hydrophobicity, abundance, and pI). The ability to assign not only pI and MW values to proteins in databases but also hydrophobicity values allows users to utilize all three values to enhance proteome analyses.

In some embodiments, the protein maps of the present invention provide additional dimensions (e.g., fourth, fifth, sixth, or higher) comprising information about additional physical or quantitative parameters of proteins. In some embodiments, the information is stored in a database (e.g., on a computer). The user then selects three dimensions for display in a protein map. Using a computer system, the user is able to select multiple combinations of information to display in 3-D protein maps. In some embodiments, databases store additional information, including but not limited to, the cell type (e.g., cancerous or non-cancerous, differentiated or non differentiated), origin of sample (e.g., the ethnicity, race, age, or geographic location of the individual providing the sample, and the related disease state or prognosis. In some embodiments, databases and software for generating 3-D protein maps are stored on an Internet server, allowing users to access the information from any location.

In other embodiments, protein maps are also used to analyze related samples with differential display methods to determine differences between two cell types (e.g., a normal and a cancer cell line). For example, in some embodiments, differential display maps are generated by subtracting individual data points in one plot from data points in a second plot. The differences can then be displayed (e.g., by using different colors to represent proteins in each plot). In some embodiments, information from a sample (e.g., a patient suspected of having a particular disease) is compared using differential display with information obtained from the database described above. Such comparisons are useful, for example, in providing diagnosis or prognosis to an individual.

Experimental

The following examples serve to illustrate certain preferred embodiments and aspects of the present invention and are not to be construed as limiting the scope thereof.

EXAMPLE 1

HEL Cell Sample Preparation

The human erythroleukemia (HEL) cell line was obtained from the Department of Pediatrics at The University of Michigan. HEL cells were cultured (7% $CO_2$, 37° C.) in RPMI-1640 medium (Gibco) containing 4 mM glutamine, 2 mM pyruvate, 10% fetal bovine serum (Gibco), penicillin (100 units per mL), streptomycin (100 units per mL) and 250 mg of hygromycin (Sigma). The HEL cell pellets were washed in sterile PBS, and then stored at −80° C. The cell pellets were then re-suspended in 0.1% n-octyl β-D-galactopyranoside (OG)(Sigma) and 8 M urea (Sigma) and vortexed for 2 minutes to effect cell disruption and protein solubilization. The whole cell protein extract was then diluted to 55 mL with the Rotofor buffer and introduced into the Rotofor separation chamber (Biorad).

EXAMPLE 2

1-D Gel and SDS PAGE Separation

HEL cell proteins, resolved by Rotofor separation into discrete pI ranges, were further resolved according to their apparent molecular weight by SDS-PAGE. This procedure takes approximately 14 hours to complete. Samples of rotofor fractions were suspended in an equal volume of sample buffer (125 mM Tris (pH 6.8) containing 1% SDS, 10% glycerol, 1% dithiothreitol and bromophenol blue) and boiled for 5 min. They were then loaded onto 10% acrylamide gels. The samples were electrophoresed at 40 volts until the dye front reached the opposite end of the gel. The resolved proteins were visualized by silver staining. The gels were fixed overnight in 50% ethanol containing 5% glacial acetic acid, then washed successively (for 2 hours each) in 25% ethanol containing 5% glacial acetic acid, 5% glacial acetic acid, and 1% glacial acetic acid. The gels were impregnated with 0.2% silver nitrate for 25 min, and were developed in 3% sodium carbonate containing 0.4% formaldehyde for 10 min. Color development was terminated by impregnating the gels with 1% glacial acetic acid, after which the gels were digitized.

EXAMPLE 3

2-D PAGE

In order to prepare protein extracts from the HEL cells, the harvested cell pellets were lysed by addition of three volumes of solubilization buffer consisting of 8 M urea, 2% NP-40, 2% carrier ampholytes (pH 3.5 to 10), 2% β-mercaptoethanol and 10 mM PMSF, after which the buffer containing the cell extracts was transferred into microcentrifuge tubes and stored at −80° C. until use.

Extracts of the cultured HEL cells were separated in two dimensions as previously described by Chen et al (Chen et al., Rap. Comm. Mass Spec. 13:1907 [1999]) with some modifications as described below. Subsequent to cellular lysis in solubilization buffer, the cell lysates from approximately 2.5×10[6] cells were applied to isoelectric focusing gels. Isoelectric focusing was conducted using pH 3.5 to 10 carrier ampholytes (Biorad) at 700 V for 16 h, followed by 1000 V for an additional 2 hours. The first dimension tube gel was soaked in a solution of 2 mg/mL of dithioerythritol (DTE) for 10 minutes, and then soaked in a solution of 20 mg/mL of iodoacetamide (Sigma) for 10 minutes, both at room temperature. The first-dimension tube gel was loaded onto a cassette containing the second dimension gel, after equilibration in second-dimension sample buffer (125 mM Tris (pH 6.8), containing 10% glycerol, 2% SDS, 1% dithioerythritol and bromophenol blue). For the second-dimension separation, an acrylamide gradient of 11.5% to 14% was used, and the samples were electrophoresed until the dye front reached the opposite end of the gel. The separated proteins were transferred to an Immobilon-P PVDF membrane. Protein patterns in some gels were visualized by silver staining or by Coomassie blue staining, and on Immobilon-P membranes by Coomassie blue staining of the membranes.

EXAMPLE 4

Rotofor Isoelectric Focusing

A preparative scale Rotofor (Biorad) was used in the first dimension separation. This device separated the proteins in liquid phase according to their pI, and is capable of being loaded with up to a gram of protein, with the total buffer volume being 55 mL. Alternatively, for analysis of smaller quantities of protein, a mini-Rotofor with a reduced volume can be used. These proteins were separated by isoelectric focusing over a 5 hour period where the separation temperature was 10° C. and the separation buffer contained 0.1% n-octyl β-D-galactopyranoside (OG) (Sigma), 8 M urea (ICN), 2% β-mercaptoethanol (Biorad) and 2.5% Biolyte ampholytes, pH 3.5–10 (Biorad). The procedure used for running the Rotofor (Rotofor Purification System, Biorad) was of the standard procedure described in the manual from Biorad as modified herein. The 20 fractions contained in the Rotofor were collected simultaneously, into separate vials using a vacuum source attached by plastic tubing to an array of 20 needles, which were punched through a septum. The Rotofor fractions were aliquotted into 400 μL amounts in polypropylene microcentrifuge tubes and could be stored at −80° C. for further analysis if necessary. An advantage of gel methods is the ability to store proteins stably in gels at 4° C. for further use. The concentration of protein in each fraction was determined via the Biorad Bradford based protein assay. The pH of the fractions was determined using pH indicator paper (Type CF, Whatman).

EXAMPLE 5

NP RP HPLC

Separations were performed at a flow rate of 1.0 mL/minute on an analytical (4.6*14 mm) NP RP HPLC column containing 1.5 μm C18 (ODSI) non-porous silica beads (Micra Scientific Inc.). The column was placed in a Timberline column heater and maintained at 65° C. The separations were performed using water/acetonitrile (0.1% TFA, 0.05% OG) gradients. The gradient profile used was as follows: 1) 0 to 25% acetonitrile (solvent B) in 2 minutes; 2) 25 to 35% B in 2 minutes; 3) 35 to 45% B in 5 minutes; 4) 45 to 65% B in 1 minute; 5) 65 to 100% B in 1 minute; 6) 100% B in 3 minutes; 7) 100 to 5% B in 1 minute. The start point of this profile was one minute into the gradient due to a one-minute dwell time. The acetonitrile was 99.93+% HPLC grade (Sigma) and the TFA were from 1 mL sealed glass ampules (Sigma). The non-ionic detergent used was n-octyl β-D-galactopyranoside (OG) (Sigma). The HPLC instrument used was a Beckman model 127s/166. Peaks were detected by absorbance of radiation at 214 nm in a 15 μL analytical flow cell.

Protein standards (Sigma) used as MW protein markers and for correlation of retention time, molecular weight and hydrophobicity were bovine serum albumin (66 kDa), carbonic anhydrase (29 kDa), ovalbumin (45 kDa), lysozyme (14.4 kDa), trypsin inhibitor (20 kDa) and α-lactalbumin (14.2 kDa).

EXAMPLE 6

MALDI-TOF MS of NP RP HPLC Isolated Proteins

The MALDI-TOF MS analyses were performed on a Perseptive Voyager Biospectrometry Workstation equipped with delayed extraction technology, a one-meter flight tube and a high current detector. The $N_2$ laser provided light at 337 nm for laser desorption and ionization. MALDI-TOF MS was used to determine masses of peptides from protein digests using a modified (described herein) version of the two layer dried droplet method of Dai et al. (Dai et al., Anal. Chem., 71:1087 [1999]). The MALDI matrix α-cyano-4-hydroxy-cinnamic acid (α-CHCA)(Sigma Chemical Corp., St Louis, Mo., USA) was prepared in a saturated solution of acetone (1% TFA). This solution was diluted 8-fold in the same acetone solution (1% TFA) and then added to the sample droplet in a 1:2 ratio (v:v). The mixed droplet was then allowed to air dry on the MALDI plate prior to introduction into the MALDI TOF instrument for molecular weight analyses.

The proteins were collected into 1.5 mL polypropylene micro-tubes containing 20 μL of 0.8% OG in 50% ethanol. In preparation for enzymatic digestion the acetonitrile was removed via speedvac at 45° C. for 30 minutes. A solution of 200 mM $NH_4HCO_3$(ICN)/1 mM β-mercaptoethanol was then added in a 1 to 2 ratio to the remaining solution in the tubes, resulting in a solution of 50 to 100 mM $NH_4HCO_3$ with a total volume of approximately 150 μL. Subsequently 0.25 μg of enzyme was added to this solution and then the mixture was vortexed and placed in a 37° C. warm room for 24 hours. The enzymes used were either trypsin (Promega, TPCK treated), which cleaves at the carboxy side of the arginine and lysine residues, or Glu-C (Promega), which in 50–100 mM $NH_4HCO_3$ solution cleaves at the carboxy side of the glutamic acid residues.

The digest solutions were typically 100 μL in volume and 30 to 50 μL of this solution was desalted and concentrated to a final volume of 5 μL using Zip-Tips (Millipore) with 2 μL C18 resin beds. The purified peptide solution was then used to spot onto the MALDI plate for subsequent MALDI-TOF MS analysis. All spectra were obtained with 128 averages and internally or externally calibrated using the PerSeptive standard peptide mixture containing angiotensin I, ACTH(1–17), ACTH(18–39) and ACTH(7–38) (PerSeptive Biosystems).

These digests were then used to aid in the identification of the proteins by MALDI-TOF MS analysis and MSFit database searching (Wall et al., Anal. Chem., 71:3894 [1999]). The peptide mass maps were searched against the Swiss and NCBInr protein databases using MSFit allowing for 2 missed cleavages. The molecular weight ranged from 5 kDa to 70 kDa and the pI ranged over the full pI range. Externally calibrated peptide masses were searched with 400 ppm mass accuracy and internally calibrated peptide masses were searched with 200 ppm mass accuracy.

EXAMPLE 7

Chromatofocusing

In one exemplary embodiment of the chromatic focusing techniques of the present invention, proteins are extracted from cells using chemical lysing procedure. The lysis buffer consists of 6M guanidine-hydrochloride, 20 mM n-octyl β-D-glucopyranoside and 50 mM Tris. Cells are vortexed rigorously and kept overnight at −20° C. They are subsequently centrifuged at 17,000 rpm for 20 min. The supernatant is removed from the cell debris and re-centrifuged at high speed to further remove any particulate. For the best reproducible results, lysate is best used within 48 hrs. Buffers for this CF are (A) Imidazole-HAC, 0.1% guanidine-hydrochloride, 0.05% n-octyl β-D-glucopyranoside, pH 7.2, and (B) Polybuffer 74 (diluted 1:10), 0.1% guanidine-hydrochloride, 0.05% n-octyl β-D-glucopyranoside, pH 4. The CF column in this example is Mono P HR 5/20 (Amersham Pharmacia, Uppsala, Sweden) with a flowrate of 1 mL/min at room temperature. Prior to injection lysate is equilibrated with buffer A with a loading time of 20 min. The sample loadability for this CF column is 10 mg of protein. The separation profile is monitored at 280 nm while the pH gradient is monitored using a pH flowcell meter, also from Amersham Pharmacia.

The CF column is equilibrated with buffer A to define the upper pH range (7 in this case) of the pH gradient. The second "focusing" buffer B is then applied to elute bound proteins, in the order of their isoelectric (pI) points. The pH of buffer B is 4, which defines the lower limit of the pH gradient. The pH gradient is formed as the eluting buffer B titrates the buffering groups on the ion-exchanger.

The pI-focused liquid fractions from CF are analyzed in the second dimension using NP-RP-HPLC. Non-porous RP-HPLC columns (Eichrom Technologies, Darien, Ill., USA) are used as the second orthogonal separation dimension after CF in order to obtain a 2-D protein map that is capable of competing with 2-D gel. These columns are excellent for protein separation due to their high protein recovery, speed and efficiency. To achieve optimal protein separation, the columns should be kept at a high temperature (e.g., 60° C.). This elevated temperature also improves selectivity. Selectivity as well as resolution can also be enhanced by using multiple NP columns in series. RP-HPLC columns packed with non-porous silica beads (Eichrom Technologies) such as ODS1, 2 and 3 are all well suited for these tasks.

Proteins that elute from NP-RP-HPLC separation can be directly analyzed by MS to determine their molecular weight, identity and relative abundance. In this case the eluted proteins are sized simultaneously by ESI-oaTOF MS (LCT, Micromass, Manchester, UK). The other part of the eluted proteins from the split valve can be collected using a fraction collector for enzymatic digestion to obtain peptide maps with a MALDI-TOF MS, ESI-QIT-reTOF MS, or ESI-oaTOF MS (LCT). Information such as the molecular weight, pI and peptide map of a protein can then be entered into a web-based protein database program such as MS-Fit (e.g., http://prospector.ucsf.edu) for protein identification.

EXAMPLE 8

Automated 3-D IE NP-RP-HPLC-ESI-oa TOF MS

This example describes an automated system for protein separation and identification based on charge, hydrophobicity, and mass. Protein samples are separated based on charge using an ion exchange (IE) column. Protein fractions are then trapped on a solid phase extraction (SPE) column for desalting using an automated Prospekt system. The Prospeckt system then directs the protein fractions to a nonporous-reverse phase HPLC column (NP-RP-HPLC). The samples are then identified using ESI oa TOF mass spectroscopy.

A. Protein Separation and Trapping by SPE

Siberian Permafrost whole cell lysate of sample 23-9-25 (obtained from Jim Tiendje, Department of Microbial Ecology, Michigan State University) was lysed using a chemical lysis procedure. The lysis buffer contained 6M guanidine-HCL, 20 mM n-octyl β-D-glucopyransoside and 50 mM Tris. The cells were vortexed vigorously and stored overnight at 0° C. The cells were then centrifuged at 17,000 rpm for 20 minutes. The supernatant was removed from the cellular material and then mixed 1:1 with an equilibration buffer for IE (10 mM $KH_2PO_4$, 5% MeOH, 0.1% n-octyl β-D glucopyranoside, pH 8). The sample was then injected into a Mini Q anion exchange column (Amersham Pharmacia, Uppsala, Sweden) with a flow rate of 1 ml/min at 27° C. Equilibration buffer was run through the column for 3 minutes, followed by a 0% to 100% gradient of buffer B (10 mM $KH_2PO_4$, 5% MeOH, 0.1% n-octyl β-D glucopyranoside, 1M NaCl, pH 7) in 15 minutes. A graph of the Mini Q column eluent is shown in FIG. 17.

Fractions (1 minute each) are each collected on a separate solid phase extraction (SPE) cartridge by directing the eluent from the IE through 10 C4 SPE cartridges. A Prospekt on-line automated SPE system (Spark Holland Instrumenten, The Netherlands) was utilized for the SPE, HPLC, and MS phases.

B. Protein Purification and Separation by NP-RP-HPLC

The initial mobile phase buffer for the RP analysis was 5% buffer B (0.1% TFA in ACN) in buffer A (0.1% TFA in $H_2O$). This solution was directed through the SPE cartridge until all the residual salt from the anion exchange mobile phase was removed. The eluent from the SPE cartridge was next directed by the Prospekt system directly to a HPLC for the second orthogonal separation phase.

Non Porous-RP columns (Eichrom Technologies, Darien, Ill.) were used as the second separation phase. A tandem column method was employed. ODSIIIE and ODSI NP RP HPLC columns (Eichrom Technoligies, Darien, Ill.) contained 1.5 µm C18 (ODSI) non-porous silica beads. Column dimentions were 4.6*33 mm (ODSIIIE) and 4.6*14 mm (ODSI). The columns were maintained at 60° C. to improve selectivity. A flow rate of 0.5 mL/min at a pressureof 5000 psi was maintained. The columns were loaded, equilibrated in the initial buffer, and the gradient was started. A gradient of buffer B (0.1% TFA in ACN) was performed as follows: 5% B for 1.5 min, 5% B to 20% B in 2 min, 20% B to 35% B in 5 min, 35% B to 60% B in 15 min, 60% B to 100% B in 5 minutes. The eluent from the first HPLC column (ODSI) was directed into the second HPLC column (ODSIIIE).

Following the gradient, the initial mobile phase buffer was run through the RP column until a stable baseline is realized. The HPLC step was repeated for each of the SPE columns (each of which contained a 1 minute fraction from the anion exchange column).

C. Protein Identification by Mass Spectroscopy

Following separation by NP-RP-HPLC, protein fractions were analyzed online by MS to determine their molecular weight and abundance. Samples were analyzed by ESI oa TOF TIC (total ion count) mass spectroscopy. Mass spectroscopy conditions were as follows: capillary 2900V, sample cone 45V, extraction cone 3V, RF lens 1000V, desolution temp or 350° C., and source temp of 120° C.

Results of the ESI oa TOF TIC analysis are shown in FIGS. 18A and B. FIG. 18A shows the total ion profile of the fraction collected from 3 to 4 of the MiniQ column; FIG. 18B shows the total ion profile of the fraction collected from 7 to 8 minutes.

EXAMPLE 9

3-D Protein Mass Mapping

Figure 21:
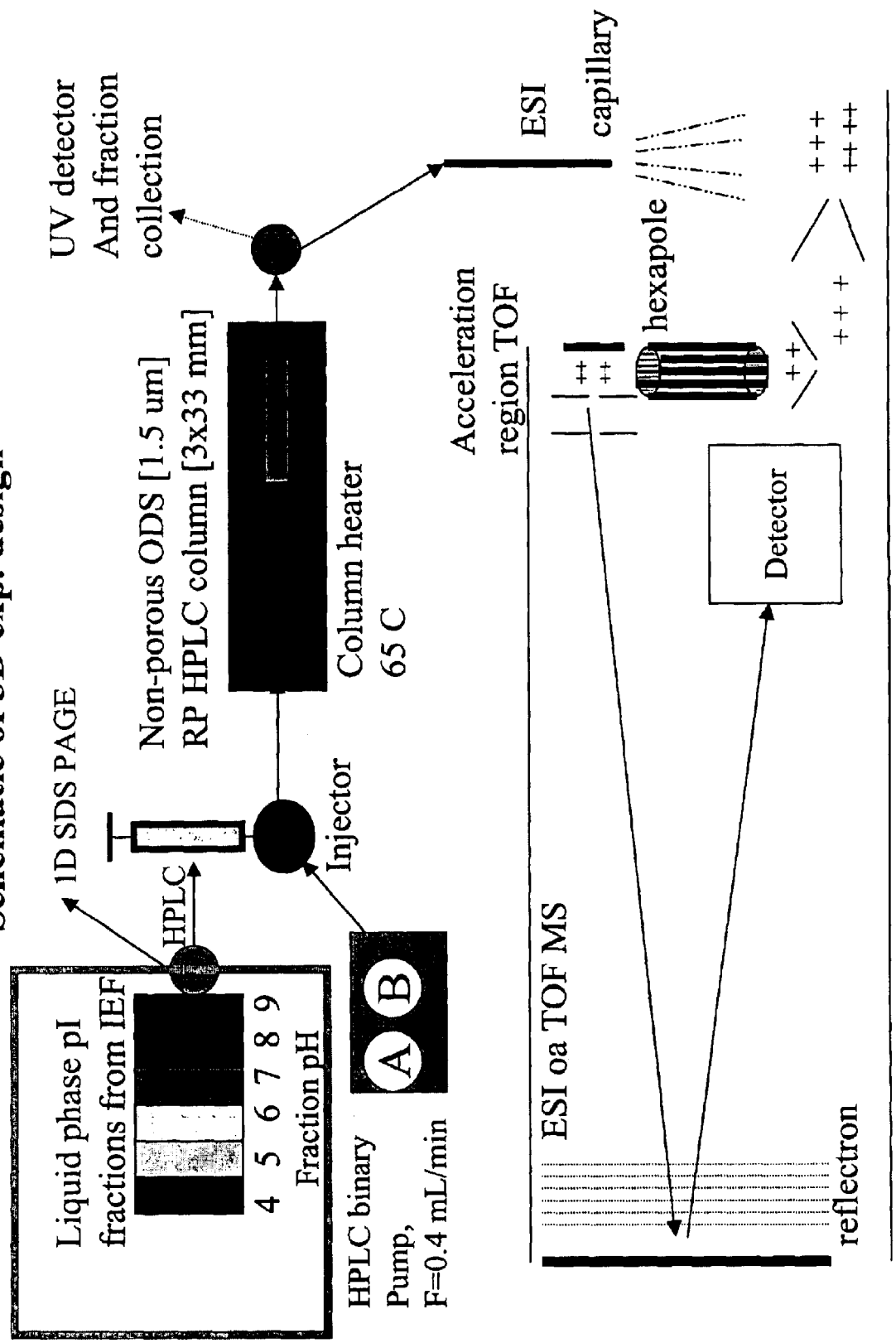
FIG. 21 shows a schematic overview of the experimental design for a 3-D protein separation experiment.

This Example describes the generation of a 3-D protein mass map for a HEL cell line lysate. Cell lysates were separated by IEF NP RP HPLC followed by ESI oa TOF MS. A schematic overview of the separation and detection protocol is shown in FIG. 21.

A. Protein Separation and Detection

The sample analyzed was the cytosolic fraction of a whole cell lysate of the human erythroleukemia (HEL) cell line. HEL cell extracts were prepared using the method described in Example 1. A liquid phase Rotofor IEF method (described in Example 4) was used to fractionate proteins from the HEL cell lysate according to pI. The protein pI fractions were then analyzed using nonporous silica (NPS) RP HPLC using the method described in Example 5 with on-line protein detection by ESI TOF/MS.

The ESI oa TOF/MS analyses were performed on a Micromass LCT equipped with a reflectron, a 0.5 meter flight tube and a dual micro-channel plate detector. The instrument produced protein mass spectra with a mass resolution of 5000 (FWHM). The flow from the HPLC column eluent was split to the ESI stainless steel capillary at a 1:1 ratio leaving a flow to the mass spectrometer of 0.2 mL/minute. The source temperature was held at 150° C., the desolvation temperature was 400° C., the nebulizer gas ($N_2$) was left at 50% maximum flow and the desolvation gas was held at 600 L/minute. The capillary voltage was held at +2500 V and the sample cone voltage was held at +45 V. The extraction cone was held at +3 V. The RF voltage was set at 1000 V with the first hexapole being biased to a positive DC offset of +7 V and the second hexapole being biased to a negative DC offset of −2 V. The detector voltage was held at 2900 V. Data was acquired for a maximum mass/charge range of 5000 resulting in a pusher cycle time of 90 µs. The data was stored to the ECP at a rate of 1 Hz and then transferred from this data-collecting computer to the main data analysis computer for generation of the data files and TIC. The proteins are identified by the use of the protein MW, pI, hydrophobicity and tryptic digest mass mapping results.

B. Generation of 3-D Protein Maps

Figure 19:
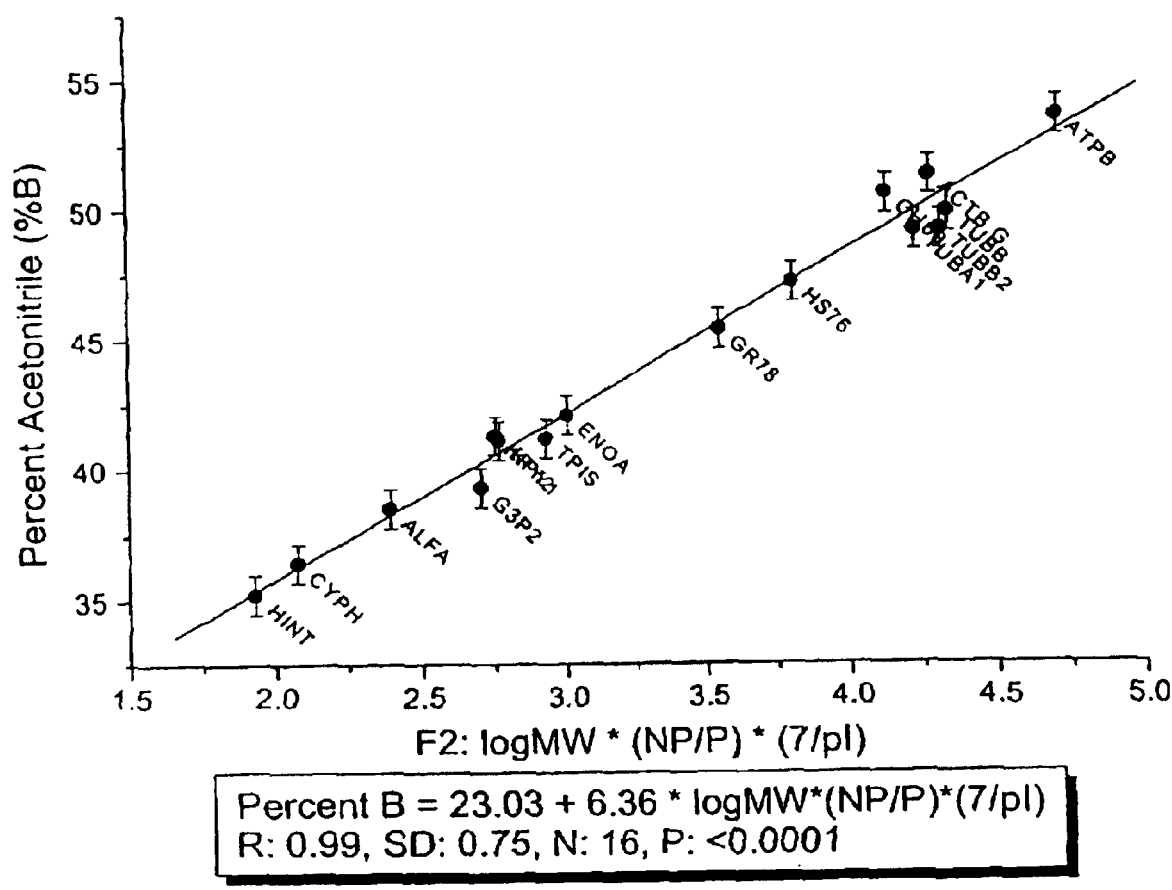
FIG. 19 shows shows a graph of logMW*(NP/P)*(7/pI) vs. % B for a IEF NP-RP-HPLC-ESI-oaTOF/MS separated HEL cell sample.

Following protein separation and mass spectroscopy, a 3-D protein map was generated. The use of the % B as a third dimension in the 3-D plot to represent the protein's hydrophobicity assumes that there is a correlation between the % B and the protein hydrophobicity. This assumption was confirmed with the following analysis. In order to characterize the nature of this relationship an initial plot of % B vs. the hydrophobicity factor F1 (F1=log of the protein MW times the ratio of the nonpolar to the polar amino acids (NP/P)) was plotted. To control for protein pI effects on solubility, the first plot was done using only data from the pH 5.1 fraction. The data showed an excellent linear fit for the pH 5.1 fraction. Addition of the basic proteins to the plot destroyed the linear relationship as all the basic proteins eluted earlier than was predicted by the pH 5.1% B vs. F1 plot. These data suggest that basic proteins are more soluble in an acidic HPLC mobile phase than acidic proteins. This solubility effect was accounted for by modifying the hydrophobicity factor F1 to hydrophobicity factor F2 as follows: % B vs. logMW*(NP/P)*(7/pI). This plot is shown in FIG. 19 and the linear fit is good (R:0.99, SD:0.75, N:16, P:<0.0001) with both basic and acidic proteins considered.

Figure 24:
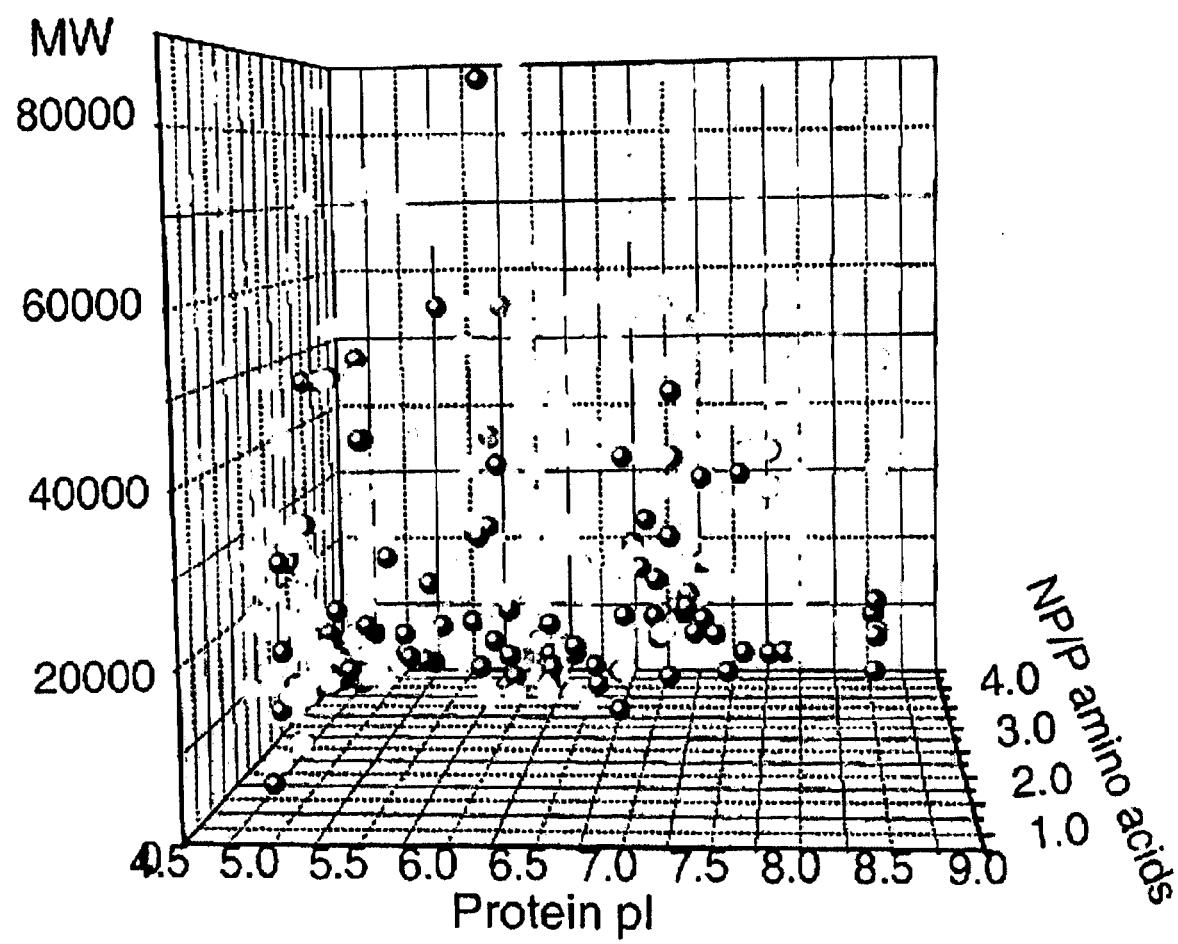
FIG. 24 shows a pI-MW view of FIG. 23.
Figure 25:
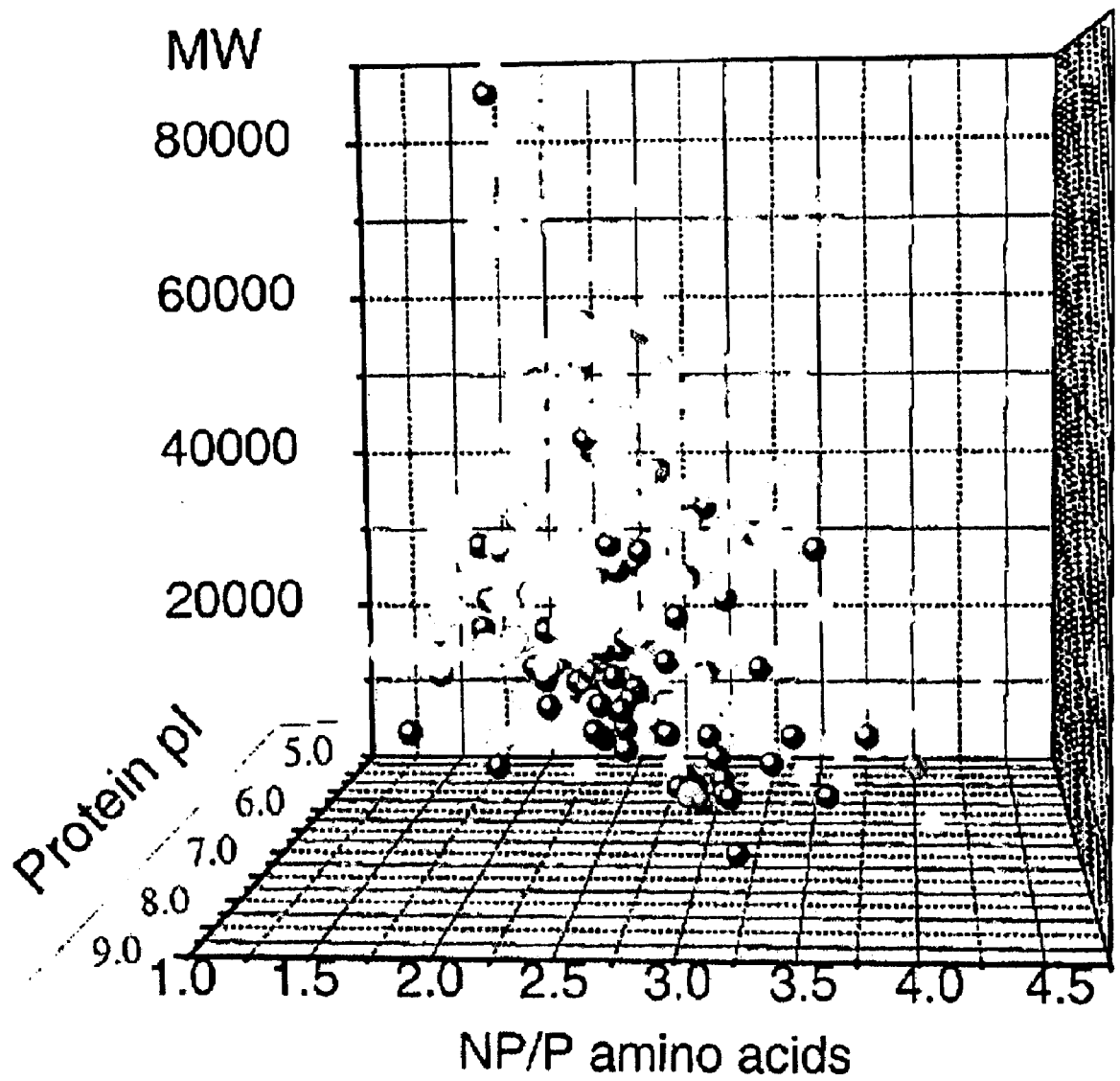
FIG. 25 shows a MW-hydrophobicity view of FIG. 23.
Figure 26:
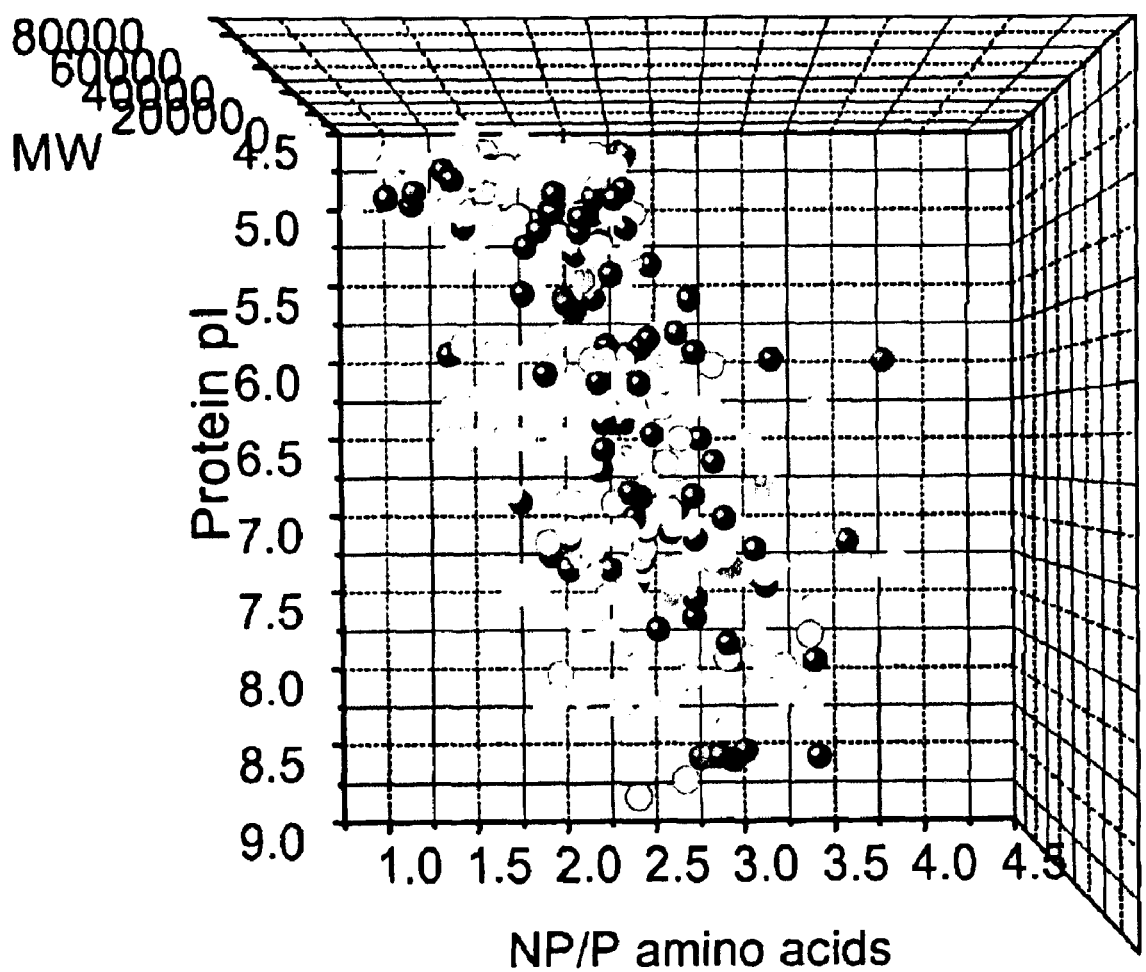
FIG. 26 shows a pI-hydrophobicity view of FIG. 23.

A 3-D mass map showing identified proteins the separated HEL protein sample is shown in FIG. 20. The three axes represent molecular weight (kDa), % B (acetonitrile), and pI. Labels on the protein spots indicate the identity of the protein. FIG. 22 shows a 3-D virtual protein plot of the separated HEL protein sample. FIG. 22 includes all of the proteins in the separated cell sample, including those that have not been identified. FIG. 23 shows the same proteins as FIG. 22, with the % B axis instead expressed in terms of hydrophobicity (ratio of nonpolar to polar amino acids per protein). The color of the spheres in FIGS. 22 and 23 represents the relative abundance of the protein, with black spheres representing the proteins found in the highest abundance. FIGS. 24–26 show 2-D representations of the 3 parameters used in the 3-D plot shown in FIG. 23.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A system comprising;
   a) a protein separation and analysis device that i) separates protein based on isoelectric point and hydrophobicity to generate separated proteins; and ii) measures mass of said separated proteins;
   b) a processor configured to receive data from said protein separation and anlysis device, said data comprising protein charge, hydrophobicity, and mass information, wherein said processor is further configured to generate three-dimensional protein maps from said data; and
   c) a display screen configured to display said three dimensional protein maps generated by said processor.

2. The system of claim 1, wherein said 3-dimensional protein map represents said plurality of proteins as spots, wherein each of said spots represents one of said plurality of proteins.

3. The system of claim 2, wherein said protein hydrophobicity is calculated based on percent of solvent required to elute each of said plurality of proteins from an non-porous reverse phase HPLC column.

4. The system of claim 3, wherein said solvent is acetonitrile.

5. The system of claim 2, wherein said 3-dimensional protein map further comprises hyperlinks to a protein information database.

6. The system of claim 5, wherein each of said hyperlinks correspond to one of said spots, and wherein said information database comprises information selected from the group consisting of protein idenity, molecular weight, relative abundance, isoelectric point, and hydrophobicity.

7. A method for displaying 3-dimensional protein maps, comprising;
   a) providing
      i) a separated protein sample comprising a plurality of proteins;
      ii) a computer system comprising software, a computer processor, computer memory, and a display screen operably linked to said software; and
      iii) data describing 3 or more properties of said separated protein sample; wherein said 3 or more properties are protein isoelectric point, hydrophobicity, and mass, and wherein said 3-dimensional protein map displays protein isoelectric point, hydrophobicity, and mass of said separated protein sample; and
   b) generating a 3-dimensional protein map from said data using said software, said computer memory, and said computer processor; and
   c) displaying said 3-dimensional protein map using said display screen.

8. The method of claim 7, wherein said 3-dimensional protein map represents said plurality of proteins as spots, wherein each of said spots corresponds to one of said plurality of proteins.

9. The method of claim 7, wherein said protein hydrophobicity is calculated based on percent of solvent required to elute each of said plurality of proteins from an non-porous reverse phase HPLC column.

10. The method of claim 9, wherein said solvent is acetonitrile.

11. The method of claim 8, wherein said 3-dimensional protein map further comprises hyperlinks to a protein information database.

12. The method of claim 11, wherein each of said hyperlinks correspond to one of said spots, and wherein said information database comprises information selected from the group consisting of protein identity, molecular weight, relative abundance, isoelectric point, and hydrophobicity.

* * * * *